United States Patent
Goble et al.

(10) Patent No.: US 7,393,844 B2
(45) Date of Patent: Jul. 1, 2008

(54) TETRAHYDROPYRANYL CYCLOPENTYL HETEROCYCLIC AMIDE MODULATORS OF CHEMOKINE RECEPTOR ACTIVITY

(75) Inventors: Stephen D. Goble, Edison, NJ (US); Alexander Pasternak, Princeton, NJ (US); Sander G. Mills, Scotch Plains, NJ (US); Changyou Zhou, Plainsboro, NJ (US); Lihu Yang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 258 days.

(21) Appl. No.: 10/550,111

(22) PCT Filed: Mar. 12, 2004

(86) PCT No.: PCT/US2004/007831

§ 371 (c)(1),
(2), (4) Date: Sep. 19, 2005

(87) PCT Pub. No.: WO2004/082616

PCT Pub. Date: Sep. 30, 2004

(65) Prior Publication Data

US 2006/0178363 A1   Aug. 10, 2006

Related U.S. Application Data

(60) Provisional application No. 60/456,046, filed on Mar. 18, 2003.

(51) Int. Cl.
  C07D 491/02   (2006.01)
  C07D 413/02   (2006.01)
  A61K 31/538   (2006.01)

(52) U.S. Cl. .................. 514/230.5; 544/90
(58) Field of Classification Search ............ 544/90; 514/230.5
See application file for complete search history.

(56) References Cited

FOREIGN PATENT DOCUMENTS

WO   WO03/093231 A2   11/2003

*Primary Examiner*—Kahsay T Habte
(74) *Attorney, Agent, or Firm*—James L. McGinnis; Mark Daniel

(57) ABSTRACT

The present invention is directed to compounds of the formula (1) Wherein A, B, D, X, Y, n, $R^1$, $R^3$, $R^4$, $R^5$, $R^{15}$, $R^{16}$, $R^{17}$, $R^{18}$ and the dashed line are as defined herein which are useful as modulators of chemokine receptor activity. In particular, these compounds are useful as modulators of the chemokine receptor CCR-2

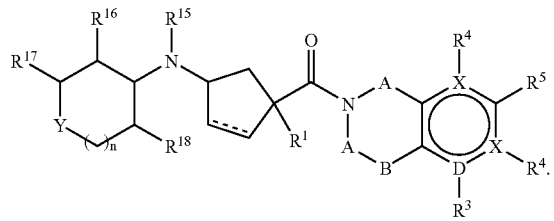

(I)

27 Claims, No Drawings

TETRAHYDROPYRANYL CYCLOPENTYL HETEROCYCLIC AMIDE MODULATORS OF CHEMOKINE RECEPTOR ACTIVITY

RELATED APPLICATION DATA

This is a National filing under 35 USC 371 of PCT/US2004/007831, filed Mar. 12, 2004, which claims priority from U.S. Ser. No. 60/456,046, filed Mar. 18 2003.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, Cytokine, 3, 165-183 (1991) and Murphy, Rev. Immun. 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., Nature, 381, 661-666 (1996)).

The chemokines are secreted by a wide variety of cell types and bind to specific G-protein coupled receptors (GPCRs) (reviewed in Horuk, Trends Pharm. Sci., 15, 159-165 (1994)) present on leukocytes and other cells. These chemokine receptors form a sub-family of GPCRs, which, at present, consists of fifteen characterized members and a number of orphans.

Unlike receptors for promiscuous chemoattractants such as C5a, fMLP, PAF, and LTB4, chemokine receptors are more selectively expressed on -1 -subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., J. Biol. Chem., 270, 22123-22128 (1995); Beote, et al, Cell. 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., Blood, 90, 908-928 (1997)); CCR-4 (or "CKR-4" or "CC-CKR-4") [MIP-1α, RANTES, MCP-1] (Rollins, et al., Blood, 90, 908-928 (1997)); CCR-5 (or "CKR-5" or "CC-CKR-5") [MIP-1α, RANTES, MIP-1β] (Sanson, et al., Biochemistry, 35, 3362-3367 (1996)); and the Duffy blood-group antigen [RANTES, MCP-1] (Chaudhun, et al., J. Biol. Chem., 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., Arthritis & Rheumatism, 42, 989-992 (1999)). A review of the role of eosinophils in allergic inflammation is provided by Kita, H., et al., J. Exp. Med. 183, 2421-2426 (1996). A general review of the role of chemokines in allergic inflammation is provided by Lustger, A. D., New England J. Med., 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and Listeria monocytogenes infection (Lu et al., J. Exp. Med., 187, 601-608 (1998); Kurihara et al. J. Exp. Med. 186, 1757-1762 (1997); Boring et al. J. Clin. Invest., 100, 2552-2561 (1997); Kuziel et al. Proc. Natl. Acad. Sci., 94, 12053-12058 (1997)). Furthermore, these animals show reduced monocyte infiltration into granulomatous lesions induced by the injection of schistosomal or mycobacterial antigens (Boring et al. J. Clin. Invest., 100, 2552-2561 (1997); Warmington et al. Am J. Path., 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1-/- or CCR2-/- mice backcrossed to APO-E-/-, LDL-R-/- or Apo B transgenic mice maintained on high fat diets (Boring et al. Nature, 394, 894-897 (1998); Gosling et al. J. Clin. Invest., 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

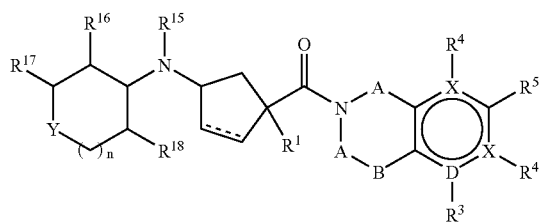

I wherein:

A, B, X, and D are defined as follows with the exceptions that A, B, X, and D cannot be simultaneously $CR^8R^8$, $CR^2R^2$, $CR^4$, and $CR^3$, respectively, and that D can only be N when at least one of A, B, or X is not $CR^8R^8$, $CR^2R^2$, or $CR^4$, respectively (where $R^8$, $R^2$, $R^4$, and $R^3$ are defined below;

A is independently selected from the group consisting of —$CR^8R^8$—, —CO—, —NR8—, and —O—, where
  $R^8$ is independently selected from hydrogen, $C_{1-6}$alkyl, $C_{0-4}$alkylCOR$^{11}$, and where $R^{11}$ is selected from: hydroxy, hydrogen, $C_{1-6}$ alkyl, —O—$C_{1-6}$alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl;

B is selected from the group consisting of —$CR^2R^2$—, —O—, —SO—, —$SO_2$—, —$NSO_2R^{14}$—, —$NCOR^{13}$—, —$NCONR^{12}R^{12}$— and —CO—, where $R^2$ is independently selected from hydrogen, $C_{1-6}$alkyl, fluoro, hydroxy, heterocycle, —$NHCOR^{13}$, —$NHSO_2R^{14}$, and —O—$C_{1-6}$alkyl, and
  where $R^{12}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$-$C_{1-6}$ alkyl, and trifluoromethyl, and
    where $R^{13}$ is selected from: hydrogen, $C_{1-6}$ alkyl, —O—$C_{1-6}$alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, and
    where $R^{14}$ is selected from: hydroxy, $C_{1-6}$ alkyl, —O—$C_{1-6}$alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, and
  where the heterocycle is unsubstituted or substituted with 1-3 substituents where the substituents are independently selected from: halo, hydroxy, —$COR^{11}$, $C_{1-3}$alkyl, $C_{1-3}$alkoxy and trifluoromethyl;

X is independently selected from a carbon atom, or a nitrogen atom;

D can be a carbon atom, and when one of B, X, or D is not $CR^2R^2$, a carbon atom, and a carbon atom, respectively, then D can also be a nitrogen atom;

Y is selected from the group consisting of:
  —O—, —$NR^{12}$—, —S—, —SO—, —$SO_2$—, and —$CR^{11}R^{11}$, —$NSO_2R^{14}$—, —$NCOR^{13}$—, —$NCONR^{12}R^{12}$—, —$CR^{11}COR^{11}$—, —$CR^{11}OCOR^{13}$— and —CO—;

$R^1$ is selected from:
  hydrogen, —$C_{1-6}$alkyl, —$C_{0-6}$alkyl-O—$C_{1-6}$alkyl, —$C_{0-6}$alkyl-S—$C_{1-6}$alkyl, —($C_{0-6}$alkyl)-($C_{3-7}$cycloalkyl)-($C_{0-6}$alkyl), hydroxy, heterocycle, —CN, —$NR^{12}R^{12}$, —$NR^{12}COR^{13}$, —$NR^{12}SO_2R^{14}$, —$COR^1$, —$CONR^{12}R^{12}$, and phenyl, where the alkyl and the cycloalkyl are unsubstituted or substituted with 1-7 substituents where the substituents are independently selected from:
    (a) halo,
    (b) hydroxy,
    (c) —O—$C_{1-3}$alkyl,
    (d) trifluoromethyl,
    (f) $C_{1-3}$alkyl,
    (g) —O—$C_{1-3}$alkyl,
    (h) —$COR^{11}$,
    (i) —$SO_2R^{14}$,
    (j) —$NHCOCH_3$,
    (k) —$NHSO_2CH_3$,
    (l) -heterocycle,
    (m) =O,
    (n) —CN,
  and where the phenyl and heterocycle are unsubstituted or substituted with 1-3 substituents where the substituents are independently selected from: halo, hydroxy, —$COR^{11}$, $C_{1-3}$alkyl, $C_{1-3}$alkoxy and trifluoromethyl;

$R^3$ is selected from:
  (a) hydrogen,
  (b) $C_{1-3}$alkyl, optionally substituted with 1-3 fluoro,
  (c) —O—$C_{1-3}$alkyl, optionally substituted with 1-3 fluoro,
  (d) hydroxy,
  (e) chloro,
  (f) fluoro,
  (g) bromo,
  (h) phenyl,
  (g) heterocycle, and
  (h) nothing, O, or hydrogen (when the Z bonded to $R^3$ is N);

$R^4$ is selected from:
  (a) hydrogen,
  (b) $C_{1-3}$alkyl, optionally substituted with 1-3 fluoro,
  (c) —O—$C_{1-3}$alkyl, optionally substituted with 1-3 fluoro,
  (d) hydroxy,
  (e) chloro,
  (f) fluoro,
  (g) bromo,
  (h) phenyl,
  (g) heterocycle, and
  (h) nothing, O, or hydrogen (when the Z bonded to $R^4$ is N);

$R^5$ is selected from:
(a) $C_{1-6}$alkyl, where alkyl is unsubstituted or substituted with 1-6 fluoro and optionally substituted with hydroxyl,
(b) —O—$C_{1-6}$alkyl, where alkyl is unsubstituted or substituted with 1-6 fluoro,
(c) —CO—$C_{1-6}$alkyl, where alkyl is unsubstituted or substituted with 1-6 fluoro,
(d) —S—$C_{1-6}$alkyl, where alkyl is unsubstituted or substituted with 1-6 fluoro,
(e) -pyridyl, which is unsubstituted or substituted with one or more substituents selected from the group consisting of: halo, trifluoromethyl, $C_{1-4}$alkyl, and $COR^{11}$,
(f) fluoro,
(g) chloro,
(h) bromo,
(i) —$C_{4-6}$cycloalkyl,
(j) —O—$C_{4-6}$cycloalkyl,
(k) phenyl, which is unsubstituted or substituted with one or more substituents selected from the group consisting of: halo, trifluoromethyl, $C_{1-4}$alkyl, and $COR^{11}$,
(l) —O-phenyl, which is unsubstituted or substituted with one or more substituents selected from the group consisting of: halo, trifluoromethyl, $C_{1-4}$alkyl, and $COR^{11}$,
(m) —$C_{3-6}$cycloalkyl, where alkyl is unsubstituted or substituted with 1-6 fluoro,
(n) —O—$C_{3-6}$cycloalkyl, where alkyl is unsubstituted or substituted with 1-6 fluoro,
(o) -heterocycle,
(p) —CN, and
(q) —$COR^{11}$;

$R^{15}$ is selected from:
(a) hydrogen, and
(b) $C_{1-6}$alkyl, which is unsubstituted or substituted with 1-3 substituents where the substituents are independently selected from: halo, hydroxy, —$CO_2H$, —$CO_2C_{1-6}$alkyl, and —O—$C_{1-3}$alkyl;

$R^{16}$ is selected from:
(a) hydrogen,
(b) $C_{1-6}$alkyl, where alkyl is unsubstituted or substituted with 1-6 substituents where the substituents are chosen from the group: fluoro, $C_{1-3}$alkoxy, hydroxy, —$COR^{11}$,
(c) fluoro,
(d) —O—$C_{1-3}$alkyl, where alkyl is unsubstituted or substituted with 1-3 fluoro,
(e) $C_{3-6}$ cycloalkyl,
(f) —O—$C_{3-6}$cycloalkyl,
(g) hydroxy,
(h) —$COR^{11}$,
(i) —$OCOR^{13}$,
or $R^{15}$ and $R^{16}$ are joined together via a $C_{2-4}$alkyl or a $C_{0-2}$alkyl-O—$C_{1-3}$alkyl chain to form a 5-7 membered ring;

$R^{17}$ is selected from:
(a) hydrogen,
(b) $C_{1-6}$alkyl, where alkyl is unsubstituted or substituted with 1-6 substituents where the substituents are chosen from the group: fluoro, $C_{1-3}$alkoxy, hydroxy, —$COR^{11}$,
(c) $COR^{11}$,
(d) hydroxy, and
(e) —O—$C_{1-6}$alkyl, where alkyl is unsubstituted or substituted with 1-6 substituents where the substituents are chosen from the group: fluoro, $C_{1-3}$alkoxy, hydroxy, —$COR^{11}$,
or $R^{16}$ and $R^{17}$ are joined together by a $C_{1-4}$alkyl chain or a $C_{0-3}$alkyl-O—$C_{0-3}$alkyl chain to form a 3-6 membered ring;

$R^{18}$ is selected from:
(a) hydrogen, and
(b) $C_{1-6}$alkyl, where alkyl is unsubstituted or substituted with 1-6 fluoro,
(c) fluoro,
(d) —O—$C_{3-6}$cycloalkyl, and
(e) —O—$C_{1-3}$alkyl, where alkyl is unsubstituted or substituted with 1-6 fluoro, or $R^{16}$ and $R^{18}$ are joined together by a $C_{2-3}$alkyl chain to form a 5-6 membered ring, where the alkyl are unsubstituted or substituted with 1-3 substituents where the substituents are independently selected from: halo, hydroxy, —$COR^{11}$, $C_{1-3}$alkyl, and $C_{1-3}$alkoxy,
or $R^{16}$ and $R^{18}$ are joined together by a $C_{1-2}$alkyl-O—$C_{1-2}$ alkyl chain to form a 6-8 membered ring, where the alkyl are unsubstituted or substituted with 1-3 substituents where the substituents are independently selected from: halo, hydroxy, —$COR^{11}$, $C_{1-3}$alkyl, and $C_{1-3}$alkoxy,
or $R^{16}$ and $R^{18}$ are joined together by a —O—$C_{1-2}$alkyl-O-chain to form a 6-7 membered ring, where the alkyl are unsubstituted or substituted with 1-3 substituents where the substituents are independently selected from: halo, hydroxy, —$COR^{11}$e, $C_{1-3}$alkyl, and $C_{1-3}$alkoxy;

n is selected from 0, 1 and 2;

the dashed line represents a single or a double bond; and pharmaceutically acceptable salts thereof and individual diastereomers thereof.

A further aspect of the compounds of the present invention include those of formula Ia:

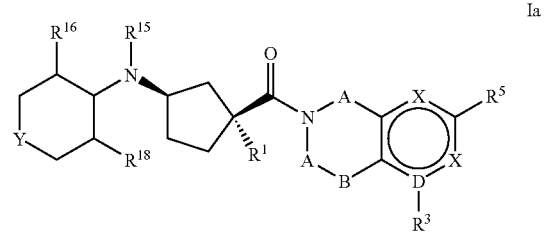

Ia wherein $R^1$, $R^3$, $R^5$, $R^{15}$, $R^{16}$, $R^{18}$, A, B, D, X, and Y are defined herein, and pharmaceutically acceptable salts and individual diastereomers thereof.

A still further aspect of the compounds of the present invention include those of formula Ib:

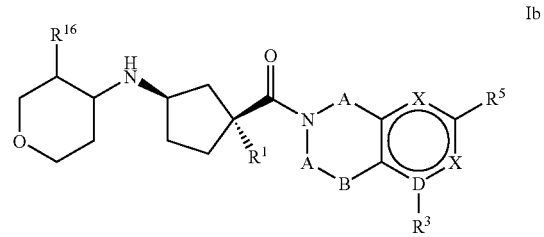

Ib wherein $R^1$, $R^3$, $R^5$, $R^{16}$, A, B, D, and X are defined herein, and pharmaceutically acceptable salts and individual diastereomers thereof.

Another aspect of the compounds of the present invention include those of formula Ic:

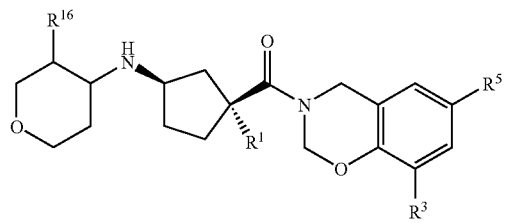

Ic wherein $R^1$, $R^3$, $R^5$ and $R^{16}$ are defined herein, and pharmaceutically acceptable salts and individual diastereomers thereof.

Another aspect of the compounds of the present invention also include those of formula Id:

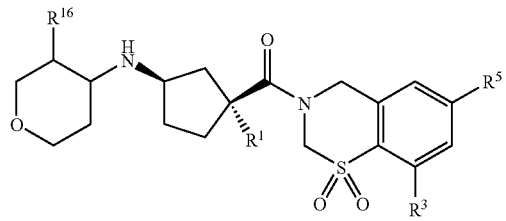

Id wherein $R^3$, $R^5$, and $R^{16}$ are defined herein and pharmaceutically acceptable salts and individual diastereomers thereof.

A still further aspect of the compounds of the present invention also include those of formula Ie:

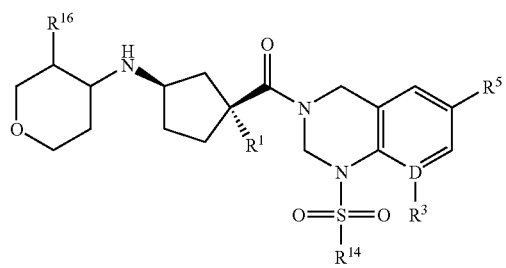

(Ie)

wherein $R^3$, $R^5$, $R^{16}$, and D are defined herein and pharmaceutically acceptable salts and individual diastereomers thereof.

Another aspect of the compounds of the present invention also include those of formula If:

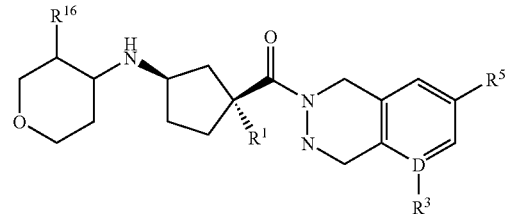

If wherein $R^3$, $R^5$, $R^{16}$, and D are defined herein and pharmaceutically acceptable salts and individual diastereomers thereof.

Another aspect of the compounds of the present invention also include those of formula Ig:

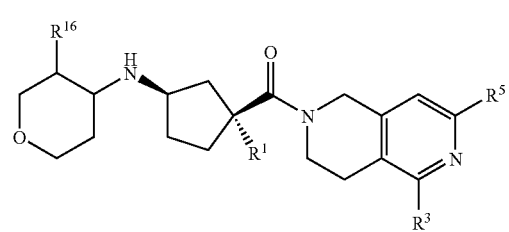

Ig wherein $R^3$, $R^5$, and $R^{16}$ are defined herein and pharmaceutically acceptable salts and individual diastereomers thereof.

Another aspect of the compounds of the present invention also include those of formula Ih:

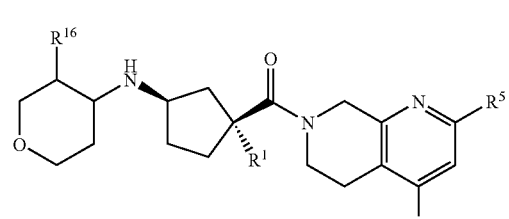

Ih wherein $R^3$, $R^5$, and $R^{16}$ are defined herein and pharmaceutically acceptable salts and individual diastereomers thereof.

In another aspect of the compounds of the present invention Y is selected from the group consisting of:
—O—, —CH$_2$—, —S—, —SO—, and —SO$_2$—.

In another aspect of the present invention $R^1$ is selected from:

(1) —$C_{1-6}$alkyl, which is unsubstituted or substituted with 1-6 substituents where the substituents are independently selected from:
  (a) halo,
  (b) hydroxy,
  (c) —O—$C_{1-3}$alkyl,
  (d) trifluoromethyl, and
  (e) —$COR^{11}$,
(2) —$C_{0-6}$alkyl-O—$C_{1-6}$alkyl-, which is unsubstituted or substituted with 1-6 substituents where the substituents are independently selected from:
  (a) halo,
  (b) trifluoromethyl, and
  (c) —$COR^{11}$,
(3) —($C_{3-5}$cycloalkyl)-($C_{0-6}$alkyl), which is unsubstituted or substituted with 1-7 substituents where the substituents are independently selected from:
  (a) halo,
  (b) hydroxy,
  (c) —O—$C_{1-3}$alkyl,
  (d) trifluoromethyl, and
  (e) —$COR^{11}$,
(4) phenyl or heterocycle which is unsubstituted or substituted with 1-3 substituents where the substituents are independently selected from:
  (a) halo,
  (b) hydroxy,
  (c) —O—$C_{1-3}$alkyl,
  (d) trifluoromethyl, and
  (e) —$COR^{11}$, In another aspect of the present invention $R^1$ is $C_{1-6}$alkyl which is unsubstituted or substituted with 1-5 substituents where the substituents are independently selected from:
  (a) hydroxy, and
  (b) fluoro.

In a still further aspect of the present invention $R^1$ is selected from:
  (a) isopropyl,
  (b) —$CH(OH)CH_3$, and
  (c) —$CH_2CF_3$.

In another aspect of the present invention when D is a nitrogen atom $R^3$ is absent, hydrogen, or oxygen.

In still another aspect of the present invention when D is a carbon atom $R^3$ is selected from:
  (a) hydrogen
  (b) halo
  (c) hydroxy
  (d) $C_{1-3}$alkyl, where the alkyl is unsubstituted or substituted with 1-6 substituents independently selected from: fluoro, and hydroxy,
  (e) —$COR^{11}$,
  (f) —$CONR^{12}R^{12}$,
  (g) -heterocycle,
  (h) —$NR^{12}$—$SO_2$—$NR^{12}R^{12}$,
  (i) —$NR^{12}$—$SO_2$—$R^{14}$,
  (j) —$SO_2$—$NR^{12}R^{12}$,
  (k) -nitro, and
  (l) —NR12R12;

In another aspect of the present invention when D is a nitrogen $R^3$ is absent or hydrogen.

In a still further aspect of the present invention when D is a carbon $R^3$ is selected from:
  (a) fluoro,
  (b) trifluoromethyl,
  (c) hydrogen;

In an additional aspect of the present invention when D is a nitrogen $R^3$ is absent.

In another aspect of the present invention when D is a carbon $R^3$ is selected from:
  (a) fluoro,
  (b) hydrogen;

In still another aspect of the present invention when X is a nitrogen $R^4$ is absent, hydrogen, or oxygen.

In still another aspect of the present invention when X is a nitrogen $R^4$ is absent.

In a further aspect of the present invention, when X is a carbon atom, $R^4$ is selected from:
  (a) hydrogen,
  (b) trifluoromethyl, and
  (c) halo.

In a still further aspect of the present invention, X is a carbon atom and $R^4$ is hydrogen.

In another aspect of the present invention $R^5$ is selected from:
  (a) $C_{1-3}$alkyl substituted with 1-6 fluoro,
  (b) chloro,
  (c) bromo,
  (d) —O-phenyl, which is unsubstituted or substituted with one or more substituents selected from the group consisting of: halo and trifluoromethyl,
  (e) phenyl, which is unsubstituted or substituted with one or more substituents selected from the group consisting of: halo and trifluoromethyl, and
  (f) —O—$C_{1-3}$alkyl substituted with 1-6 fluoro.

In a further aspect of the present invention $R^5$ is selected from:
  (a) trifluoromethyl,
  (b) trifluoromethoxy,
  (c) bromo, and
  (d) chloro.

In a still further aspect of the present invention $R^5$ is selected from trifluoromethyl and trifluoromethoxy.

In another aspect of the present invention $R^{15}$ is hydrogen or methyl.

In still another aspect of the present invention $R^{16}$ is selected from:
  (a) hydrogen,
  (b) $C_{1-3}$alkyl, which is unsubstituted or substituted with 1-6 fluoro,
  (c) —O—$C_{1-3}$alkyl, and
  (d) fluoro, and
  (e) hydroxy.

In a further aspect of the present invention $R^{16}$ is selected from:
  (a) hydrogen,
  (b) trifluoromethyl,
  (c) methyl,
  (d) methoxy,
  (e) ethoxy,
  (f) ethyl,
  (g) fluoro, and
  (h) hydroxy.

In a still further aspect of the present invention $R^{16}$ is selected from:
  (a) hydrogen,
  (b) methyl,
  (c) methoxy;

In another aspect of the present invention $R^{18}$ is selected from:
  (a) hydrogen,
  (b) methyl, and
  (c) methoxy;

In still another aspect of the present invention $R^{16}$ and $R^{18}$ are joined together by a —$CH_2CH_2$-chain or a —$CH_2CH_2CH_2$-chain to form a cyclopentyl ring or a cyclohexyl ring.

Representative compounds of the present invention include those presented in the Examples and pharmaceutically acceptable salts and individual diastereomers thereof.

The compounds of the instant invention have at least two asymmetric centers at the 1- and 3-positions of the cyclopentyl ring. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The configurations of one aspect of the compounds of this invention are where the substituents on the cyclopentyl ring (amide and amine units) are cis, as depicted:

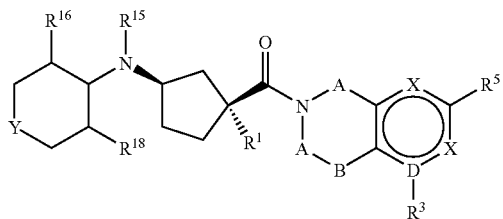

The absolute configurations of a further aspect of the compounds of this invention are those of the orientation as depicted:

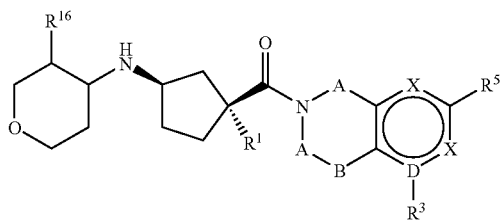

wherein the carbon bearing the amine substituent is designated as being of the (R) absolute configuration and the carbon bearing the amide subunit can be designated as being of either the (S) or (R) absolute configuration depending on the priority for $R^1$. For example if R is isopropyl then the absolute stereochemistry at the carbon bearing the amide subunit would be (S) since the amide and amine units are preferred to have the cis arrangement on the cyclopentyl ring.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., J. Exp. Med., 177, 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1 \times 10^7$ cells/ml. Cells were fluorescently labeled in the dark with 2 µM Calcien-AM (Molecular Probes), for 30 min at 37° C. Labeled cells were washed twice and suspended at $5 \times 10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a preferred embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (Trichuriasis, Enterobiasis, Ascariasis, Hookworm, Strongyloidiasis, Trichinosis, filariasis), trematodes (flukes) (Schistosomiasis, Clonorchiasis), cestodes (tape worms) (Echinococcosis, Taeniasis saginata, Cysticercosis), visceral worms, visceral larva migraines (e.g., Toxocara), eosinophilic gastroenteritis (e.g., *Anisaki* sp., *Phocanema* sp.), and cutaneous larva migraines (Ancylostona braziliense, Ancylostoma caninum). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds that modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a further aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/ prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as P2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, preferably 2.0 to 500, more preferably 3.0 to 200, particularly 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are either commercially available or made by known procedures in the literature or as illustrated. The present invention further provides processes for the preparation of compounds of the formula I as defined above, which comprises many different sequences of assembling compounds of formula (II), formula (III), and formula (IV), or compounds of formula (VI) and formula (IV), or compounds of formula (VI) and formula (V).

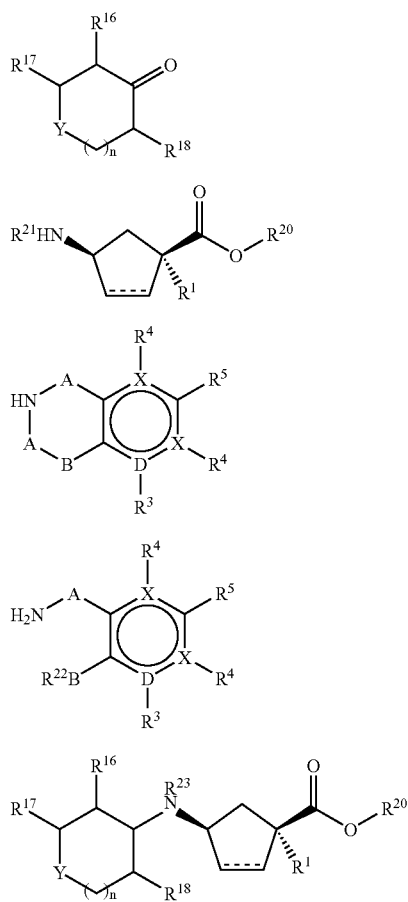

wherein $R^1$, $R^3$, $R^4$, $R^5$, $R^6$, $R^{16}$, $R^{17}$, $R^{18}$ A, B, C, D, and Y are defined as in formula I, and $R^{20}$ represents either a hydrogen or an alkyl group such as methyl, ethyl, t-butyl, or benzyl which serves as a protecting group, $R^{21}$ represent either hydrogen or an amine protecting group (Greene, T; Wuts, P. G. M. *Protective Groups in Organic Synthesis*, John Wiley & Sons, Inc., New York, N.Y. 1991) such as Boc or trifluoroacetate, $R^{22}$ represents either hydrogen or a protecting group such as t-butyl, or a group such as $-SO_2R^9$, $-CO_2R^9$, or $CONR^9R^9$, and $R^{23}$ represents a protecting group such as a trifluoroacetate. The bond between the two carbon atoms where a dashed line is shown in formula III and in formula VI represent either a single or double bond as defined in formula I.

One general way of constructing target compounds I utilizing Intermediates of the formulas II, III, and IV is illustrated in Scheme 1. Coupling of the acid IIIa and the amine IV under standard amide bond formation reaction conditions such as PyBrop in the presence of a base such as N,N-diisopropylethylamine and a catalyst such as DMAP gives the intermediate 1-1. Removal of the Boc protecting group yields the amine 1-2. Reductive alkylation of 1-2 with ketones II in the presence of a borohydride such as sodium triacetoxyborohydride or sodium cyanoborohydride then provides the compound of formula Ia. Note that when $R^{16}$, $R^{17}$, or $R^{18}$ are other than hydrogen, a mixture of diastereomers (Eliel, E. E., Wilen, S. H., *Stereochemistry of Organic Compounds*, John Wiley & Sons, Inc., New York) results from the reductive amination step. These can be separated into their components by chromatography using normal phase, reverse phase or chiral columns, depending on the nature of the separation. Compound Ia can be further elaborated to the compound of the formula I by reductive alkylation with an aldehyde or by alkylation with, for example, an alkyl halide.

SCHEME 1

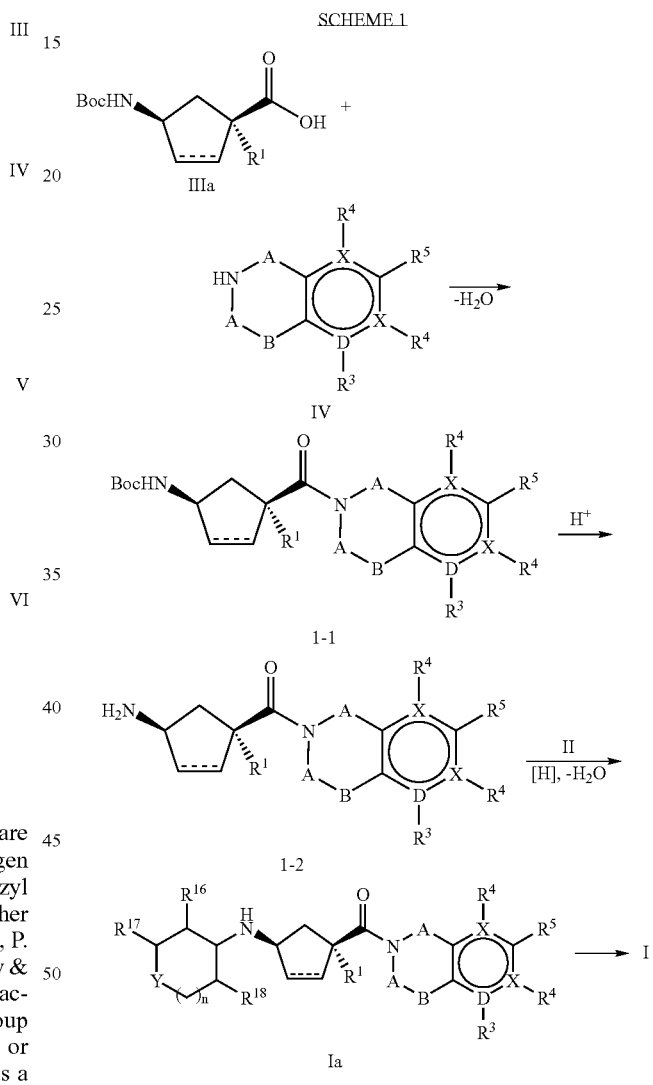

An alternative sequence of construction involving fragments of the formulas II, III, and IV is depicted in Scheme 1A. Amine IIIb is reductively alkylated with ketone II in the presence of a borohydride such as sodium triacetoxyborohydride or sodium cyanoborohydride to give secondary amine 1-3. Protection of the amine group can be accomplished using any of a number of protecting groups, including the trifluoroacetamide group ($R^{23}$=$COCF_3$), which can be installed by treatment with trifluoroacetic anhydride in the presence of a base such as triethylamine. The ester functionality of the resulting compound VI is then cleaved using conditions that are dependent upon the nature of $R^{20}$. For example, a benzyl ester is cleaved by hydrogenolysis using a catalyst such as Pd on carbon to give the fragment of the formula VIa. Coupling of the acid VIa and the amine IV under standard amide bond formation reaction conditions such as PyBrop in the presence of a base such as N,N-diisopropylethylamine and a catalyst such as DMAP gives the intermediate 1-4. Alternatively, the acid VIa can be converted to its corresponding acid chloride and then treated with amine IV in the presence of a base such as triethylamine to give 1-4. Removal of the protecting group ($R^{23}$) to give compound Ia can be achieved in various ways depending upon the nature of the protecting group. For example the trifluoroacetate group can be removed by treatment with excess sodium borohydride, or by treatment with a base such as lithium hydroxide.

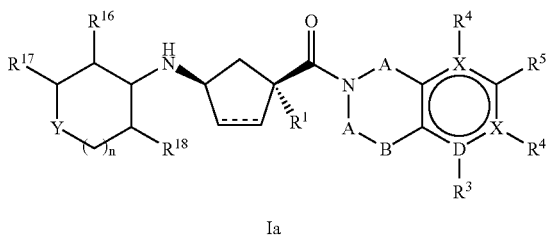

Ia

Alternatively, Intermediate 1-3 from Scheme 1A can be more directly accessed as shown in Scheme 1B. In this case amine IIIc is reductively alkylated with ketone II in the presence of a borohydride such as sodium triacetoxyborohydride or sodium cyanoborohydride to give secondary amine 1-3a. Treatment with a base such as LDA then generates the enolate of 1-3a which can be alkylated with a variety of electrophiles including but not limited to alkyl halides, aldehydes, ketones. The resulting compound 1-3 can be carried on to compounds of the formula I or Ia, using the same steps as outlined in Scheme 1A.

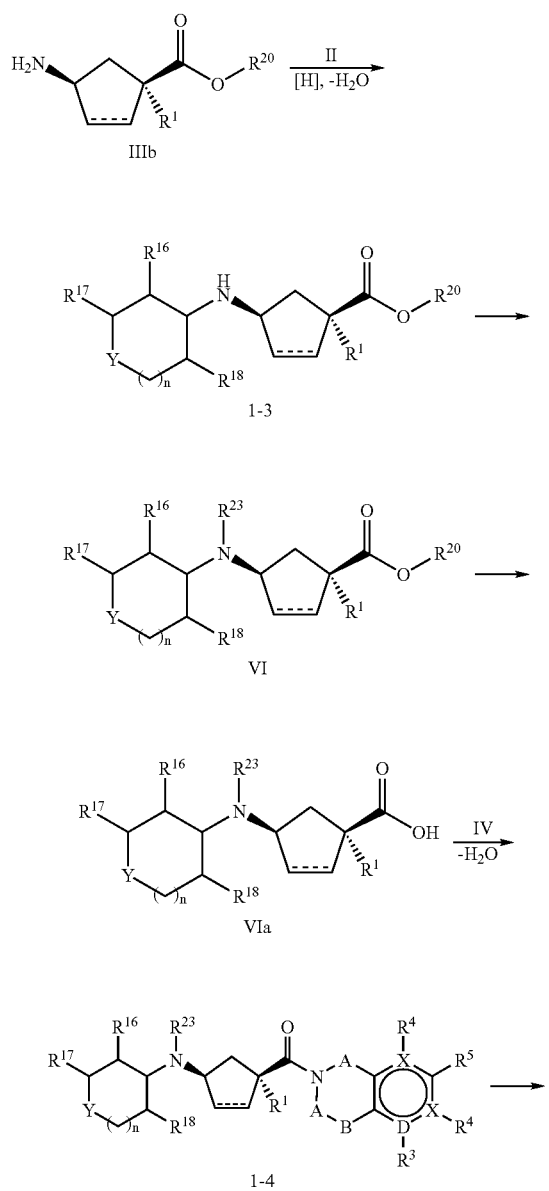

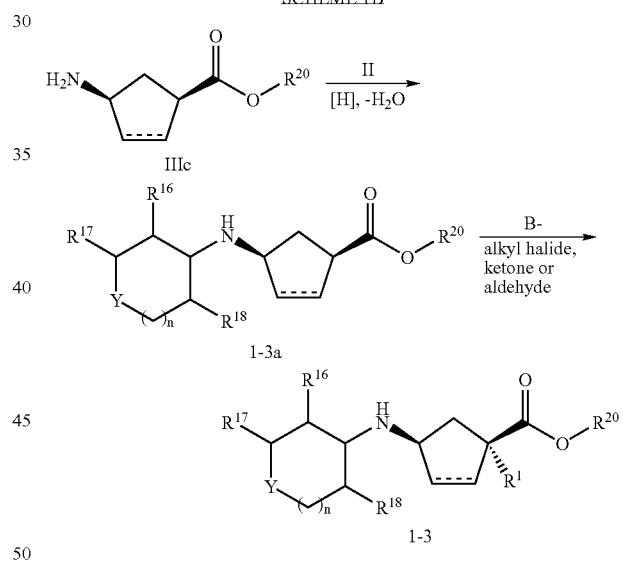

In addition to assembly according to Schemes 1, and 1A-1B, compounds of the formula I can be prepared using Intermediates of the formula V and VI (Scheme 2). According to this approach acids of the formula Via are coupled to primary amines V using EDC, or EDC and HOAt, or by first forming the acid chlorides with oxalyl chloride, among other methods. The resulting amides 2-1 are deprotected if B has a protecting group, $R^{22}$, for example if $BR^{22}$ is O-t-butyl, then TFA or HCl in dioxane may be used to remove the t-butyl group. After deprotection, or if no deprotection is required, treatment with paraformaldehyde (or another formaldehyde source) and an acid catalyst such as TsOH accomplishes cyclization to give intermediates 1-4 (Scheme 1A). Alternatively, 2-1 may be treated with phosgene to afford compounds 1-4. These then are converted as shown previously into final chemokine modulators.

SCHEME 2

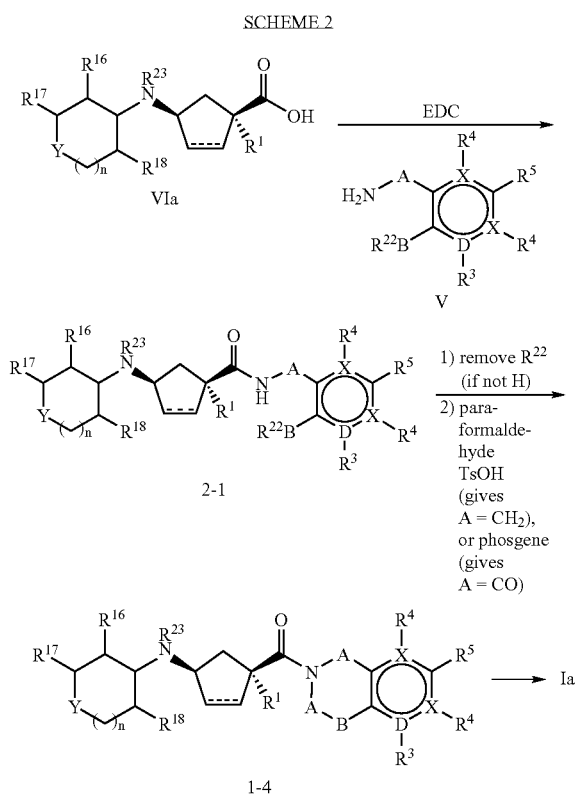

SCHEME 3

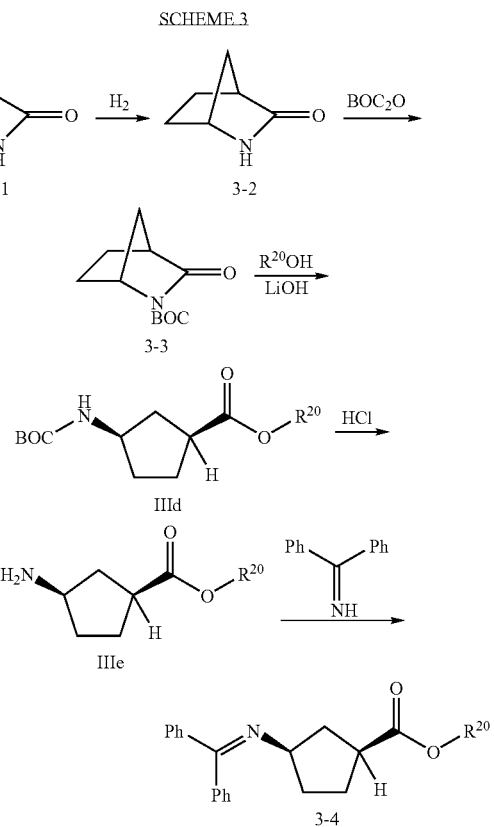

3-4 is formed, which can be obtained in pure form by simple filtration to remove ammonium chloride.

The cyclopentane core fragment III can be prepared in a number of ways. One of those is depicted in Schemes 3, 3a, and 3b. According to Scheme 3, the commercially available homochiral lactam 3-1 is hydrogenated and the saturated 3-2 is treated with di-tert-butyl dicarbonate in the presence of a suitable catalyst, e.g. N,N-dimethylamino pyridine. A base catalyzed cleavage of the amide bond in the presence of a suitable alcohol $R^{20}$—OH then provides the respective ester IIId. The BOC-protecting group is removed, preferably with an acid such as HCl in a aprotic solvent, such as dioxane, to yield the amine IIIe in the form of a salt. When this amine is mixed with benzophenone imine, the respective Schiff base The enolate formed from ester 3-4 with a strong base, such as LDA can be reacted with alkyl halides $R^1$-X, as well as aldehydes $R^{1a}$CHO or ketones $R^{1a}R^{2a}$CO to obtain intermediates 3-5, 3-6 and 3-7, 3-8, respectively (Scheme 3A). These reactions produce a mixture of the respective cis- (3-5 and 3-7) and trans- (3-6 and 3-8) diastereoisomers, be separated by a suitable chromatography. In most cases, normal phase flash chromatography on deactivated silica gel can be applied with success.

SCHEME 3A

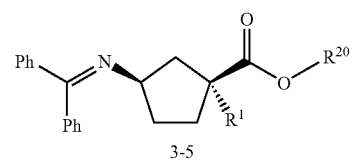

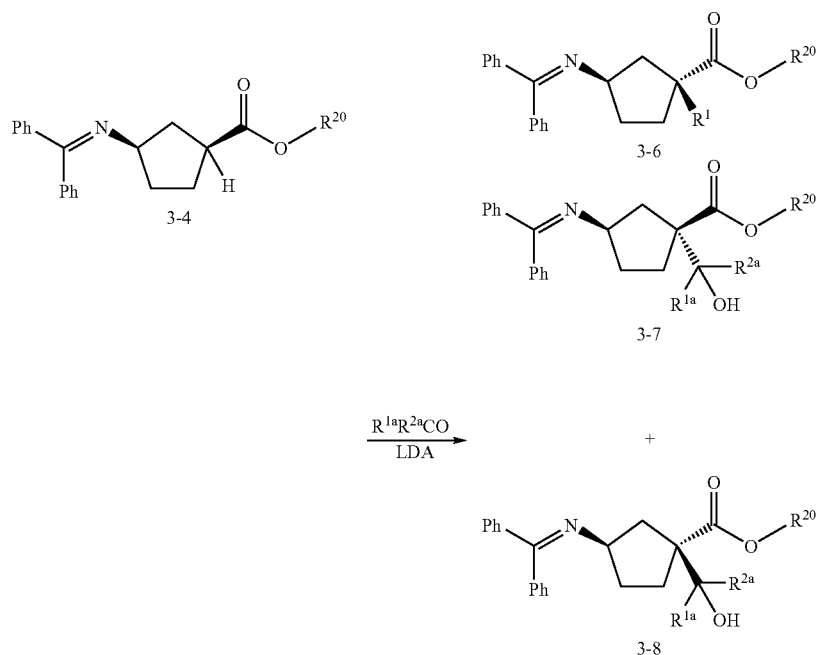

The desired cis diastereoisomers 3-5 and 3-7 are then treated with an acid such as HCl to aid hydrolysis of the imine group and the resulting amino group IIIf can be suitably protected e.g. in a form of a tert-butoxycarbonyl amide (Scheme 3B). The ester group present in intermediates IIIg can then be cleaved to give acid IIIh. The applied procedure depends on the nature of the ester: e.g. a benzyl ester can be cleaved by hydrogenolysis, a tert-butyl ester under acidic conditions and a alkyl ester can be hydrolyzed under either acidic or basic conditions.

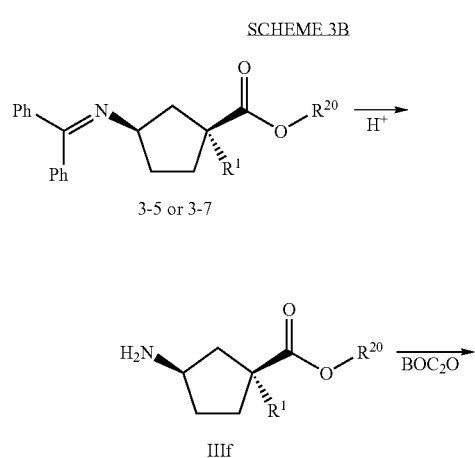

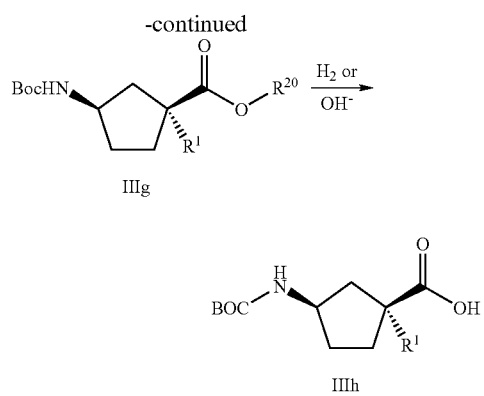

Note that Compound IIIh can be used in place of IIIa in Scheme 1, IIIf can be used in place of IIIb in Scheme 1A, and IIIe can be used in place of IIIc in Scheme 1B (the only differences being that the cyclopentane rings are defined as being fully saturated). An alternative way of preparing compounds of the type III is shown in Scheme 3C. According to this route, commercially available IIIi is converted to ester IIIj using an appropriate alcohol such as methyl or benzyl alcohol in the presence of an acid catalyst. Protection of the amine in IIIj by treatment with Boc$_2$O results in IIIk. Alkylation using a base such as lithium hexamethyldisilazide (LiHMDS) and an electrophile such as an alkyl halide gives IIIl, where the major diastereomer obtained is normally the cis-1,3-isomer. Separation of the cis/trans isomers can be carried out at this point or after the following step using column chromatography. If desired, hydrogenation using a catalysts such as Pd/C gives IIIm. If R$^{20}$ is benzyl, hydrogenation of IIIm would directly furnish IIIn. Otherwise, IIIm can be hydrolyzed using various conditions such as treatment with NaOH to give IIIn.

SCHEME 3C

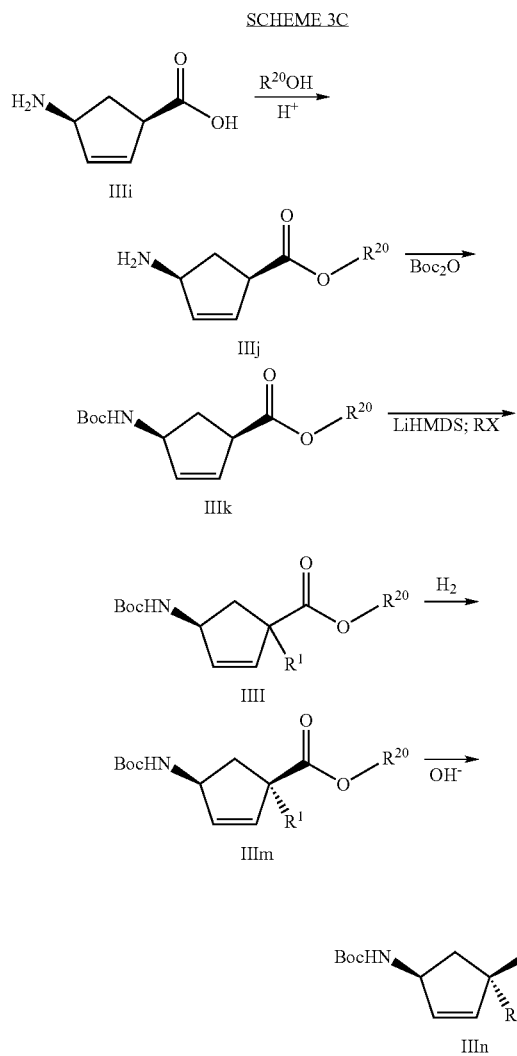

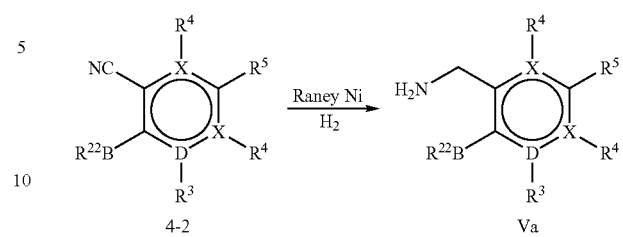

Amines of the type represented by formula IV were prepared on an individual basis and details for their preparation can be found in the Experimental section.

Compounds of the type represented by fragment II were often commercially available, but sometimes required preparation. For example, compounds IIa (Scheme 5) where X is either $CH_2$, S, O, or NP (P=protecting group), and $R^{17}$ and $R^{18}$ are both hydrogen, are commercially available. Compounds can be easily modified to IIb, having $R^{16}$ groups, where $R^{16}$ is an alkyl group, by deprotonation with a base such as LDA and alkylation with an alkyl halide (for a published procedure involving tetrahydropyran-4-one see *J. Am. Chem. Soc.*, 1991, 113, 2079-2089). Compounds IIb can be incorporated into final target compounds as shown in the preceding Schemes.

SCHEME 5

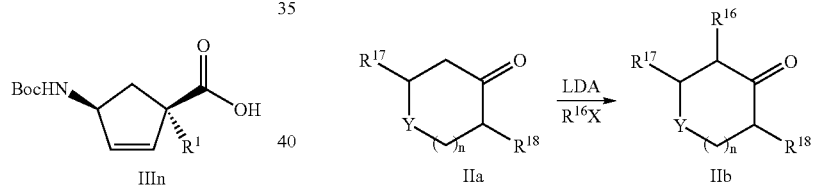

Amines of the formula V could be prepared in several ways. One approach is shown in Scheme 4. Fluorides 4-1 (either commercially available or prepared as detailed in the experimental section) could be treated with $R^{22}BH$ (such as ammonia, methanesulfonamide, t-butylthiol, t-butyl alcohol) in the presence of a base such as NaH to give 4-2 arising from nucleophilic aromatic substitution. The nitrile groups could then be reduced under various conditions, such as by Raney Ni and hydrogen gas or by borane, giving amines Va.

A synthesis of ketones IIc where $R^{16}$ is an alkoxy group is detailed in Scheme 5A. According to this, commercially available 5,6-dihydro-4-methoxy-2H-pyran (5-1) is treated with m-chloroperbenzoic acid in methanol to affect direct conversion to 5-2. An alkylation of the secondary alcohol with an appropriate alkyl halide $R^{25}X$ in a presence of a base such as sodium hydride affords the ether 5-3. Deprotection of the acetal under acidic conditions affords the desired ketones IIc. In this manner, a number of 3-alkoxyderivatives can be synthesized. Further details, as well as examples are described in the Experimental section.

SCHEME 4

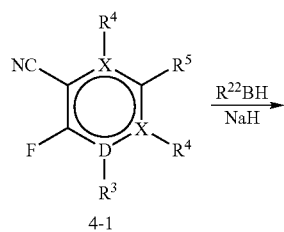

SCHEME 5A

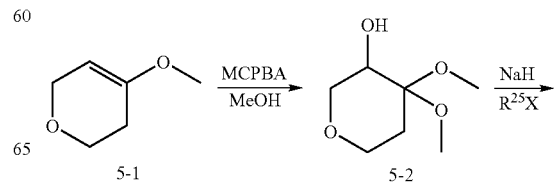

-continued

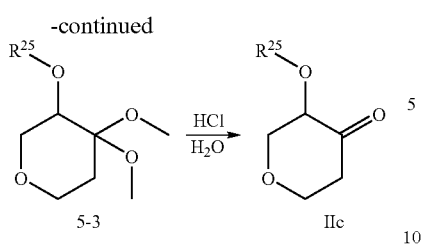

Alternatively, Intermediates 5-2 can be prepared in an asymmetric fashion according to Scheme 5C. Enol benzoate 5-4 can be prepared from ketone IId by trapping the enolate generated upon treatment with a base such as KHMDS with benzoic anhydride. Asymmetric oxidation can be accomplished according to the conditions described by Yian Shi, et al. (*J. Org. Chem.*, 2001, 66, 1818-1826) to give 5-6 as predominantly a single isomer. Ring opening of the epoxide and generation of the dimethyl acetal occurs in one pot by treatment with an acid such as CSA in methanol to give 5-2a. Either enantiomer of 5-2 could be obtained by appropriate choice of the sugar catalyst 5-5.

SCHEME 5B

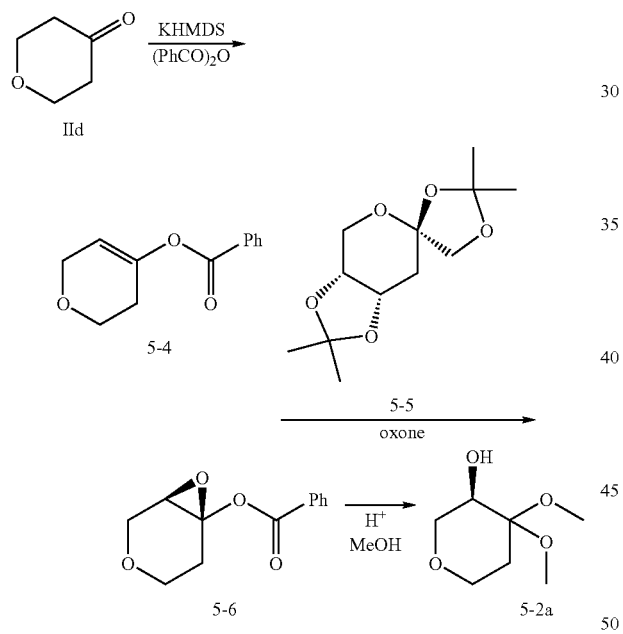

The following are representative procedures for the preparation of the compounds used in the following Examples or which can be substituted for the compounds used in the following Examples which may not be commercially available.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). MPLC refers to medium pressure liquid chromatography and was carried out on a silica gel stationary phase unless otherwise noted. NMR spectra were obtained in CDCl$_3$ solution unless otherwise noted. Coupling constants (J) are in hertz (Hz).

Abbreviations: diethyl ether (ether), triethylamine (TEA), N,N-diisopropylethylamine (DIEA) saturated aqueous (sat'd), room temperature (rt), hour(s) (h), minute(s) (min).

INTERMEDIATE 1

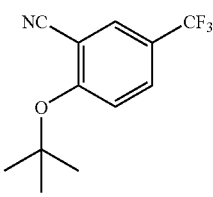

Step A:

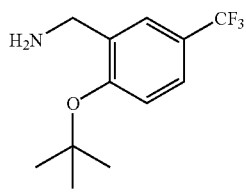

To a cooled (0° C.) solution of 2-fluoro-5-trifluoromethyl-benzonitrile (5.23 g, 27.7 mmol) in 140 mL of THF was added dropwise at a rapid pace a suspension of potassium t-butoxide (3.88 g, 34.6 mmol) in 35 ml of THF. The reaction mixture was permitted to slowly warm to room temperature and stir overnight. The reaction mixture was concentrated under reduced pressure then ether and 1 N HCl solution were added and the layers were separated. The ethereal layer was washed with saturated NaHCO$_3$ solution, then brine, dried over anhydrous MgSO$_4$, filtered, and concentrated. Purification by MPLC (silica, 25% ethyl acetate/hexane) afforded 5.25 g (78%) of a white crystalline solid.

H NMR (CDCl$_3$, 500 MHz): δ 7.84 (d, J=2.0 Hz, 1H), 7.73 (dd, J=8.5, 2.0 Hz, 1H), 7.27 (d, J=9.0 Hz), 1.55 (s, 9H).

Step B:

To a solution of the nitrile prepared as described in Step A (7.6 g, 31 mmol) in ethanol (100 mL) was added ammonium hydroxide solution (28-30%, 25 mL) and Raney® 2800 nickel (slurry in water, ~3.5 g). The resulting mixture was agitated under 50 psi of hydrogen gas for 24 h using a Parr apparatus. The reaction mixture was then filtered through celite washing with ethanol and then water. The filtrate was concentrated to dryness under reduced pressure and the residue so obtained was purified by flash chromatography [silica, 5 to 10% gradient (1% increments) of (10% ammonium hydroxide solution (28-30%)/methanol) in DCM] to afford 5.5 g (71%) of 1-[2-tert-butoxy-5-(trifluoromethyl)phenyl]methanamine as a colorless oil which crystallized upon storage in the freezer.

H NMR (CDCl$_3$, 500 MHz): δ 7.56 (d, J=2.0 Hz, 1H), 7.44 (dd, J=8.5, 2.0 Hz, 1H), 7.12 (d, 8.5 Hz, 1H), 3.90 (s, 2H), 2.70 (br s, 2H), 1.51 (s, 9H).

INTERMEDIATE 2

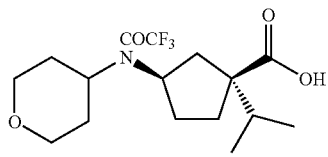

Procedure A

Step A:

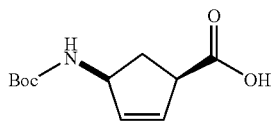

A mixture of (1R,4S)-4-amino-cyclopent-2-ene carboxylic acid (127 g, 1.0 mol), water (250 mL), sodium bicarbonate (168 g, 2.0 mol) and THF (750 mL) was stirred for 30 min, then solid Boc$_2$O (230 g, 1.05 mol) was added. The mixture was stirred over the weekend, filtered to remove insoluble material, and concentrated at 0° C. To the residue was added 2N aq. HCl (~500 mL) until the pH =3. The resulting precipitate was collected by filtration and washed with water, dried under vacuum overnight. The desired acid was obtained as a white solid (227 g, 100%).

$^1$H NMR (400 MHz, CD$_3$OD): 5.95 (m, 1H), 5.79 (m, 1H), 4.80 (br s, 1H), 3.45 (m, 1H), 2.50 (m, 1H), 1.79 (m, 1H), 1.44 (s, 9H).

Step B:

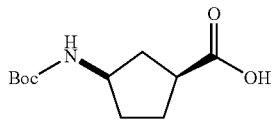

The acid (Step A, Procedure A, Intermediate 2) (227 g, 1.0 mol) and 10% Pd/C (5.0 g) in 500 mL of methanol on a Parr shaker was hydrogenated under 50 lb of hydrogen for one hour. The catalyst was removed by filtration and the filtrate was evaporated. The residue was dissolved in dichloromethane and dried over anhydrous sodium sulfate. After filtration, the filtrate was evaporated and dried under vacuum. The title compound was obtained as a light yellow solid (226.0 g, 99%). LC-MS for C11H19NO4[M$^+$H$^+$] calculated 230, found 230.

Step C:

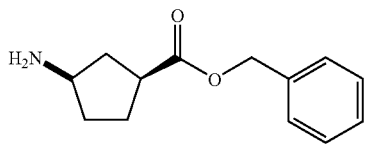

To a mechanically stirred solution of the acid (Step B, Procedure A, Intermediate 2) (226.0 g, 1.0 mol) in 500 mL of DMF was added solid potassium carbonate (210 g, 1.5 mol). The resulting mixture was stirred for 20 minutes, a neat benzyl bromide (118 mL, 1.0 mol) was added in one portion. An exothermic reaction was observed. After stirring for 3 h at RT, the entire mixture was transferred into an ice-water mixture (1000 mL). The crude product was extracted out with ether (2×800 mL). The combined ethereal layers were washed with water, dried over sodium sulfate, filtered and evaporated to give a yellow solid. This solid was combined with 4N HCl/dioxane (400 mL), stirred overnight and concentrated. The resulting solid was collected by filtration, washed with ether and dried in vacuum. The title product was obtained as HCl salt (140 g, 55%). $^1$H NMR (400 MHz, CD$_3$OD): 5.15 (s, 2H), 3.65 (m, 1H), 3.02 (q, J=8 Hz, 1H), 2.50 (m, 1H), 2.15 (m, 1H), 2.05 (m, 2H), 1.90 (m, 1H), 1.75 (m, 1H).

Step D:

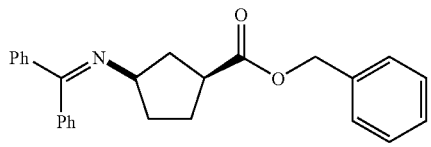

The amino benzyl ester HCl salt (Step C, Procedure A, Intermediate 2) (127 g, 0.5 mol) was suspended in 500 of dichloromethane. Benzophenone imine (91 g, 0.5 mol) was added. The resulting mixture was stirred overnight, filtered to remove the inorganic salt. The filtrate was washed with water and brine, dried over sodium sulfate, filtered, and concentrated. The residue was dissolved in 200 mL of toluene, evaporated. This procedure was repeated one time. Benzyl (1S,3R)-3-[(diphenylmethylene)amino]cyclopentanecarboxylate (178 g) was obtained as an brown oil which was used in next step without further purification. $^1$H NMR (400 MHz, CDCl$_3$): 1.80 (m, 1H), 1.95 (m, 2H), 2.15 (m, 2H), 2.50 (m, 1H), 2.89 (m, 1H), 3.61 (m, 1H), 5.20 (s, 2H), 7.18 (d, 2H), 7.38 (m, 8H), 7.47 (m, 3H), 7.64 (d, 2H).

Step E:

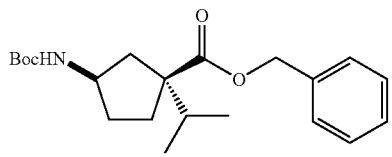

The starting Schiff base benzyl ester (Step D, Procedure A, Intermediate 2) (76.6 g, 200 mmol) in 300 mL of THF was cooled at −78° C. under a nitrogen atmosphere. While stirring, a solution of LDA in heptane (2.0 M, 110 mL, 220 mmol) was added over 20 minutes. The mixture was stirred for 30 minutes at −78° C., then a solution of 68 mL of isopropyl iodide (440 mmol) in 50 mL of THF was added, and the resulting mixture was stirred for 30 min. The reaction temperature was raised to 0° C. by removing the cooling bath. After stirred for 2 h, the entire mixture was evaporated to remove the THF. The residue was dissolved in ether (1000 mL), washed with water and brine, dried over sodium sulfate, and evaporated. The crude product was dissolved in 500 mL of THF, mixed with 400 mL of 1N HCl, stirred for one hour, and partially concentrated at 50° C. to remove the THF. The aq. solution was extracted with hexane (3×), made alkaline with sat. aq. sodium carbonate (pH>9), and combined with a solution of Boc₂O (53 g) in 500 mL of dichloromethane. The resulting mixture was stirred for 30 min. The organic phase was separated and the aq. phase was extracted with dichloromethane (3×). The combined organic phases were dried over sodium sulfate and evaporated. The residue was purified by flash chromatography (10% EtOAc/hexane) to yield the title compound as a mixture of cis and trans isomers (~1:1, 24 g). Further purification on MPLC (5% EtOAc/Hexane) afforded the pure cis isomer (faster eluting, 5.0 g) and trans isomer (slower eluting, 4.3 g). ESI-MS calc. for C21H31NO4:361; Found: 362 (M+H).

Step F:

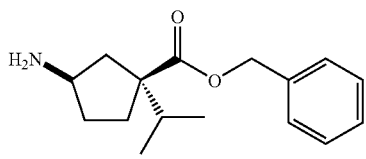

The above cis-Boc amino ester (1.25 g, 3.45 mmol) was stirred with 20 mL of 4N HCl/dioxane for one hour, evaporated and dried under high vacuum to yield benzyl (1S,3R)-3-amino-1-isopropylcyclopentanecarboxylate hydrochloride (1.05 g, 100%). ESI-MS calc. for C16H23NO2: 261; Found: 262 (M+H).

Step G:

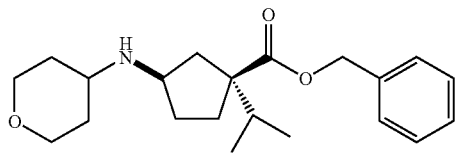

A mixture of the above amino ester (HCl salt, 1.05 g, 3.45 mmol), tetrahydro-4H-pyran-4-one (1.0 g, 10 mmol), molecular sieves (4 Å, 1.0 g), DIEA (0.78 g, 6 mmol) and sodium triacetoxyborihydride (1.33 g, 6 mmol) in 30 mL of dichloromethane was stirred overnight. The reaction was quenched with sat. aq. sodium carbonate, and filtered to remove insoluble material. The crude product was extracted into dichloromethane, dried over anhydrous sodium sulfate, concentrated and dried under high vacuum. The crude product was used in next step without further purification.

Step H:

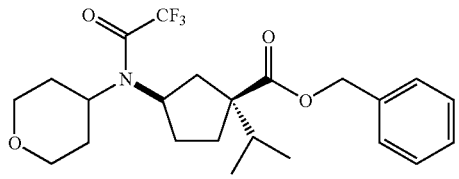

To a mixture of the crude amino ester (Step G, Procedure A, Intermediate 2) (6.85 g, 19.84 mmol), Et₃N (5.6 mL, 39.68 mmol), and DCM (50 mL), was slowly added TFAA (6.91 mL, 49.6 mmol). The reaction mixture was stirred at room temperature for 1 hour, then was washed with 1N HCl and brine, dried over anhydrous MgSO₄, and concentrated in vacuo. The crude product was purified by MPLC (20/80, EtOAc/Hexanes) to yield the title compound (3.7 g, 42%). LC-MS for C₂₃H₃₁F₃NO₄ [M⁺H⁺] calculated 442, found 442.

Step I:

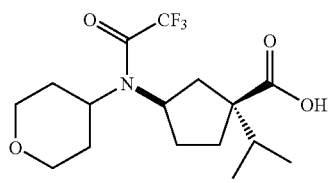

A mixture of the amide (Step H, Procedure A, Intermediate 2) (4.7 g, 10.7 mmol), 10% Pd/C (500 mg), and MeOH (50 mL) was stirred under a hydrogen balloon for 2 hours then was filtered through celite and concentrated in vacuo to yield the target acid (3.92 g, 99⁺%). LC-MS for C₁₆H₂₅F₃NO₄ [M⁺H⁺] calculated 352, found 352.

Procedure B

Step A:

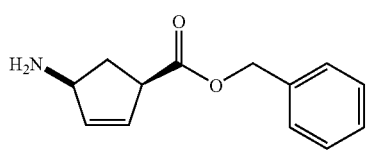

To a magnetically stirred solution of the Boc-amino acid (Step A, Procedure A, Intermediate 2) (159 g, 0.7 mol) in 500 mL of DMF was added solid potassium carbonate (138 g, 1.0 mol). The resulting mixture was stirred for 20 minutes, then neat benzyl bromide (84 mL, 0.7 mol) was added in one portion. An exothermic reaction was observed. After stirring overnight at RT, the entire mixture was transferred into an ice-water mixture (1000 mL). The crude product was extracted out with ethyl acetate (2×800 mL). The combined organic layers were washed with water, dried over sodium sulfate, filtered, and concentrated to offer a brown oil. This material was mixed with 4N HCl/dioxane (350 mL) and stirred until no more bubbles evolved. 500 mL of ether was added, the precipitate was collected by filtration and washed with ether and hexane. The desired product was obtained as HCl salt (164 g, 93%). ¹H NMR (400 MHz, CD₃OD): 7.38 (m, 5H), 6.25 (m, 1H), 5.94 (m, 1H), 5.20 (s, 2H), 4.32 (br s, 1H), 3.80 (br s, 1H), 2.67 (m, 1H), 2.14 (m, 1H).

Step B:

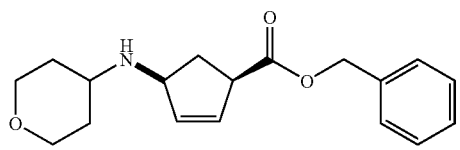

To a mixture of the amino ester HCl salt (Step A, Procedure B, Intermediate 2) (38 g, 150 mmol), tetrahydro-4-H-pyran-4-one (15 g, 150 mmol), DIEA (20.6 g, 160 mmol) and molecular sieves (4 Å, 20 g) in 200 mL of dichloromethane was added sodium triacetoxy borohydride (42.4 g, 200 mmol) in multiple portions. After complete addition, the mixture was stirred at RT overnight, quenched with sat. aq. sodium carbonate, and filtered through celite. The crude product was extracted into dichloromethane (3×), dried over sodium sulfate and concentrated. The residue was purified by flash chromatography (10%[aq. NH4OH/MeOH 1/9]/DCM). The desired fractions were combined and evaporated. The residue was mixed with THF and evaporated, redissolved in toluene and evaporated, dried in vacuum to yield a light brown oil (38 g, 84%). $^1$H NMR (400 MHz, CDCl$_3$): 7.38 (m, 5H), 5.98 (m, 1H), 5.85 (m, 1H), 3.98 (m, 3H), 3.54 (m, 1H), 3.40 (m, 2H), 2.82 (m, 1H), 2.44 (m, 1H), 1.90 (m, 1H), 1.79 (m, 2H), 1.70 (m, 1H), 1.44 (m, 2H).

Step C:

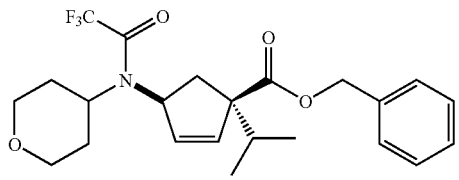

To a round flask containing solid potassium bis-(trimethylsilyl) amide (30 g, 151 mmol) under nitrogen was added 500 mL of anhydrous THF, cooled at −78° C. A solution of the amino ester (Step B, Procedure B, Intermediate 2) (38 g, 126 mmol) in 100 mL of THF was added over 20 minutes. The dry ice-acetone bath was changed into a dry ice-water bath (−15° C.). The mixture was stirred at −15° C. for one hour, then recooled to −78° C. Neat isopropyl iodide (65 mL, 378 mmol) was added. The flask was placed into the −15° C. dry ice/water bath again. After a few minutes, a large amount of white precipitate formed. The reaction mixture was stirred for additional one hour, poured into a mixture of ice and water, extracted with ether (3×). The combined ethereal layers were washed with water and brine, dried over sodium sulfate and concentrated. The residue was dissolved in dichloromethane, dried over sodium sulfate again and concnetrated. The residue was dried under vacuum, mixed with dichloromethane (200 mL) and cooled at to 0° C. under nitrogen. To the solution was added pyridine (33 mL, 400 mmol) and trifluoroacetic anhydride (27 mL, 190 mmol), dropwise. After one hour, the reaction was quenched with water. The organic phase was separated and washed with 2N aq. HCl, water and brine. After drying over sodium sulfate and concentrating, the resulting residue was purified by flash chromatogrphy (20% EtOAc/hexane) to yield a light brown oil (41 g, 74%). 1H-NMR showed a 5:1 mixture of cis/trans isomers. %). $^1$H NMR (400 MHz, CDCl$_3$): CH=CH: Cis: 6.06 (m, 1H), 5.68 (m, 1H), trans: 5.92 (m, 0.2 H), 5.79 (m, 0.2H). LC-MS for C23H28F3NO4 [M$^+$H$^+$] calculated 440, found 440.

Step D:

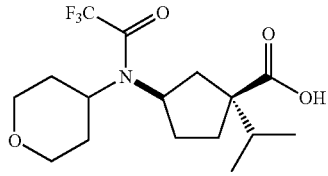

The unsaturated benzyl ester (Step C, Procedure B, Intermediate2) (41 g) and 10% Pd/C (2.0 g) in ethyl acetate (100 mL) was hydrogenated on a Parr shaker under 50 lb of hydrogen overnight. The catalyst was removed by filtration through a pad of celite. The filtrate was evaporated and the resulting residue was dissolved in dichloromethane, concentrated and dried under vacuum overnight. The desired acid was obtained as a gummy white solid (32.5 g, 100%). LC-MS for C16H24F3NO4 [M$^+$H$^+$] calculated 352, found 352.

INTERMEDIATE 3

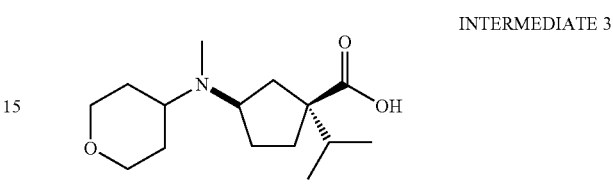

Step A:

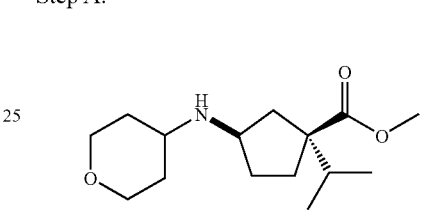

Methyl (1S,3R)-3-amino-1-isopropylcyclopentanecarboxylate hydrochloride (prepared in the same way as the intermediate from Step F, Procedure A, INTERMEDIATE 2, except with the modification that the methyl ester was employed instead of the benzyl ester, 1.4 g, 6.1 mmol) was combined with tetrahydro-4H-pyran-4-one (730 mg, 7.3 mmol), and triethylamine (1 mL, 7 mmol) in 50 mL of DCM. After 10 min, 4 Å powdered molecular sieves (1 g), and sodium triacetoxyborohydride (5.1 g, 24 mmol) were added and the resulting mixture was permitted to stir overnight. The reaction mixture was filtered through celite, and the filtrate was washed with saturated NaHCO$_3$ solution twice, then once with brine. The organic layer was dried over anhydrous MgSO$_4$, filtered, and concentrated to afford 1 g of methyl (1S,3R)-1-isopropyl-3-(tetrahydro-2H-pyran-4-ylamino)cyclopentanecarboxylate.

ESI-MS calc. for C15H27NO3: 269; Found: 270 (M+H).

Step B:

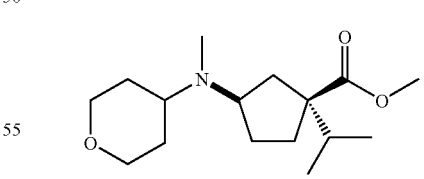

Methyl (1S,3R)-1-isopropyl-3-(tetrahydro-2H-pyran-4-ylamino)cyclopentanecarboxylate (1.0 g, 3.7 mmol) was combined with 37% aqueous formaldehyde solution (3.0 mL, 37 mmol) in 50 mL of DCM. After stirring for 35 min, 4 Å powdered molecular sieves, and sodium triacetoxyborohydride (3.9 g, 19 mmol) were added and the reaction mixture was stirred overnight under a nitrogen atmosphere. The reaction mixture was diluted with DCM, filtered through celite, and the filtrate was washed with saturated NaHCO$_3$ solution, and brine. The organic layer was dried over anhydrous MgSO$_4$, filtered, and concentrated to afford 1.0 g of methyl (1S,3R)-1-isopropyl-3-[methyl(tetrahydro-2H-pyran-4-yl)amino]cyclopentanecarboxylate.

ESI-MS calc. for C16H29NO3: 283; Found: 284 (M+H).

Step C:

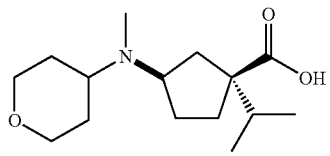

A solution of methyl (1S,3R)-1-isopropyl-3-[methyl(tetrahydro-2H-pyran-4-yl)amino]cyclopentanecarboxylate (1.0 g, 3.5 mmol) in 1:1 THF/MeOH (20 mL) was treated with a solution of LiOH.H$_2$O (735 mg) in 10 mL of water. After several hours very little hydrolysis was observed by HPLC-MS analysis so the reaction mixture was warmed to reflux and stirred for 2 days. The pH of the reaction mixture was then adjusted to 7 and the mixture was concentrated. The residue was suspended in 50% methanol/DCM, filtered, and the filtrate was concentrated to afford 900 mg of (1S,3R)-1-isopropyl-3-[methyl(tetrahydro-2H-pyran-4-yl)amino]cyclopentanecarboxylic acid which required no further purification.

ESI-MS calc. for C15H27NO3: 269; Found: 270 (M+H).

EXAMPLE 1

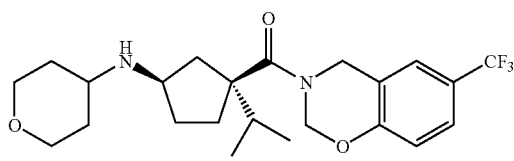

Step A:

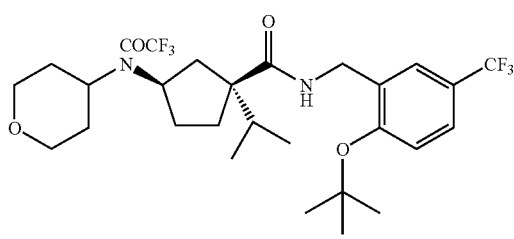

INTERMEDIATE 1 (259 mg, 1.05 mmol) was combined with INTERMEDIATE 2 (334 mg, 0.950 mmol) and EDC (364 mg, 1.90 mmol) in 10 mL of DCM. The reaction mixture was stirred at room temperature for 3 days, then was diluted with DCM and washed with water followed by brine, dried over anhydrous MgSO$_4$, filtered, and concentrated. Purification by MPLC (silica, 50% ethyl acetate/hexane) gave 320.2 mg (58%) of product.

ESI-MS calc. for C28H38F6N2O4: 580; Found: 581 (M+H).

Step B:

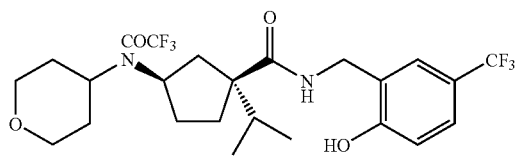

The intermediate amide prepared in Step A above (319 mg, 0.549 mmol) was dissolved in 4 N HCl/1,4-dioxane solution (7 mL) and stirred at room temperature for 2 h. The reaction mixture was concentrated to give 326 mg of product which was used without further purification.

ESI-MS calc. for C24H30F6N2O4: 524; Found: 525 (M+H).

Step C:

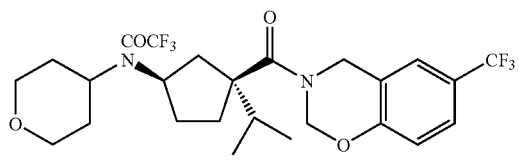

To a solution of the phenol prepared as described in Step B (108 mg, 0.206 mmol) in 6 mL of toluene was added paraformaldehyde (~50 mg) and TsOH.H$_2$O (4 mg, 0.02 mmol). The reaction vessel was fitted with a Dean Stark trap and a condenser and the resulting mixture was stirred at reflux for 3 h and at room temperature overnight. Since the reaction was incomplete more paraformaldehyde (~100 mg) and TsOH.H$_2$O (4 mg) was added and the reaction mixture was stirred at reflux for 4 h. The reaction mixture was then concentrated and the residue was purified by MPLC (silica, 55% ethyl acetate/hexane) to provide 61 mg of product.

ESI-MS calc. for C25H30F6N2O4: 536; Found: 537 (M+H).

Step D:

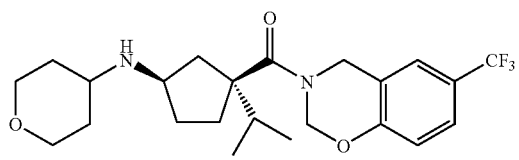

A solution of the cyclized product from Step C (58.2 mg, 0.108 mmol) in 1:1 THF/methanol (2 mL) was treated with a solution of LiOH.H$_{20}$ (14 mg, 0.33 mmol) in water (1 mL). The reaction mixture was stirred at 60° C. for 6 h. Since reaction was slow, more LiOH.H$_2$O (14 mg, 0.33 mmol) was added along with 1 mL each of THF, methanol, and water and the reaction mixture was stirred for another 12 h at 60° C. The reaction mixture was concentrated and purified by preparative TLC [silica, 7% of (10% ammonium hydroxide solution (28-30%)/methanol) in DCM]. The pure free base product was converted to its hydrochloride salt with 1 N HCl/ether (75 µL, 0.07 mmol) in 1 mL of DCM. Evaporation of the solvent afforded 32.5 mg of the target compound as a white solid.

ESI-MS calc. for C23H31F3N2O3: 440; Found: 441 (M+H).

INTERMEDIATE 4

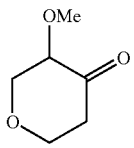

Step A:

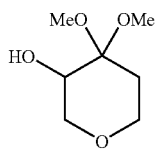

To a mixture of 5,6-dihydro-4-methoxy-2H-pyran (10.0 g, 87.5 mmol) in methanol (200 mL) at 0° C. was added dropwise a solution of 3-chloroperoxybenzoic acid (30.2 g, 175 mmol) in methanol (50 mL) via an addition funnel. The resulting solution was stirred for 5 h allowing it to slowly warm to room temperature. The methanol was removed under reduced pressure affording a white solid. The material was dissolved in 500 mL of dichloromethane and cooled to 0° C. To the mixture, while stirring vigorously, was added in portions an excess of solid calcium hydroxide (50-60 g). After stirring an additional 30 min, the mixture was filtered through a plug of celite and the filtrate was evaporated under reduced pressure to afford 11.62 g (82%) of the desired product as a clear oil. $^1$H NMR (500 MHz,CDCl$_3$) δ 3.88-3.80 (m, 2H), 3.73-3.68 (m, 2H), 3.54-3.48 (m, 1H), 3.28 (s, 3H), 3.27 (s, 3H), 2.00-1.93 (m, 1H), 1.82-1.77 (m, 1H).

Step B:

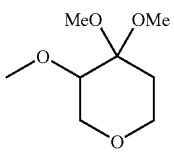

To a cooled (0° C.) solution of the product from Step A, Intermediate 4 (9.40 g, 58.0 mmol) in tetrahydrofuran (200 mL), under nitrogen, was slowly added NaH (2.32 g, 58.0 mmol) and the resulting slurry was stirred for 1 h at 0° C. Iodomethane (7.22 mL, 116 mmol) was then added via syringe to the slurry and the resulting mixture was stirred overnight allowing it to warm to room temperature. The reaction was quenched with a saturated solution of ammonium chloride (200 mL) and the organic layer was then removed using a separatory funnel. The aqueous layer was extracted with ether (3×150 mL) and all the organics were combined, dried over anhydrous sodium sulfate, filtered, and evaporated in vacuo. Purification was accomplished by flash column using a stepwise gradient eluant of 10-60% ether/hexanes to afford 8.46 g (83%) of the desired product as a clear oil. $^1$H NMR (500 MHz,CDCl$_3$) δ 3.98 (dd, J=2.5, 12.4 Hz, 1H), 3.77 (ddd, J=3.5, 7.1, 10.8 Hz, 1H), 3.57 (dd, J=1.4, 12.4 Hz, 1H), 3.50 (dd, J=2.5, 11.7 Hz, 1H), 3.46 (s, 3H), 3.25 (s, 3H), 3.22 (s, 3H), 3.22-3.20 (m, 1H), 1.96 (ddd, J=4.7, 11.8, 16.5 Hz, 1H), 1.75 (br dd, J=1.7, 14.2 Hz, 1H).

Step C:

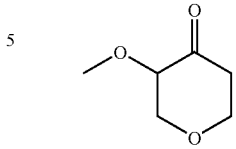

A solution of the product from Step B, Intermediate 4 (3.0 g, 17 mmol) in tetrahydrofuran/water (60 mL/10 mL) was treated with concentrated hydrochloric acid (6 mL) and the resulting solution was stirred at room temperature for 1 h. The mixture was concentrated in vacuo to remove the tetrahydrofuran and the aqueous layer then extracted with ether (6×50 mL). The organics were combined, dried over anhydrous sodium sulfate, filtered, and evaporated under reduced pressure to afford Intermediate 4 (1.75 g, 79%) as a clear oil. $^1$H NMR (500 MHz, CDCl$_3$) δ 4.23 (ddd, J=1.2, 11.4, 12.4 Hz, 1H), 4.15-4.09 (m, 1H), 3.82 (dd, J=5.95, 8.7 Hz, 1H), 3.74 (ddd, J=5.5, 8.5, 13.6 Hz, 1H), 3.56 (dd, J=8.8, 11.3 Hz, 1H), 3.50 (s, 3H), 2.61 (app dd, J=5.0,8.9 Hz, 2H).

INTERMEDIATE 5

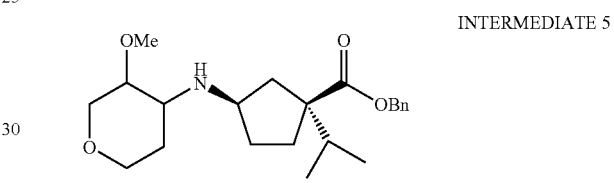

To a solution of benzyl (1S,3R)-3-amino-1-isopropylcyclopentanecarboxylate hydrochloride (Step F from procedure B of the preparation of INTERMEDIATE 2, 1.79 g, 6.01 mmol), INTERMEDIATE 4 (2.35 g, 18.0 mmol), and triethylamine (0.838 mL, 6.01 mmol) in 30 mL of DCM was added sodium triacetoxyborohydride (5.10 g, 24.0 mmol) and the resulting mixture was stirred for three days. The reaction mixture was diluted with DCM and washed with saturated NaHCO$_3$ solution, then brine, dried over anhydrous MgSO$_4$, filtered, and concentrated to give 2.61 g of crude product, which was primarily a mixture of two isomers (assumed from related work to be the two cis tetrahydropyran isomers). INTERMEDIATE 5 could be used crude as a mixture of two isomers or could be purified and separated into two single isomers (see INTERMEDIATES 5A and 5B) and then carried on.

ESI-MS calc. for C22H33NO4: 375; Found: 376 (M+H).

INTERMEDIATES 5A and 5B

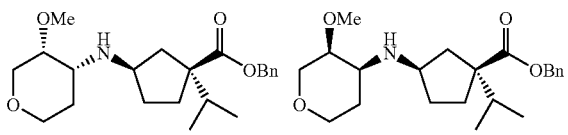

Crude INTERMEDIATE 5 (ca 6.01 mmol) was purified and separated into two major single isomers using a Chiralcel OD column (2 cm×25 cm, Daicel Chemical Industries), eluting with 20% i-propanol/heptane. This required 45 injections of approximately 50 mg of material/injection, and was performed in an automated fashion using a Gilson fraction collector integrated with Gilson Unipoint software. 920 mg Of the faster eluting isomer and 652 mg of the slower eluting isomer were obtained. The faster and slower eluting isomers are designated INTERMEDIATES 5A and 5B, respectively.

Faster eluting isomer (5A): ESI-MS calc. for C22H33NO4: 375; Found: 376 (M+H).

Slower eluting isomer (5B): ESI-MS calc. for C22H33NO4: 375; Found: 376 (M+H).

INTERMEDIATE 6

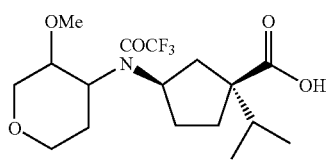

Step A:

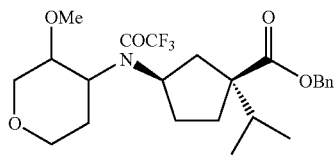

To a solution of unpurified INTERMEDIATE 5 (455 mg, 1.21 mmol) in DCM (10 mL) was added trifluoroacetic anhydride (257 µL, 1.82 mmol) followed by triethylamine (254 µL, 1.82 mmol). The reaction mixture was stirred at room temperature for 2.5 h, then was diluted with DCM and washed successively with 1 N HCl solution, saturated NaHCO₃ solution, and brine. The organic layer was dried over anhydrous MgSO₄, filtered, and concentrated to afford 554 mg of crude product. Purification by MPLC (silica, 40% ethyl acetate/hexane) provided 405 mg (71%) of product as a mixture of predominantly two isomers (two cis tetrahydropyran isomers).

ESI-MS calc. for C24H32F3NO5: 471; Found: 494 (M+Na⁺).

Step B:

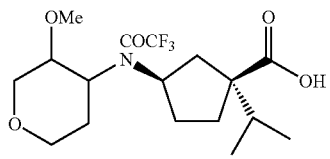

A mixture of ester from Step A above (405 mg, 0.859 mmol) and 10% Pd/C (Degussa, 80 mg) in methanol (5 mL) was stirred under a hydrogen atmosphere (balloon) for 2 h. The reaction mixture was filtered through a syringe equipped with a millipore PTFE 0.45 µm filter, and concentrated to give 310 mg of target acid as a mixture of predominantly two isomers (two cis tetrahydropyran isomers).

ESI-MS calc. for C17H26F3NO5: 381; Found: 404 (M+Na⁺).

INTERMEDIATES 6A AND 6B

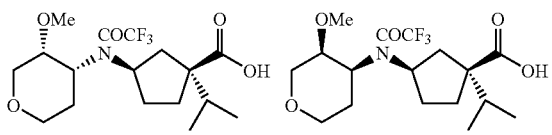

INTERMEDIATES 6A and 6B as single isomers were each individually prepared from INTERMEDIATES 5A and 5B respectively, using the same procedures as described for the synthesis of INTERMEDIATE 6. Note that the absolute stereochemistry of INTERMEDIATE 6A is one of the two shown immediately above and that of INTERMEDIATE 6B is the other, though which is which has not been unequivocally determined.

INTERMEDIATE 6A: ESI-MS calc. for C17H26F3NO5: 381; Found: 382 (M+H).

INTERMEDIATE 6B: ESI-MS calc. for C17H26F3NO5: 381; Found: 382 (M+H).

EXAMPLES 2A AND 2B

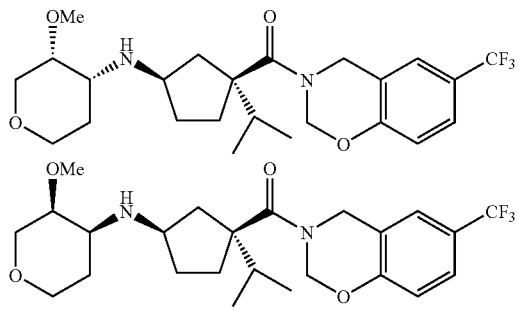

EXAMPLES 2A and 2B were prepared from INTERMEDIATES 6A and 1 and INTERMEDIATES 6B and 1, respectively, in a nearly identical fashion to that shown for the preparation of EXAMPLE 1. One difference was in the final deprotection Step as shown for EXAMPLE 2A below:

S,S or R,R

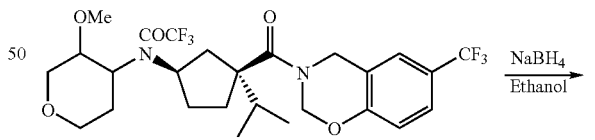

S,S or R,R

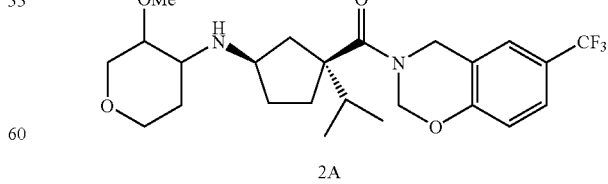

2A

The trifluoroacetate protected precursor shown above (100 mg, 0.177 mmol) was dissolved in 3 mL of ethanol and treated with NaBH4 (67 mg, 1.8 mmol). The resulting reaction mixture was stirred at room temperature for overnight then was concentrated. The residue was dissolved in DCM and washed with saturated NaHCO₃ solution, then brine, dried over anhydrous MgSO₄, filtered, and concentrated. Purification by reverse phase HPLC (YMC Pack Pro C18, 100×20 mm ID) afforded the product as its TFA salt. This was converted to its HCl salt by dissolving in DCM and adding ~175 µL of 1 N HCl/ether, then concentrating, giving 54 mg of product as a single stereoisomer. This same process was carried out to make EXAMPLE 2B.

EXAMPLE 2A: ESI-MS calc. for C24H33F3N2O4: 470; Found: 471 (M+H).

EXAMPLE 2B: ESI-MS calc. for C24H33F3N2O4: 470; Found: 471 (M+H).

EXAMPLE 3

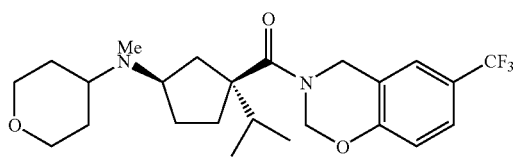

To a solution of the final product from EXAMPLE 1 (26 mg, 0.051 mmol), formaldehyde (37% w/v in water, 40 µL), and triethylamine (7 µL) in 1 mL of DCM was added 4° A sieves (powdered, 50 mg) followed by sodium triacetoxyborohydride (53 mg, 0.25 mmol). The reaction mixture was stirred at room temperature for 1 h, then was filtered through celite. The filtrate was washed with saturated NaHCO₃ solution, then brine, dried over anhydrous MgSO₄, filtered, and concentrated. The resulting free base was dissolved in DCM, treated with 12.5 µL of 4 N HCl in dioxane, and concentrated to afford 15 mg of the product as its hydrochloride salt.

ESI-MS calc. for C24H33F3N2O3: 454; Found: 455 (M+H).

INTERMEDIATE 7

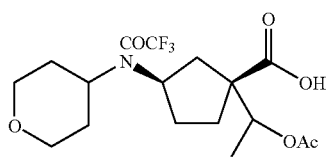

Step A:

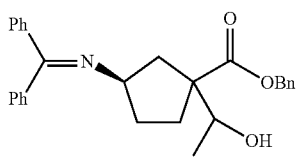

To a precooled (−78° C.) solution of LDA (1.5 M in cyclohexane, 63.3 mL, 94.9 mmol) in 95 mL of THF was added dropwise a solution of benzyl (1S,3R)-3-[(diphenylmethylene)amino]cyclopentanecarboxylate (Step D, procedure A of the preparation of Intermediate 2, 28 g, 73 mmol) in 45 mL of THF. After stirring the reaction mixture at −78° C. for 1 h 10 min, neat acetaldehyde (8.16 mL, 146 mmol) was added dropwise (accompanied by a color change from orange to yellow). After stirring for an additional 30 min, the cold reaction mixture was poured into 400 mL of 10% citric acid solution. The mixture was extracted twice with ether (400 mL) and the ethereal layers were combined and washed with brine, dried over anhydrous Na₂SO₄, filtered, and concentrated to give 22.5 g of crude product. Purification in 4 five g batches by MPLC (silica, eluting with 1 L 20% ethyl acetate/hexane, then 500 mL 25% ethyl acetate/hexane, then 1 L 30% ethyl acetate/hexane) allowed separation of a top and bottom band. The top band (6.48 g) was found to contain three of the four stereoisomers and the bottom band contained a single isomer, which was determined to have the undesired trans cyclopentyl stereochemistry.

Step B:

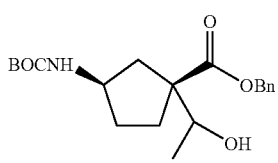

To a solution of the iminoester from Step A (6.48 g, 15.2 mmol) in 80 mL of THF was added 2 N HCl solution (40 mL) and the reaction mixture was stirred overnight at room temperature. Added more 2 N HCl solution (30 mL) and washed twice with hexane to remove the benzophenone. The aqueous layer was concentrated. To the residue was added 100 mL each of DCM and saturated NaHCO₃ solution. Then di-tert-butyl dicarbonate (6.63 g, 30.4 mmol) was added and the reaction mixture was stirred for 1.25 h. The layers were separated and the organic layer was washed with brine, dried over anhydrous MgSO₄, filtered, and concentrated to give 8.8 g of crude material. Purification by MPLC (silica, 50% ethyl acetate/hexane) allowed separation of two product bands, the top of which (1.76 g) corresponding to a single trans isomer and the bottom (2.90 g) corresponding to a mixture of two cis isomers epimeric at the hydroxyl center.

Step C:

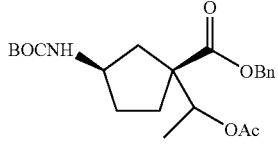

The hydroxy ester prepared as described in Step B (2.66 g, 7.32 mmol) was combined with triethylamine (2.55 mL, 18.3 mmol) and acetic anhydride (1.73 mL, 18.3 mmol) in 50 mL of DCM. The reaction mixture was stirred at room temperature for 2 h. The reaction mixture was then diluted with DCM and washed with 2 N HCl solution, saturated NaHCO₃ solution, and brine, dried over anhydrous MgSO₄, filtered, and concentrated. Purification by MPLC (silica, 45% ethyl acetate/hexane) gave 2.84 g of desired product.

Step D:

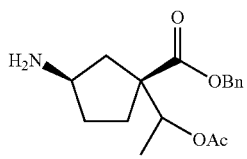

The intermediate from Step C (2.66 g, 6.56 mmol) was dissolved in 4 N HCl/1,4-dioxane (20 mL) and stirred at room temperature for 1.5 h. The reaction mixture was concentrated to afford 2.35 g of crude product as its hydrochloride salt which gave a single peak (>99%) on HPLC and was not further purified.

ESI-MS calc. for C17H23NO4: 305; Found: 306 (M+H).

Step E:

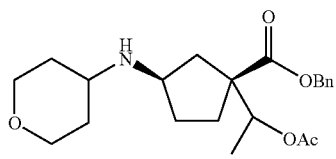

To a solution of the amine hydrochloride from Step D (1.83 g, 5.34 mmol), tetrahydro-4H-pyran-4-one (0.74 mL, 8.0 mmol), and triethylamine (0.74 mL, 5.3 mmol) in DCM was added sodium triacetoxyborohydride (4.53 g, 21.4 mmol). The resulting mixture was stirred overnight at room temperature. The reaction mixture was diluted with DCM and washed with saturated NaHCO₃ solution, then brine, dried over anhydrous MgSO₄, filtered, and concentrated to give 2.19 g of crude product which showed one major peak (>90%) by HPLC.

ESI-MS calc. for C22H31NO5: 389; Found: 390 (M+H).

Step F:

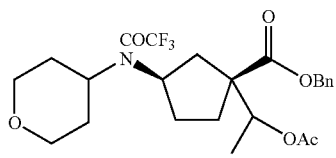

To a solution of the product from Step E (2.19 g, 5.62 mmol) and triethylamine (1.17 mL, 8.43 mmol) in 50 mL of DCM was added trifluoroacetic anhydride (1.19 mL, 8.43 mmol). The resulting reaction mixture was stirred at room temperature for 4 h. The mixture was diluted with DCM and washed with saturated NaHCO₃ solution, then brine, dried over anhydrous MgSO₄, filtered, and concentrated to give 2.28 g of crude product. Purification by MPLC (silica, 50% ethyl acetate/hexane) provided 2.07 of the protected amine.

ESI-MS calc. for C24H30F3NO6: 485; Found: 486 (M+H).

Step G:

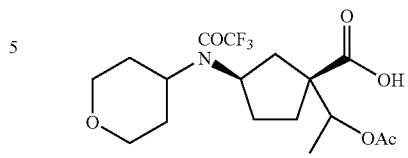

A mixture of the protected amine from Step F (2.07 g, 4.26 mmol) and 10% Pd?C (Degussa, 250 mg) in 30 mL of methanol was stirred under a hydrogen atmosphere using a balloon for 2 h and 10 min. The reaction mixture was filtered through celite and concentrated to give 1.56 g of the crude product (Intermediate 7) which showed a single peak by HPLC (>99%).

ESI-MS calc. for C17H24F3NO6: 395; Found: 396 (M+H).

EXAMPLES 4A AND 4B

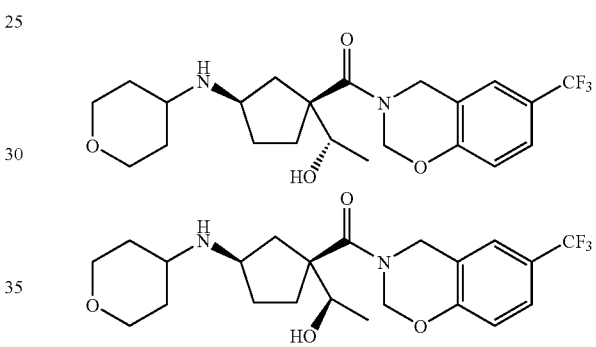

Step A:

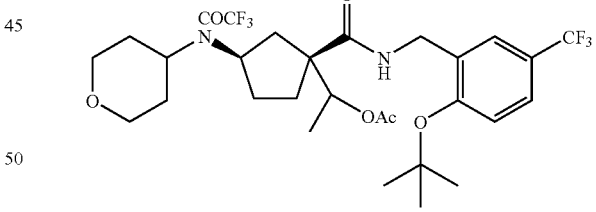

INTERMEDIATE 7 (102 mg, 0.257 mmol) and INTERMEDIATE 1 (95.3 mg, 0.386 mmol) in 5 mL of DCM were treated with EDC (98.5 mg, 0.514 mmol) followed by DMAP (~10 mg). The reaction mixture was stirred at room temperature for 4 h. The reaction mixture was diluted with DCM and washed with saturated NaHCO₃ solution, then brine, dried over anhydrous MgSO₄, filtered, and concentrated. HPLC-MS analysis suggested that a significant amount of the trifluoroacetamide protecting group may have been cleaved so the crude reside was dissolved in DCM and trifluoroacetic anhydride (36 μL) and triethylamine (36 μL) were added. This mixture was stirred at room temperature over 3 days, however the HPLC-MS did not shown any improvement so the mixture was diluted with DCM and washed with 2 N HCl, then brine, dried over anhydrous MgSO$_4$, filtered, and concentrated to give 188 mg of material which was used directly in the next step.

Step B:

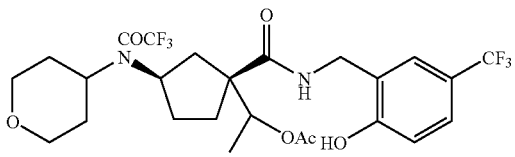

The crude product from Step A (ca 0.257 mmol) was dissolved in 3 mL of TFA. One drop of water was added and the mixture was stirred in a nitrogen atmosphere at room temperature for 3 h. The reaction mixture was concentrated and the resulting residue was purified by MPLC (silica, 50% ethyl acetate/hexane) to give 64.4 mg of the desired phenol.

ESI-MS calc. for C25H30F6N2O6: 568; Found: 569 (M+H).

Step C:

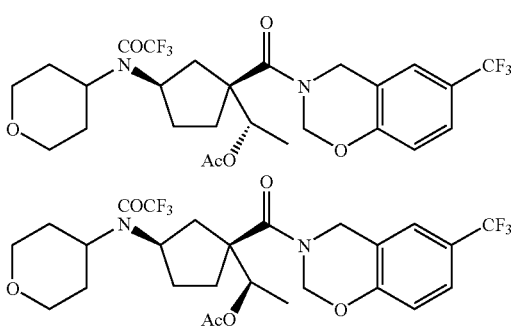

The phenol from Step B (64.4 mg, 0.113 mmol) was combined with paraformaldehyde (~1 50 mg) and TsOH.H$_{20}$ (~5 mg) in 8 mL of benzene. The reaction vessel was equipped with a Dean Stark trap and condenser and the reaction mixture was stirred at reflux for 1.5 h, whereupon no starting material remained according to HPLC-MS analysis. The reaction mixture was concentrated then redissolved in DCM and filtered. The filtrate was concentrated and the resulting residue was purified by preparative TLC (silica, 40% ethyl acetate/hexane) allowing separation of two product bands (top band 22.6 mg, bottom band 16.8 mg) corresponding to the two product diastereomers which are epimeric at the hydroxyl bearing carbon.

Faster eluting isomer: ESI-MS calc. for C26H30F6N2O6: 580; Found: 603 (M+Na$^+$).

Slower eluting isomer: ESI-MS calc. for C26H30F6N2O6: 580; Found: 603 (M+Na$^+$).

Step D:

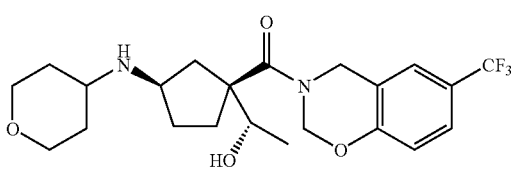

-continued

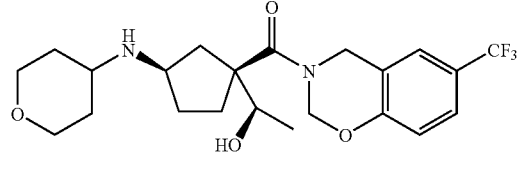

The faster eluting isomer obtained as described in Step C (22.6 mg, 0.0389) was dissolved in 3 mL of ethanol and treated with sodium borohydride (23 mg, 0.61 mmol). The resulting mixture was stirred at room temperature for overnight, then concentrated. Purification by preparative TLC [silica, 12% of (10% ammonium hydroxide solution (28-30%)/methanol) in DCM) gave the product which was converted to its hydrochloride salt by dissolving in DCM, adding 26 μL of 1 N HCl in ether, then concentrating to give 12 mg of salt.

The slower eluting isomer obtained as described in Step C (16.8; mg, 0.0289 mmol) was similarly fully deprotected and converted to its salt (7.4 mg).

From faster eluting isomer: ESI-MS calc. for C26H30F6N2O6: 580; Found: 603 (M+Na$^+$).

From slower eluting isomer: ESI-MS calc. for C26H30F6N2O6: 580; Found: 603 (M+Na$^+$).

INTERMEDIATE 8

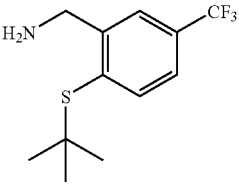

Step A:

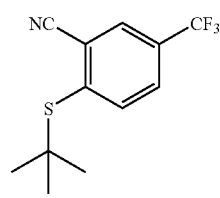

To a cooled (0° C.) solution of tert-butythiol (2.89 ml, 25.7 mmol) and 2-fluoro-5-(trifluoromethyl)benzonitrile (4.62 g, 24.4 mmol) in 100 mL of THF was added in small portions sodium hydride (60% dispersion in mineral oil, 1.12 g, 28.1 mmol). The reaction mixture was then permitted to warm slowly to room temperature under a nitrogen atmosphere and stir overnight. The reaction mixture was poured into water and extracted twice with ether. The combined ethereal layers were washed with brine, dried over anhydrous MgSO$_4$, filtered, and concentrated to give 6.82 g of crude product.

H NMR (CDCl$_3$, 500 MHz): δ 7.98 (br s, 1H), 7.85 (d, J=8.5 Hz, 1H), 7.80 (dd, J=8.5 Hz, 2 Hz, 1H), 1.42 (s, 9H).

Step B:

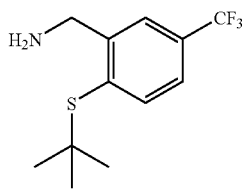

To a cooled (0° C.) solution of the nitrile prepared as described in Step A (6.36 g, 24.5 mmol) in 100 mL of THF was added dropwise a solution of BH$_3$THF in THF (1.0 M, 73.5 mL, 73.5 mmol). The reaction mixture was warmed to room temperature and stirred for 48 h, then was quenched by dropwise addition of methanol until gas evolution had ceased. The reaction mixture was concentrated then redissolved in 60 mL of methanol. A solution of anhydrous HCl in methanol (prepared by adding 2.92 mL of thionyl chloride to 95 mL of methanol) was added and the reaction mixture was stirred at room temperature for 3 days. The reaction mixture was concentrated and the residue was purified by flash chromatography (silica, 5-10% gradient of [10% ammonium hydroxide solution (28-30%)/methanol] in DCM) to afford 5.27 g of desired amine.

ESI-MS calc. for C12H16F3NS: 263; Found: 264 (M+H).

INTERMEDIATE 9

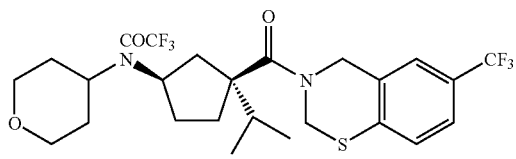

Step A:

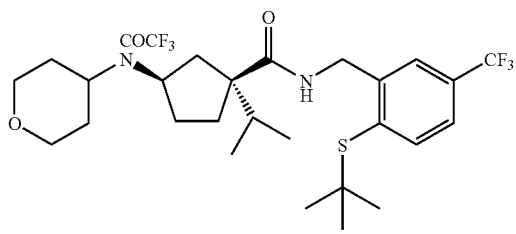

INTERMEDIATE 2 (112 mg, 0.319 mmol), INTERMEDIATE 9 (126 mg, 0.479 mmol), and EDC (122 mg, 0.638 mmol) were combined in 4 mL of DCM. DMAP (~5 mg) was added and the reaction mixture was permitted to stir at room temperature for 4 h. The mixture was diluted with DCM and washed with water, then brine, dried over anhydrous MgSO$_4$, filtered, and concentrated. Purification by MPLC (silca, 50% ethyl acetate/hexane) afforded 127 mg of product.

ESI-MS calc. for C28H38F6N2O3S: 596; Found: 597 (M+H).

Step B:

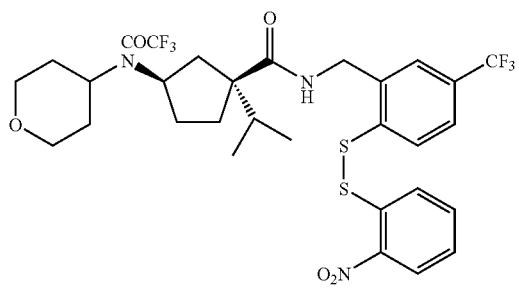

A solution of the product from Step A (127 mg, 0.213 mmol) in 3 mL of AcOH was treated with 2-nitrobenzenesulfenyl chloride (40 mg, 0.21 mmol) and the resulting mixture was stirred at room temperature for overnight. The reaction mixture was concentrated and used as is in the Step C.

ESI-MS calc. for C30H33F6N3O5S2: 693; Found: 694 (M+H).

Step C:

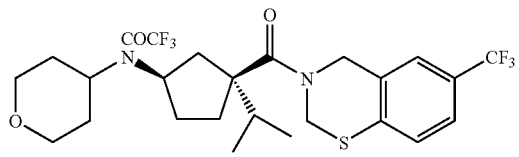

A solution of the crude product from Step B (ca 0.213 mmol) in methanol (~3 mL) was treated with sodium borohydride (4 mg). After stirring for 2 h at room temperature more sodium borohydride (4 mg) was added, then again a third time after 2 additional h. After 5 more min of stirring, the reaction mixture was filtered and concentrated. The residue was dissolved in benzene (8 mL) and sodium borohydride (5 mg) was added. After stirring for 5 min, paraformaldehyde (~100 Mg) and TsOH.H$_2$ (~25 mg) was added and the reaction mixture was stirred for 9 h under nitrogen at reflux in a reaction vessel equipped with a Dean Stark trap. The reaction mixture was then stirred at room temperature over night, and concentrated. HPLC-MS analysis indicated that little desired product was present and disulfide products (and starting material) predominated. This crude material was submitted to preparative TLC (silica, 30% ethyl acetate/hexane). A small amount of product was obtained along with three bands corresponding to disulfides and thiol. These latter three bands were combined, dissolved in ethanol (3 mL), cooled to 0° C., and treated with sodium borohydride (10 mg). This mixture was stirred under a nitrogen atmosphere for 10 min (HPLC-MS now showed only a single peak for the desired thiol intermediate). 3 N HCl solution was added to quench the remaining sodium borohydride and the mixture was concentrated to dryness, taking care to avoid exposure to air. The residue was dissolved in deoxygenated benzene (8 mL) and paraformaldehyde (100 mg) and TsOH.H$_2$O (5 mg) were added. The reaction mixture was stirred under nitrogen at reflux in a reaction vessel equipped with a Dean Stark trap for 1.5 h. The reaction mixture was concentrated and purified by preparative TLC (silica, 30% ethyl acetate/hexane). The collected product was combined with the small amount obtained in the previous aborted attempt (see above) to give 91.2 mg (77%). ESI-MS calc. for C25H30F6N2O3S: 552; Found: 553 (M+H).

EXAMPLE 5

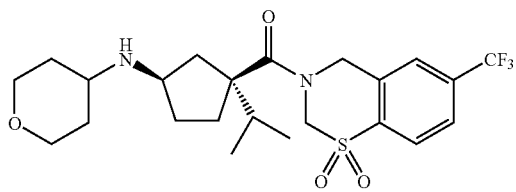

Step A:

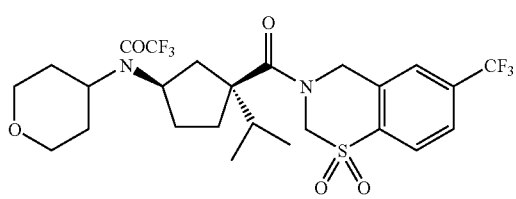

mCPBA (77%, 152 mg, 0.680 mmol) Was added to a solution of INTERMEDIATE 9 (75.1 mg, 0.136 mmol) in 3 mL of DCM. The resulting reaction mixture was stirred at room temperature for 2.25 h. The mixture was diluted and washed with saturated NaHSO3 solution, saturated NaHCO3 solution twice, and brine. The organic layer was dried over anhydrous MgSO4, filtered, and concentrated. Purification by MPLC (silica, 70% ethyl actetate/hexane) provided 63.6 mg (80%) of sulfone.

ESI-MS calc. for C25H30F6N2O5S: 584; Found: 585 (M+H).

Step B:

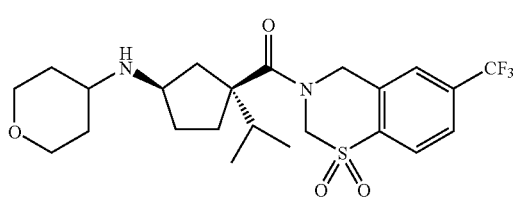

Sodium borohydride (50 mg, 1.32 mg) was added to a solution of the product from Step A (63.6 mg, 0.109 mmol) in ethanol (2 mL). The resulting reaction mixture was stirred at room temperature for overnight. The reaction mixture was concentrated and the residue was purified by reverse phase HPLC (YMC Pack Pro C18, 100×20 mm ID) giving the product as its TFA salt. This was converted to its HCl salt by dissolving in DCM and adding 0.25 mL 1 N HCl/ether, then concentrating to give 36 mg of product.

ESI-MS calc. for C23H31F3N2O4S: 488; Found: 489 (M+H).

EXAMPLE 6A and 6B

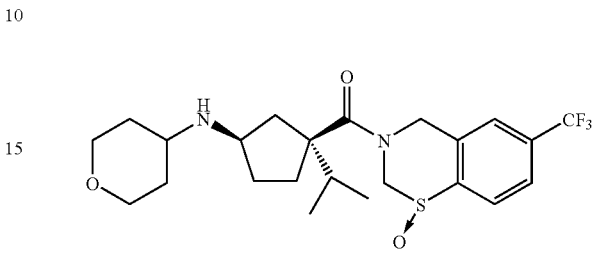

Step A:

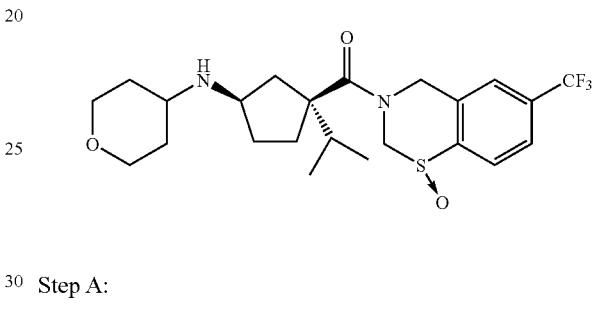

mCPBA (77%, 4-5 mg) Was added to a solution of INTERMEDIATE 9 (10.2 mg, 0.0185 mmol) in 1 mL of DCM. The resulting reaction mixture was stirred at room temperature for 2 h. The mixture was diluted with DCM and washed with saturated NaHSO3 solution, saturated NaHCO3 solution twice, and brine. The organic layer was dried over anhydrous MgSO4, filtered, and concentrated. Purification by preparative TLC (silica, 70% ethyl acetate/hexane) allowed separation of two isomers (epimeric sulfoxides), giving 4.9 mg of the top band and 3.8 mg of the bottom band.

Top band: ESI-MS calc. for C25H30F6N2O4S: 568; Found: 569 (M+H).

Bottom band: ESI-MS calc. for C25H30F6N2O4S: 568; Found: 569 (M+H).

Step B:

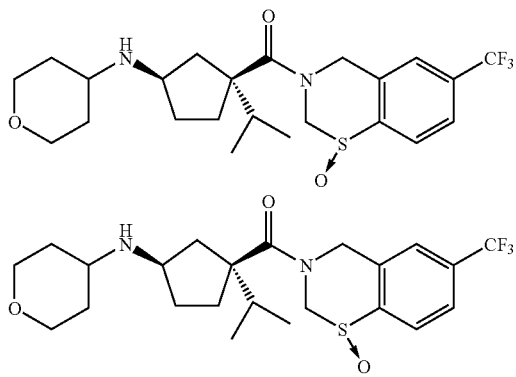

Removal of the trifluoroacetate protecting group from both sulfoxide intermediates was accomplished in an identical fashion to that described in Step B of the synthesis of EXAMPLE 5.

From top band, Step A: ESI-MS calc. for C23H31F3N2O3S: 472; Found: 473 (M+H).

From bottom band, Step A: ESI-MS calc. for C23H31F3N2O3S: 472; Found: 473 (M+H).

EXAMPLE 7

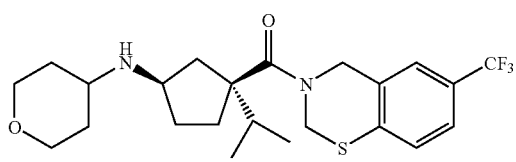

EXAMPLE 7 was prepared from INTERMEDIATE 9 (5.0 mg, 0.0091 mmol) by removal of the trifluoroacetate protecting group in the same manner as described in Step B of the synthesis of EXAMPLE 5, giving 3.97 mg of product as its HCl salt.

ESI-MS calc. for C23H31F3N2O2S: 456; Found: 457 (M+H).

EXAMPLE 8A and 8B

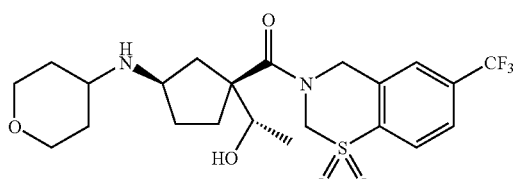

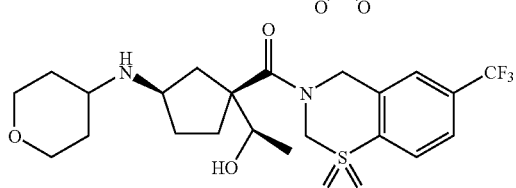

Step A:

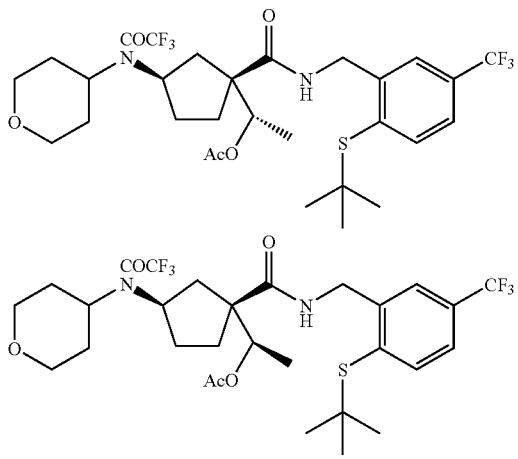

A solution of INTERMEDIATE 7 (320 mg, 0.810 mmol) and INTERMEDIATE 8 (267 mg, 1.01 mmol) in 12 mL of DCM was treated with EDC (311 mg, 1.62 mmol). The reaction mixture was stirred at room temperature overnight. The reaction mixture was diluted with DCM and washed with saturated water, then brine, dried over anhydrous MgSO₄, filtered, and concentrated. Purification by MPLC (silica, 55% ethyl acetate/hexane) allowed separation of two product bands (176 mg faster eluting isomer, 164 mg slower eluting isomer) corresponding to the two product isomers which are epimeric at the hydroxyl bearing carbon.

Step B:

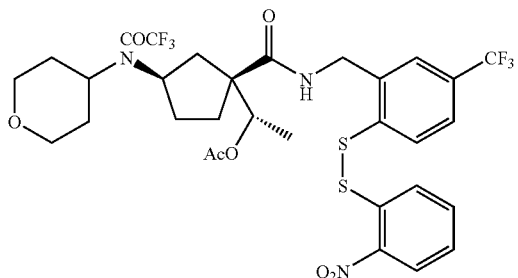

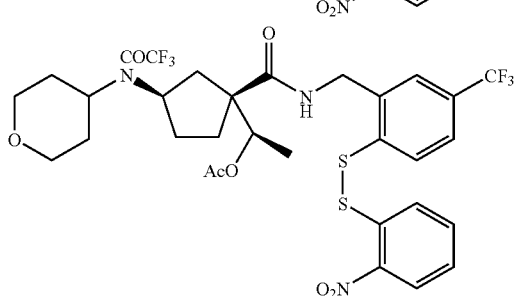

A solution of the faster eluting isomer from Step A (176 mg, 0.275 mmol) in 4 mL of AcOH was treated with 2-nitrobenzenesulfenyl chloride (57 mg, 0.30 mmol) and the resulting mixture was stirred at room temperature for overnight. The reaction mixture was concentrated and the residue purified by MPLC (silica, 60% ethyl acetate/hexane) to afford 178 mg of the disulfide product.

ESI-MS calc. for C31H33F6N3O7S2: 737; Found: 738 (M+H).

The slower eluting isomer from Step A (164 mg, 0.256) was similarly converted to its corresponding disulfide (189 mg).

ESI-MS calc. for C31H33F6N3O7S2: 737; Found: 738 (M+H).

Step C:

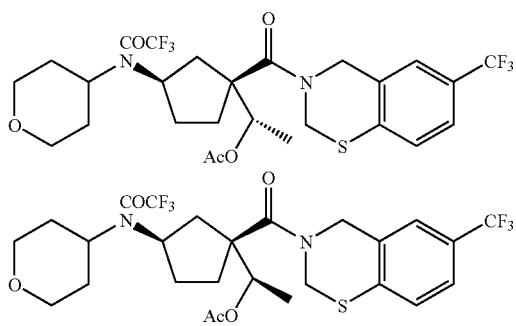

The disulfide from Step B that is derived from the faster eluting isomer in Step A (178 mg, 0.241 mmol) was combined with sodium borohydride (20 mg, 0.53 mmol) under a nitrogen atmosphere. Ethanol (5 mL) was added and the resulting reaction mixture appeared deep red in color. After stirring for 5 min at room temperature, 4 N HCl in dioxane was added dropwise until the color changed permanently from red to pale yellow. The reaction mixture was concentrated. To a solution of the residue in 10 mL of benzene was added paraformaldehyde (250 mg) and TsOH.H$_2$O (5 mg). The reaction vessel was equipped with a Dean Stark trap and condenser and was stirred at reflux under a nitrogen atmosphere for 1.5 h. The reaction mixture was then stirred overnight at room temperature. HPLC-MS analysis indicated that the reaction had not proceeded to completion so more paraformaldehyde (250 mg) and TsOH.H$_2$O (10 mg) was added and the reaction mixture was stirred at reflux for an additional 5 h. The reaction mixture was concentrated. The residue was dissolved in DCM, filtered to remove remaining paraformaldehyde, and concentrated. Purification by preparative TLC (silica, 30% ethyl acetate/hexane) gave 101 mg (70%) of the cyclized product.

ESI-MS calc. for C26H30F6N2O5S: 596; Found: 597 (M+H).

The disulfide from Step B that is derived from the slower eluting isomer in Step A (189 mg, 0.256 mmol) was similarly converted to its corresponding isomeric benzothiazine product (153 mg).

ESI-MS calc. for C26H30F6N2O5S: 596; Found: 597 (M+H).

Step D:

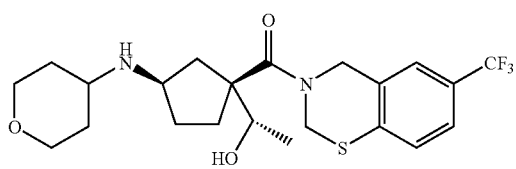

-continued

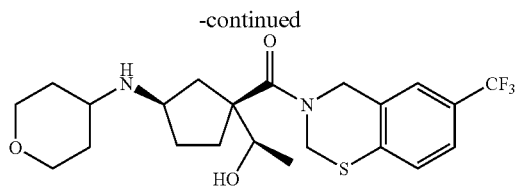

The benzothiazine from Step C that is derived from the faster eluting isomer in Step A (96.8 mg, 0.162 mmol) was dissolved in 3 mL of ethanol and treated with sodium borohydride (95 mg). The reaction mixture was stirred at room temperature for overnight then was concentrated under reduced pressure at 30° C. The residue was dissolved in DCM and washed with saturated NaHCO$_3$ solution. The aqueous layer was extracted with more DCM and the combined organic layers were washed with brine, dried over anhydrous MgSO$_4$, filtered, and concentrated to give 65.9 mg of the desired fully deprotected product.

ESI-MS calc. for C22H29F3N2O3S: 458; Found: 459 (M+H).

The benzothiazine from Step C that is derived from the slower eluting isomer in Step A (127.6 mg, 0.214 mmol) was similarly converted to its corresponding isomeric fully deprotected product.

ESI-MS calc. for C22H29F3N2O3S: 458; Found: 459 (M+H).

Step E:

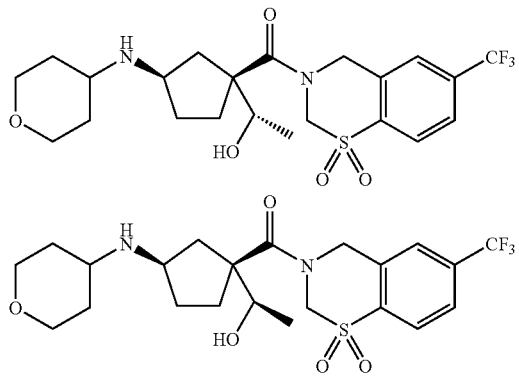

The benzothiazine from Step D that is derived from the faster eluting isomer in Step A (65.9 mg, 0.144 mmol) was dissolved in 1 mL of methanol and treated with a solution of oxone (133 mg, 0.216 mmol) in 1 mL of water. The reaction mixture was stirred at room temperature for overnight. The reaction mixture was quenched by addition of saturated Na$_2$SO$_3$ solution and saturated NaHCO$_3$ solution. The resulting mixture was extracted three times with DCM. The combined organic layers were dried over anhydrous MgSO$_4$, filtered, and concentrated. Purification by preparative TLC [silica, 10% of (10% ammonium hydroxide solution (28-30%)/methanol) in DCM] afforded the product. The free base product was converted to its hydrochloride salt with 1 N HCl/ether (~0.25 mL) in 1 mL of DCM. Evaporation of the solvent afforded 57.2 mg of the target compound as a white solid.

ESI-MS calc. for C22H29F3N2O5S: 490; Found: 491 (M+H).

The benzothiazine from Step D that is derived from the slower eluting isomer in Step A (87.8 mg, 0.191 mmol) was similarly oxidized to its corresponding sulfone (75.9 mg).

ESI-MS calc. for C22H29F3N2O5S: 490; Found: 491 (M+H).

EXAMPLE 9

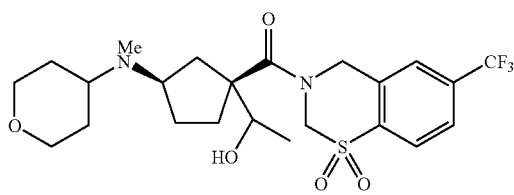

To a solution of the benzothiazine from EXAMPLE 8 that is derived from the faster eluting isomer in Step A (9.6 mg, 0.020 mmol) in 0.2 mL of DCM was added triethylamine (3 μL, 0.02 mmol), 37% formaldehyde (5.4 μL, 0.20 mmol), 4 Å molecular sieves powder, and sodium triacetoxyborohydride (21 mg, 0.098 mmol). The reaction mixture was stirred under a nitrogen atmosphere at room temperature overnight. The reaction mixture was diluted with DCM and washed with NaHCO3 solution and brine, dried over anhydrous MgSO4, filtered, and concentrated. Purification by preparative TLC [silica, 10% of (10% ammonium hydroxide solution (28-30%)/methanol) in DCM] afforded the free base which was converted to its hydrochloride salt (3.2 mg) with 1 N HCl in ether (a single isomer).

ESI-MS calc. for C23H31F3N2O5S: 504; Found: 505 (M+H).

EXAMPLE 10

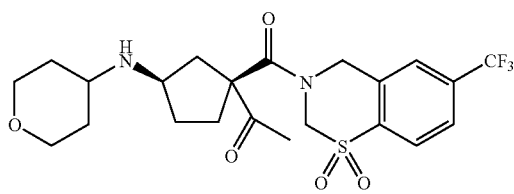

To a solution of the benzothiazine from EXAMPLE 8 that is derived from the slower eluting isomer in Step A (33 mg, 0.067 mmol) in 2 mL of DCM was added Jones reagent (6 drops). The reaction mixture was stirred at room temperature for 2.5 h, then the reaction was quenched with excess isopropanol. The mixture was filtered through a plug of celite and the filtrate was concentrated. Purification by reverse phase HPLC (YMC Pack Pro C18, 10×20 mm ID) gave the product as its TFA salt. This was converted to its HCl salt by dissolving in DCM and adding excess 1 N HCl/ether, then concentrating to give 18.5 mg of product.

ESI-MS calc. for C22H27F3N2O5S: 488; Found: 489 (M+H).

EXAMPLE 11

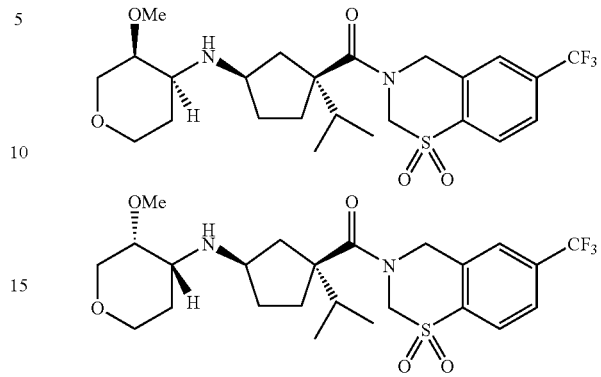

Step A:

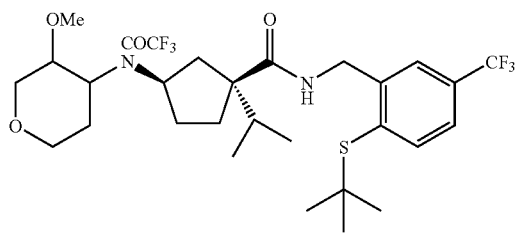

INTERMEDIATE 5 (312 mg, 0.818 mmol), INTERMEDIATE 8 (280 mg, 1.06 mmol), and EDC (314 mg, 1.64 mmol) were combined in 10 mL of DCM. DMAP (~15 mg) was added and the reaction mixture was permitted to stir at room temperature for 5 h. More of INTERMEDIATE 9 (130 mg) was then added and the reaction mixture was stirred overnight. The mixture was diluted with DCM and washed with water, then brine, dried over anhydrous MgSO4, filtered, and concentrated. Purification by MPLC (silca, 45% ethyl acetate/hexane) afforded 396 mg of product.

ESI-MS calc. for C29H40F6N2O4S: 626; Found: 627 (M+H).

Step B:

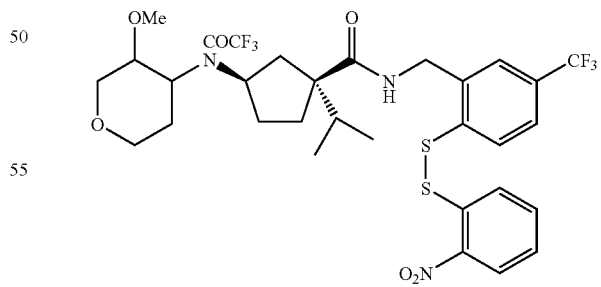

A solution of the product from Step A (396 mg, 0.632 mmol) in 5 mL of AcOH was treated with 2-nitrobenzenesulfenyl chloride (132 mg, 0.695 mmol) and the resulting mixture was stirred at room temperature for overnight. The reaction mixture was concentrated and purified by MPLC (silica, 65% ethyl acetate/hexane) to give 449 mg of disulfide.

ESI-MS calc. for C31H35F6N3O6S2: 723; Found: 724 (M+H).

Step C:

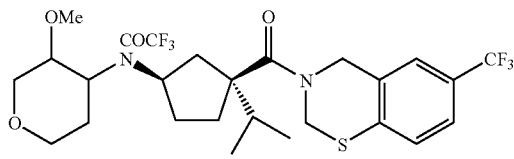

The disulfide from Step B (449 mg, 0.620 mmol) was combined with sodium borohydride (47 mg, 1.24 mmol) under a nitrogen atmosphere. Precooled (0° C.) ethanol (10 mL) was added and the resulting reaction mixture appeared deep red in color. After stirring for 5 min at room temperature, 4 N HCl in dioxane was added dropwise until the color changed permanently from red to pale yellow. The reaction mixture was concentrated. To a solution of the residue in 10 mL of toluene was added paraformaldehyde (1 g) and TsOH.H$_2$O (20 mg). The reaction vessel was equipped with a Dean Stark trap and condenser and was stirred at reflux under a nitrogen atmosphere for 6 h. The reaction mixture was then stirred overnight at room temperature. The reaction mixture was concentrated. The residue was dissolved in DCM, filtered to remove remaining paraformaldehyde, and concentrated. Purification by preparative TLC (silica, 35% ethyl acetate/hexane) gave 181 mg of the cyclized product.

ESI-MS calc. for C26H32F6N2O4S: 582; Found: 583 (M+H).

Step D:

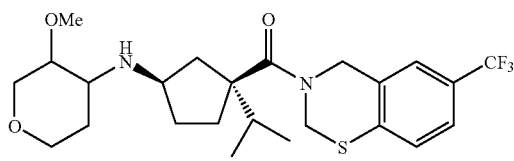

The benzothiazine from Step C (181 mg, 0.311 mmol) was dissolved in 5 mL of ethanol and treated with sodium borohydride (120 mg, 3.1 mmol). The reaction mixture was stirred at room temperature for overnight, then concentrated. The residue was dissolved in DCM and washed with saturated NaHCO$_3$ solution, then brine, dried over anhydrous MgSO$_4$, filtered, and concentrated to give 154 mg of the desired deprotected product.

ESI-MS calc. for C24H33F3N2O3S: 486; Found: 487 (M+H).

Step E:

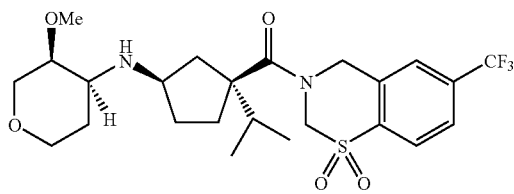

-continued

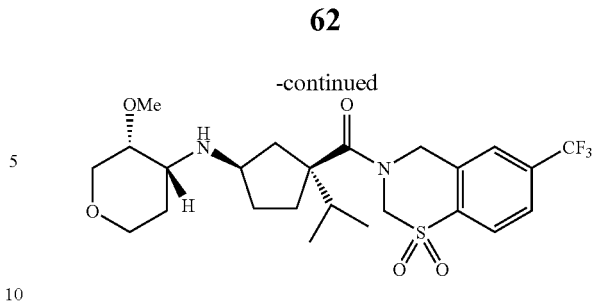

The benzothiazine from Step D (153 mg, 0.314 mmol) was dissolved in 2 mL of methanol, cooled to 0° C., and treated with a solution of oxone (387 mg, 0.629 mmol) in 2 mL of water. The reaction mixture was warmed to room temperature and stirred for 5.5 h. The reaction mixture was quenched by addition of saturated Na$_2$SO$_3$ solution and saturated NaHCO$_3$ solution. The resulting mixture was extracted four times with DCM. The combined organic layers were dried over anhydrous MgSO$_4$, filtered, and concentrated. The crude product mixture which was comprised of predominantly two stereoisomers was purified and separated into two single isomers (29 mg faster eluting peak and 37 mg slower eluting peak) by chiral HPLC using a Chiralcel OD column (2 cm×25 cm, Daicel Chemical Industries), eluting with 60% i-propanol/heptane. This required 3 injections of approximately 40 mg of material/injection, and was performed in an automated fashion using a Gilson fraction collector integrated with Gilson Unipoint software. The resulting free bases were converted to their corresponding hydrochloride salts by dissolving in DCM and adding 56 µL and 71 µL, respectively, then concentrating.

Peak 1: ESI-MS calc. for C24H33F3N2O5S: 518; Found: 519 (M+H).

Peak 2: ESI-MS calc. for C24H33F3N2O5S: 518; Found: 519 (M+H).

INTERMEDIATE 10

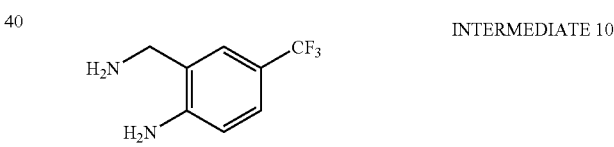

Step A:

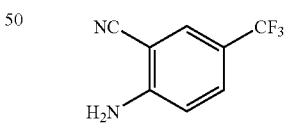

NH$_4$OH Solution (30%, 25 mL) was added to a solution of 2-fluoro-5-(trifluoromethyl)benzonitrile (10.5 g, 55.5 mmol) in 25 mL of THF. The vessel was sealed and stirred at 60° C. for 3 h. The reaction mixture was concentrated, then was partitioned between ether and water. The ethereal layer was washed with brine, dried over anhydrous MgSO$_4$, filtered, and concentrated. HPLC-MS shows a 1:1 ratio of starting material to product. Purification by flash chromatography (silica, 20-35% gradient of ethyl acetate/hexane-increasing in 5% increments) afforded 3.55 g of desired aniline.

ESI-MS calc. for C8H5F3N2: 186; Found: 187 (M+H).

Step B:

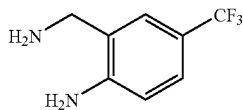

To a solution of 2-amino-5-(trifluoromethyl) benzonitrile (3.55 g, 19.1 mmol) in 50 mL of ethanol was added ammonium hydroxide solution (30%, 13 mL) and Raney® 2800 nickel (slurry in water, ~1 g). The resulting mixture was agitated under 50 psi of hydrogen gas for 21 h using a Parr apparatus. The reaction mixture was then filtered through celite washing with ethanol and then water. The filtrate was concentrated to dryness under reduced pressure and the residue so obtained was purified by flash chromatography [silica, 10 to 20% gradient (2.5% increments) of (10% ammonium hydroxide solution (28-30%)/methanol) in DCM) to afford 2.61 g (72%) of desired amine as a white solid.

H NMR (CDCl$_3$, 500 MHz): δ 7.37 (br s, 1H), 7.25 (dd, J=8.5, 2.0 Hz, 1H), 6.76 (d, J=8.5 Hz, 1H), 3.75 (s, 2H).

INTERMEDIATE 11

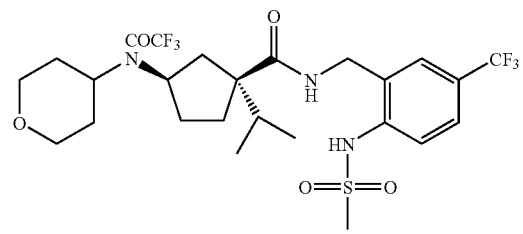

INTERMEDIATE 2 (522 mg, 1.49 mmol) and INTERMEDIATE 10 (353 mg, 1.86 mmol) were combined with EDC (571 mg, 2.98 mmol) and 1-hydroxy-7-azabenzotriazole (399 mg, 2.98 mmol) in 10 mL of DCM. The reaction mixture was stirred at room temperature for 2.5 h. DMF (2 mL) Was added to help solubilize the reagents and the reaction mixture was then stirred overnight at room temperature. Since the reaction was still incomplete, INTERMEDIATE 10 (213 mg, 1.12 mmol) and an additional 10 mL of DMF was added and the mixture was stirred overnight again. The reaction mixture was partially concentrated to remove the DCM. The resulting mixture was partitioned between ethyl acetate and water. The organic layer was washed with water 3 more times, then with brine. The organic layer was then dried over anhydrous MgSO$_4$, filtered, and concentrated. Purification by MPLC (silica, 70% ethyl acetate/hexane) gave 722 mg (93%) of expected amide.

ESI-MS calc. for C24H31F6N3O3: 523; Found: 524 (M+H).

EXAMPLE 12

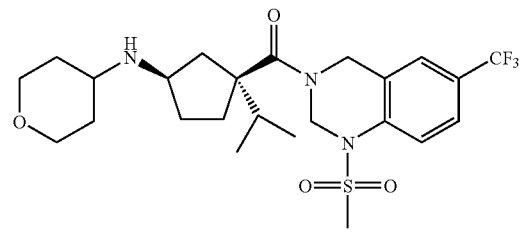

Step A:

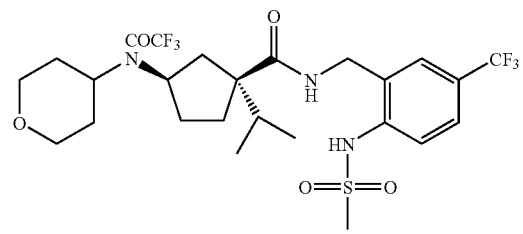

To a solution of INTERMEDIATE 11 (301 mg, 0.575 mmol) in 10 ML of DCM was added pyridine (558 µL, 6.90 mmol) and methanesulfonyl chloride (445 µL, 5.75 mmol). The reaction mixture was stirred at room temperature overnight. The reaction mixture was diluted with DCM and washed with 1 N HCl solution, saturated NaHCO$_3$ solution, and brine, dried over anhydrous MgSO$_4$, filtered, and concentrated. Purification by MPLC (silica, 75% ethyl acetate/hexane) provided 319 mg (92%) of methane sulfonamide product.

ESI-MS calc. for C25H33F6N3O5S: 601; Found: 602 (M+H).

Step B:

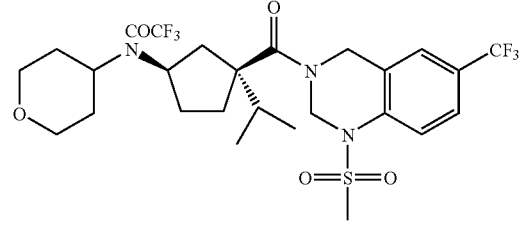

The product from Step A (319 mg, 0.530 mmol) was combined with paraformaldehyde (~600 mg) and pTSOH.H$_2$O (~10 mg) in 10 mL of toluene. The reaction vessel was equipped with a Dean Stark trap and a condenser, and the reaction mixture was stirred at reflux for 1.5 h, whereupon more paraformaldehyde (~500 mg) was added and the reaction mixture was stirred at reflux for an additional 1 h. The reaction mixture was concentrated. Purification by MPLC (silica, 60% ethyl acetate/hexane) furnished 297 mg (91%) of the cyclized product.

ESI-MS calc. for C26H33F6N3O5S: 613; Found: 636 (M+Na$^+$).

Step C:

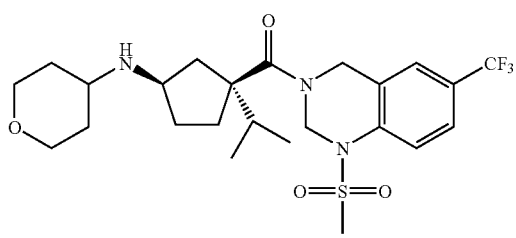

The product from Step B (44.8 mg, 0.0730 mmol) was dissolved in 2 mL of ethanol and treated with sodium borohydride (28 mg, 0.73 mmol). The resulting reaction mixture was stirred at room temperature overnight. The reaction mixture was concentrated and purified by reverse phase HPLC (YMC Pack Pro C18, 100×20 mm ID) giving the product as its TFA salt. This was converted to its HCl salt by dissolving in DCM and adding 10 drops of 1 N HCl/ether, then concentrating to give 29.1 mg of product.

ESI-MS calc. for C24H34F3N3O4S: 517; Found: 518 (M+H).

EXAMPLE 13

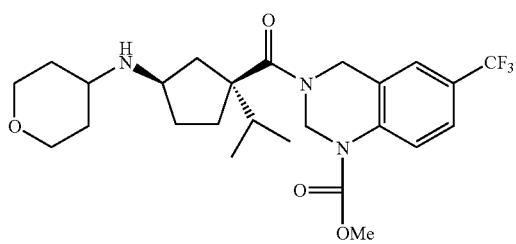

EXAMPLE 13 was prepared in an analogous fashion to EXAMPLE 12 starting from INTERMEDIATE 11 except that methyl chloroformate was used in place of methanesulfonyl chloride in Step A.

ESI-MS calc. for C25H34F3N3O4: 497; Found: 498 (M+H).

EXAMPLE 14

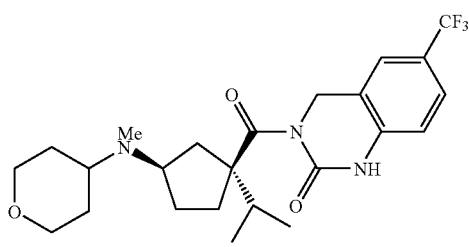

Step A:

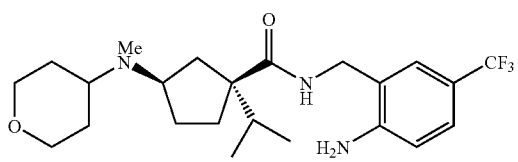

INTERMEDIATE 3 (102 mg, 0.379 mmol) and INTERMEDIATE 10 (115 mg, 0.606 mmol) were combined with EDC (145 mg, 0.758 mmol) and 1-hydroxy-7-azabenzotriazole (102 mg, 0.758 mmol) in 6 mL of DCM and 3 mL of DMF. The reaction mixture was stirred at room temperature overnight. The reaction mixture was partially concentrated to remove the DCM. The resulting mixture was partitioned between ether and water. The ethereal layer was washed with water 2 more times, then with brine. HPLC-MS analysis indicated that the ethereal layer contained no product and that the product remained in the aqueous layer. The original aqueous layer was therefore extracted six times with DCM. The combined organic layers were then dried over anhydrous MgSO$_4$, filtered, and concentrated. Purification by preparative TLC [silica, 10% of (10% ammonium hydroxide solution (28-30%)/methanol) in DCM] gave 143 mg of the pure product.

ESI-MS calc. for C23H34F3N3O2: 441; Found: 442 (M+H).

Step B:

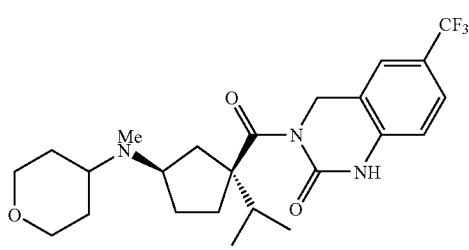

To a solution of the product from Step A (131 mg, 0.297 mmol) in 10 mL of toluene was added 1.93 M phosgene in toluene (1.25 mL, 2.38 mmol). The resulting mixture was stirred at reflux for 3.5 h, then at room temperature overnight. The reaction mixture was concentrated and purified by reverse phase HPLC (YMC Pack Pro C18, 100×20 mm ID) giving the product as its TFA salt. This was converted to its HCl salt by dissolving in DCM and adding excess 1 N HCl/ether, then concentrating to give 94.4 mg of product.

ESI-MS calc. for C24H32F3N3O3: 467; Found: 468 (M+H).

EXAMPLE 15

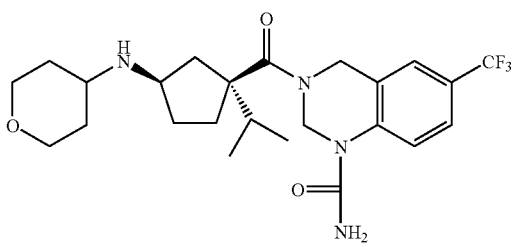

Step A:

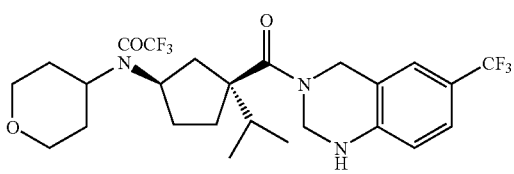

To a solution of INTERMEDIATE 11 (242 mg, 0.463 mmol) in 10 mL of toluene was added paraformaldehyde (~500 mg) and the resulting mixture was stirred at reflux for 2 h in a flask equipped with a Dean Stark trap and condenser. The reaction mixture was concentrated and the residue was purified by MPLC (silica, 70% ethyl acetate/hexane) to give 66 mg of desired product.

ESI-MS calc. for C25H3 F6N3O3: 535; Found: 536 (M+H).

Step B:

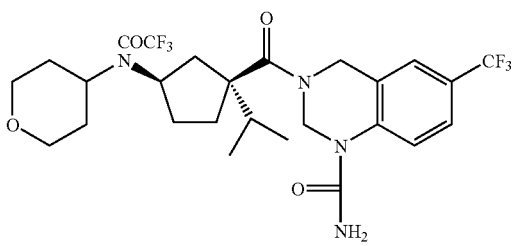

To a solution of the product from Step A (34.4 mg, 0.0642 mmol) in 2 mL of DCM was added pyridine (13 µL, 0.16 mmol) followed by p-nitrophenylchloroformate (26 mg, 0.13 mmol). After stirring at room temperature for 2 h, more pyridine (5.2 µL, 0.064 mmol) and p-nitrophenylchloroformate (13 mg, 0.064 mmol) were added. After an additional 1 h, more pyridine (13 µL, 0.16 mmol) and p-nitrophenylchloroformate (26 mg, 0.13 mmol) were again added and the reaction mixture was stirred overnight. Then NH3 gas was bubbled through the reaction mixture for 1 h, the flask was sealed and the mixture was stirred for 3 days. The reaction mixture was diluted with DCM and washed with 1 N HCl solution, saturated NaHCO3 solution, and brine, dried over anhydrous MgSO4, filtered, and concetrated. Purification by preparative TLC (silica, 50% ethyl acetate/hexane) afforded 13 mg of carbamate product.

ESI-MS calc. for C26H32F6N4O4: 578; Found: 579 (M+H).

Step C:

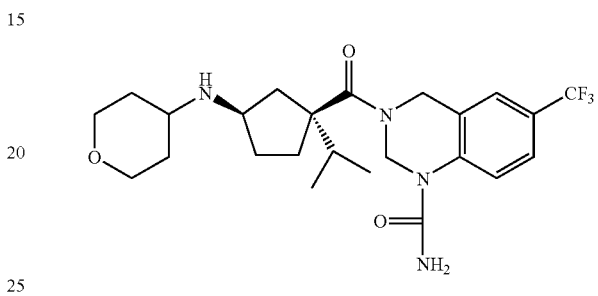

To a solution of the product from Step B (13 mg, 0.022 mmol) in 2 mL of ethanol was added sodium borohydride (20 mg) and the resulting mixture was stirred overnight at room temperature. The reaction mixture was concentrated and the residue obtained was purified by reverse phase HPLC (YMC Pack Pro C18, 100×20 mm ID) giving the product as its TFA salt. This was converted to its HCl salt by dissolving in DCM and adding excess 1 N HCl/ether, then concentrating to give 8.7 mg of product.

ESI-MS calc. for C24H33F3N4O3: 482; Found: 483 (M+H).

EXAMPLE 16

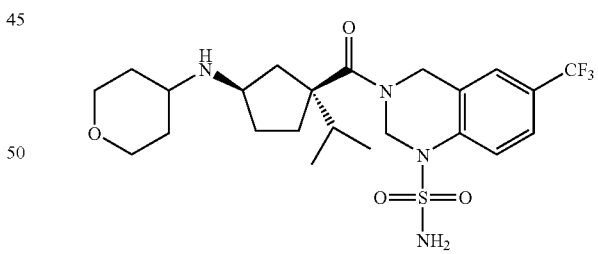

EXAMPLE 16 was prepared in an analogous fashion to that described for EXAMPLE 15 starting from INTERMEDIATE 11 except that in Step B the sulfamide is generated from 10 equivalents each of chlorosulfonyl isocyanate and formic acid (according to the procedure described in: Timberlake, J. W., Ray, W. J., Jr., Stevens, E. D., and Klein, C. L. *J. Org. Chem.* (1989), 54, 5824-5826) rather than the urea shown in EXAMPLE 15.

ESI-MS calc. for C23H33F3N4O4S: 518; Found: 519 (M+H).

EXAMPLE 17

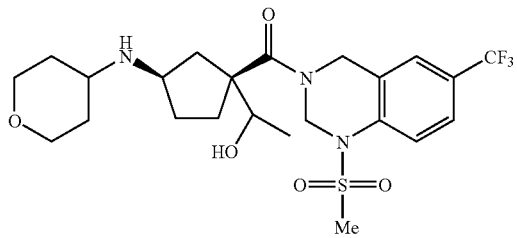

EXAMPLE 17 was prepared from INTERMEDIATES 7 and 10 in an analogous fashion to that shown for the synthesis of INTERMEDIATE 11 followed by EXAMPLE 12. The final product is a mixture of two diastereomers epimeric at the hydroxyl bearing carbon. The final deprotection Step shown in EXAMPLE 12 also simultaneously removes both the trifluoroacetate and acetate protective groups from the amine and hydroxy positions respectively, without any modification to the procedure being necessary.

ESI-MS calc. for C23H32F3N3O5S: 519; Found: 520 (M+H).

INTERMEDIATE 12

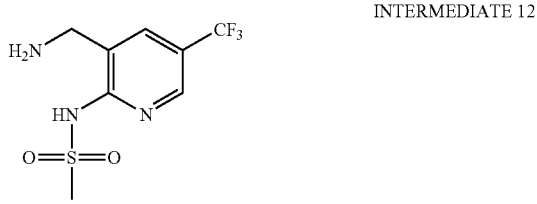

Step A:

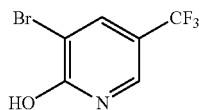

To a solution of 5-trifluoromethyl-2-pyridinal (51.0 g, 307 mmol) and sodium acetate (26.2g, 319 mmol) in glacial acetic acid (200 mL) was added bromine (16.7 mL, 325 mmol) and the resulting mixture was heated at 80° C. for 2.5 h. The reaction was allow to cool to room temperature and then was evaporated under reduced pressure. The residue was neutralized with saturated NaHCO$_3$ solution and extracted with ethyl acetate (3×200 mL). The organics were combined, dried over MgSO$_4$, filtered, and evaporated in vacuo to yield 74.45 g (98.7%) of the crude product.

1H NMR (400 MHz, CDCl$_3$) δ 8.04 (d, J=2.6 Hz, 1H), 7.89 (m, 1H).

Step B:

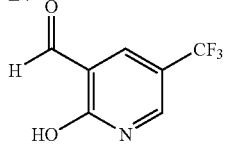

Under nitrogen, the product described in Step A, (48.8 g, 202 mmol) was added in small portions to a suspension of NaH (8.9 g, 220 mmol) in anhydrous THF (500 mL). After complete addition of the intermediate, the reaction mixture was cooled to −78° C. and treated with tert-Butyllithium (260 mL, 444 mmol) dropwise via syringe. After stirring for 5 minutes, DMF (50.0 mL, 707 mmol) was added slowly to maintain the temperature below −50° C. The resulting mixture was then stirred for 10 h allowing to warm to room temperature. The mixture was quenched with 2 N HCl and then diluted with ethyl acetate (1000 mL). The organic layer was separated, washed with brine, dried over MgSO$_4$, and evaporated in vacuo. The desired product was precipitated out of ethyl acetate and hexane and filtered to yield a light brown solid (28.55 g, 73.8%).

$^1$H NMR (500 MHz, CD$_3$OD) δ 10.13 (s, 1H), 8.21 (s, 2H).

Step C:

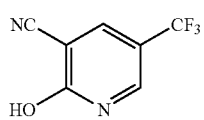

A mixture of the product from Step B, (18.2 g, 95.0 mmol), sodium formate (7.10 g, 105 mmol), hydroxylamine hydrochloride (7.30 g, 105 mmol), and formic acid (150 mL) was stirred at room temperature for 2 h and then refluxed overnight. The reaction mixture was cooled to room temperature and was allowed to stand at room temperature for 7 days. The reaction was poured into water and extracted with ethyl acetate (3×). The combined organic layers were washed with water (2×), saturated NaHCO$_3$ and brine, dried over Na$_2$SO$_4$, filtered, and concentrated in vacuo to yield the desired product as a brown powder (17.84 g, 89.8%).

1H NMR (400 MHz, CD$_3$OD) δ 8.37 (d, J=2.7 Hz, 1H), 8.19 (q, J=0.7 Hz, 0.3??/Hz, 1H).

Step D:

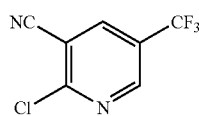

To a mixture of phosphorous oxychloride (13.4 mL, 144 mmol) and quinoline (8.70 mL, 73.4 mmol) was added the product from Step C (24.6 g, 131 mmol) and the resulting mixture was refluxed for 3 h. The reaction was cooled to 100° C. before water (70 mL) was slowly added. The mixture was further cooled to room temperature and neutralized carefully with saturated NaHCO$_3$ solution. The aqueous layer was extracted with ethyl acetate (3×) and the organic layers were combined, dried over MgSO$_4$, filtered, and evaporated in vacuo. The crude product was purified by flash chromatography to afford (23.5 g, 87.0%) of the desired compound.

1H NMR (500 MHz, CDCl$_3$) δ 8.88 (d, J=2.0 Hz, 1H), 8.26 (d, J=2.5 Hz, 1H).

Step E:

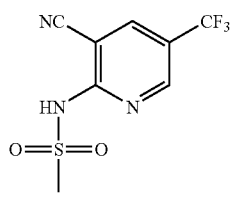

The product from Step D (2.04 g, 9.88 mmol) was combined with methane sulfonamide (1.03 g, 10.9 mmol) and potassium carbonate (2.73 g, 19.8 mmol) in 15 mL of DMSO. The resulting mixture was stirred at 90° C. for 4 h, then at room temperature overnight. The reaction mixture was concentrated (~1 mm Hg, 60° C. bath temp). The crude product was triturated with ethanol. This material was carried on to the following Step F without further purification.

ESI-MS calc. for C8H6F3N3O2S: 265; Found: 266 (M+H).

Step F:

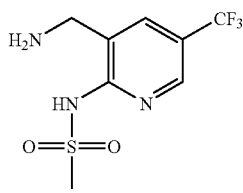

To a solution of the product from Step E (ca 9.88 mmol) in 40 mL of methanol was added ammonium hydroxide solution (30%, 10 mL) and Raney® 2800 nickel (slurry in water, ~500 mg). The resulting mixture was agitated under 45 psi of hydrogen gas for overnight using a Parr apparatus. The reaction mixture was then filtered through celite washing with methanol and then water. The filtrate was concentrated to dryness under reduced pressure and the residue so obtained (2.29 g, 86% for two steps) was used without further purification since it showed only a single peak by HPLC analysis and because of its insolubility in solvent systems necessary for its chromatography.

ESI-MS calc. for C8H10F3N3O2S: 269; Found: 270 (M+H).

H NMR (400 MHz, CD$_3$OD) δ 8.21 (s, 1H), 7.54 (s, 1H), 3.74 (br s, 2H), 3.12 (s, 3H).

EXAMPLE 18

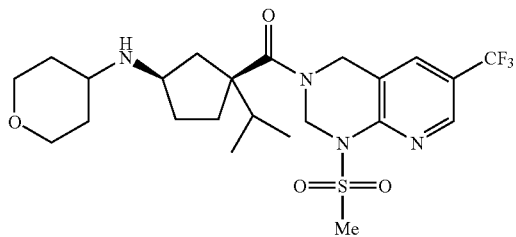

Step A:

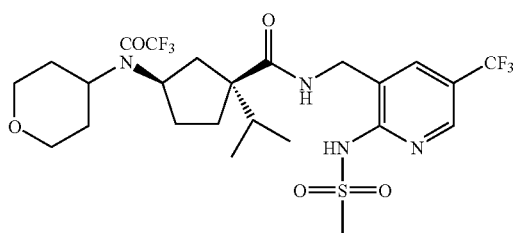

To a cooled (0° C.) solution of INTERMEDIATE 2 (159 mg, 0.452 mmol) in 3 mL of DCM was added oxalyl chloride (118 μL, 1.36 mmol), followed by 1 drop of DMF. The reaction mixture was allowed to warm to room temperature and stir for 1 h. The solvent was removed under reduced pressure and the residue was dissolved in 3 mL of DCM. The resulting solution of acid chloride was added to a cooled (0° C.) solution of INTERMEDIATE 12 (152 mg, 0.566 mmol) and triethylamine (300 μL, 2.15 mmol) in 5 mL of DCM and 1.3 mL of DMF (added to solubilize the amine). After five minutes at 0° C., the reaction mixture was permitted to warm to room temperature and stir for 1 h. Water was added and the reaction mixture was partially concentrated to remove the DCM. The resulting mixture was extracted with twice with ether. The combined ethereal layers were washed twice with water, then brine, dried over anhydrous MgSO$_4$, filtered, and concentrated. Purification by MPLC (silica, 80% ethyl acetate/hexane) provided 198 mg of target amide.

ESI-MS calc. for C24H32F6N4O5S: 602; Found: 603 (M+H).

Step B:

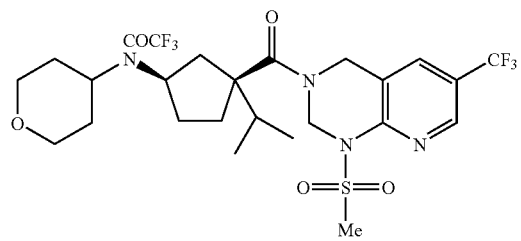

The amide from Step A (116 mg, 0.193 mmol) was combined with paraformaldehyde (~300 mg) in 15 mL of toluene and stirred at reflux for 0.5 h in a flask equipped with a Dean Stark trap and condenser. Analysis of the reaction mixture by HPLC-MS indicated no progress so more paraformaldehyde (~500 mg) and pTsOH.H$_2$O (ca 5-10 mg) were added and reflux was resumed for 1.5 h. The reaction mixture was concentrated and the residue was purified by preparative TLC (silica, 35% ethyl acetate/hexane) to afford 90.3 mg (76%) of the cyclized product.

ESI-MS calc. for C25H32F6N4O5S: 614; Found: 615 (M+H).

Step C:

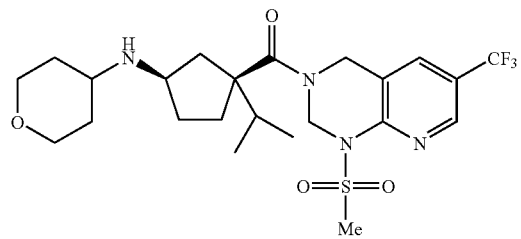

A solution of the cyclized product from Step B (90 mg, 0.15 mmol) in 4 mL of ethanol was treated with sodium borohydride (55 mg, 1.5 mmol) and the resulting mixture was stirred at room temperature overnight. The reaction mixture was concentrated and the residue so obtained was dissolved in DCM and washed with saturated NaHCO$_3$ solution, then brine, dried over anhydrous MgSO$_4$, filtered, and concentrated. Purification by preparative TLC (silica, 7.5% of (10% ammonium hydroxide solution (28-30%)/methanol) in DCM] afforded 54.2 mg of product which was converted to its hydrochloride salt by dissolving in DCM, adding 105 μL of 1 N HCl in ether, and concentrating.

ESI-MS calc. for C23H33F3N4O4S: 518; Found: 519 (M+H).

EXAMPLE 19

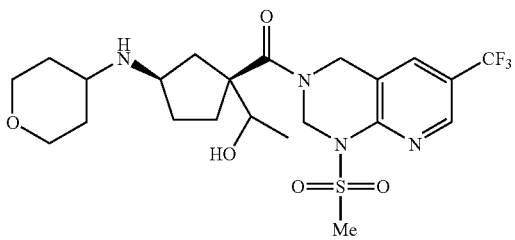

EXAMPLE 19 was prepared in an analogous fashion to that shown for the synthesis of EXAMPLE 18 starting from INTERMEDIATES 7 and 12. The final product is a mixture of two diastereomers epimeric at the hydroxyl bearing carbon. The final deprotection Step shown in EXAMPLE 12 simultaneously removes both the trifluoroacetate and acetate protective groups from the amine and hydroxy positions respectively, without any modification to the procedure being necessary.

ESI-MS calc. for C22H31F3N4O5S: 520; Found: 521 (M+H).

EXAMPLE 20

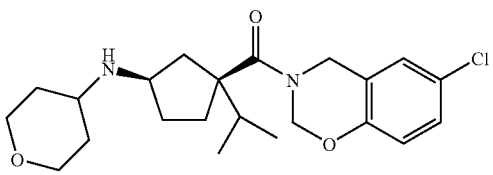

Step A:

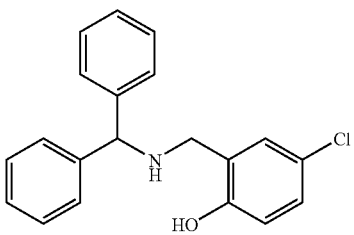

5-Chloro salicylaldehyde (1.0 g, 6.3 mmol) was combined with diphenylmethylamine (1.1 mL, 6.4 mmol), 4 Å powdered molecular sieves (~1 g) and sodium triacetoxyborohydride (5.3 g, 25 mmol) in DCM (50 mL). The resulting mixture was stirred at room temperature for 24 h before being filtered through celite and washed with saturated aqueous sodium bicarbonate and brine. The organic layer was dried over MgSO4, filtered and concentrated under reduced pressure to give 2.0 g of the desired product as a colorless foam (98 %).

ESI-MS calc. for C20H18C1NO: 323.11; found 324 (M+H).

Step B:

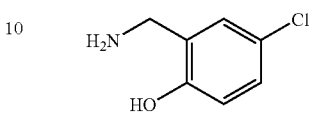

The product from Step A (2.0 g, 6.2 mmol) was combined with palladium hydroxide (20% on active carbon, 200 mg) and concentrated aqueous HCl (0.5 mL, 6 mmol) in methanol (50 mL). The resulting mixture was stirred vigorously under a hydrogen atmosphere (~1 atm) for 3 days before the catalyst was removed by filtration and the filtrate was concentrated under reduced pressure. The product was purified by reverse phase HPLC (C18, 20-100% MeCN/H2O) and converted to its hydrochloride salt by the addition of 2 N HCl in ethyl ether to give 200 mg of a white solid (21%).

ESI-MS calc. for C7H8C1NO: 157.03; found 158 (M+H).

Step C:

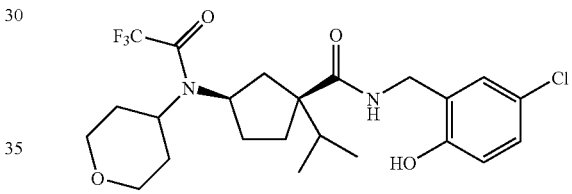

Intermediate (TFA-ACID) (300 mg, 0.86 mmol) was dissolved in DCM (10 mL) and cooled to 0° C. before being treated with oxalyl chloride (250 μL, 2.9 mmol) and DMF (1 drop). This solution was stirred at room temperature for 2 h before being concentrated under reduced pressure and dried under high vacuum for 1 h. The resulting acid chloride was re-dissolved in DCM (5 mL) and added dropwise to a cooled (0° C.) solution of the product from Step B (180 mg, 1.1 mmol) dissolved in DCM (10 mL) and triethylamine (2 mL). This solution was stirred at room temperature for 1 h before it was concentrated under reduced pressure. The resulting residue was dissolved in DCM, washed with aqueous sodium bicarbonate and brine, and dried over Na2SO4, filtered and concentrated under reduced pressure to give 440 mg the desired product (99+%).

ESI-MS calc. for C23H30C1F3N2O4: 490.18; found 491 (M+H).

Step D:

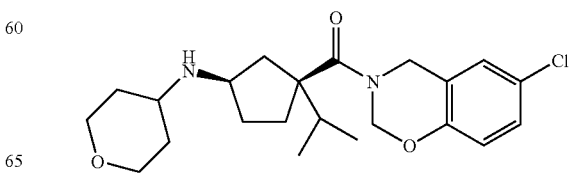

the product from Step C (440 mg, 0.89 mmol) was combined with paraformaldehyde (~1 g) and p-toluenesulfonic acid (50 mg, 0.3 mmol) in benzene (50 mL). The resulting mixture was heated to reflux in the presence of a Dean-Stark trap for 2.5 h. After being cooled to room temperature, the reaction was diluted with ethyl ether and washed with aqueous saturated sodium bicarbonate and brine. The organic layer was dried over Na$_2$SO$_4$, filtered and concentrated under reduced pressure to give a yellow oil which was dissolved in ethanol and treated with sodium borohydride (380 mg, 10 mmol). After stirring at room temperature for 5 h, the reaction was concentrated to dryness. The resulting residue was dissolved in DCM and washed with saturated aqueous sodium bicarbonate and brine. The organic layer was dried over Na$_2$SO$_4$, filtered and concentrated under reduced pressure to give a crude product that was purified by preparative TLC (silica gel, 0.5% NH$_4$OH/4.5% MeOH/95% DCM). The resulting free base was dissolved in DCM, treated with 2 N HCl in diethyl ether, and concentrated to give 160 mg of the desired product as a hydrochloride salt.

ESI-MS calc. for C22H31C1N2O3: 406.20; found 407 (M+H).

INTERMEDIATE 13

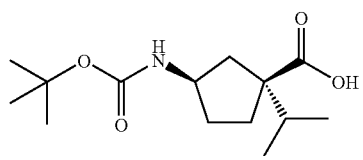

Procedure A:

Step A:

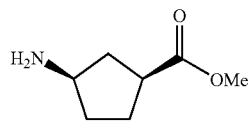

A mixture of (1S)-(+)-2-azabicyclo[2.2.1]hept-5-en-3-one (10.3 g, 94.4 mmol) in ethyl acetate (200 mL) and 10% Pd/C (0.5 g), was hydrogenated at rt. After 24 h the reaction mixture was filtered and evaporated leaving behind 10.4 g (100%) of the product that was taken in 250 mL methanol and HCl (12M, 6 mL). The resultant mixture was stirred at rt, until the reaction was complete (72 h). Evaporation of methanol followed by drying under high vacuum, yielded title compound as an off white solid. $^1$H NMR (500 MHz, D$_2$O): δ 3.70 (s, 3H), 3.01 (m, 1H), 2.38 (m, 1H), 2.16-1.73 (m, 6H).

Step B:

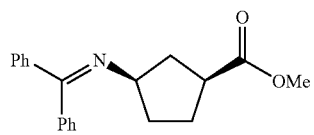

To a suspension of the intermediate from Step A (10.2 g, 56.8 mmol) in dry dichloromethane (200 mL) was added benzophenone imine (10.2 g, 56.8 mmol) at rt and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under vacuum to yield the title compound and required no further purification. $^1$H NMR (500 MHz, CDCl$_3$): δ 7.5-7.18 (m, 10H), 3.75 (m, 1H), 3.7 (s, 3H), 2.78 (m, 1H), 2.26-1.71 (m, 6H).

Step C:

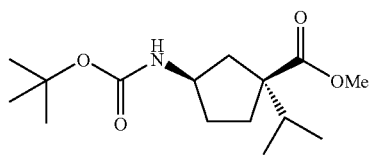

To a solution of lithium diisopropylamide (prepared from diisopropylamine (7.7 g, 76 mmol) and n-butyllithium (30.4 mL, 2.5M in hexanes, 76 mmol) in tetrahydrofuran (120 mL) at −78° C. was added the ester from Step B (18.0 g, 58.6 mmol). The resultant burgundy colored solution was stirred for 20 min after which it was quenched with 2-iodopropane (14.9 gm, 88 mmol). The reaction mixture was gradually warmed over 3 h to 0° C. and this temperature was maintained for an additional 3 h. Reaction was quenched with water and extracted with ethyl acetate. The organic layer was washed with water, brine, dried (anhydrous magnesium sulfate) and concentrated to yield an oil. To the solution of the crude Schiff base (20.0 g) in tetrahydrofuran (100 mL) was added HCl (5.0 mL, 12M). The resulting reaction mixture was allowed to stir at rt for 3 h. After the removal of all volatiles, the hydrochloride salt was taken up into dichloromethane (250 mL), saturated solution of sodium bicarbonate (250 mL) and di-tert-butyl dicarbonate (26.0 g, 1.4 Eq.) were added. The resultant mixture was vigorously stirred overnight at rt. The organic layer was separated and washed with water, brine, dried (anhydrous magnesium sulfate) and concentrated to yield an oil. Purification by flash column chromatography (eluent: hexanes/ethyl acetate 19:1) gave the desired product. $^1$H NMR (500 MHz, CDCl$_3$): 4.79 (br, 1H), 4.01 (m, 1H), 3.71 (s, 3H), 2.18-1.60 (m, 6H), 1.44 (s, 9H), 0.87 (d, J=6.9 Hz, 3H), 0.86 (d, J=6.9 Hz, 3H).

Step D:

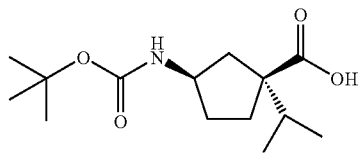

To a solution of the ester from Step C (4.91 g, 17.2 mmol) in methanol (100 mL) was added a solution of LiOH (3.6 g, 85 mmol) in water (20 mL) and tetrahydrofuran (100 mL). The resultant mixture was heated at 80° C. until the reaction was complete (18 h). The methanol was removed in vacuo and the crude product was taken up with water/ethyl acetate (200 mL, 1:4) and cooled to 0° C. The acidity of the mixture was adjusted to pH 6. The ethyl acetate layer was separated, washed with water, brine, dried (anhydrous magnesium sulfate) and concentrated to yield an oil. Purification by flash column chromatography (eluent: hexanes/ethyl acetate 1:1+ 2% AcOH) gave (1S,3R)-3-[(tert-butoxycarbonyl)amino]-1-isopropylcyclopentanecarboxylic acid. $^1$H NMR (500 MHz, CDCl$_3$): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

Procedure B:

Step A:

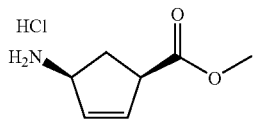

Commercially available (1R,4S)-4-aminocyclopent-2-ene-1-carboxylic acid was converted to its methyl ester hydrochloride salt via classical procedures.

Step B:

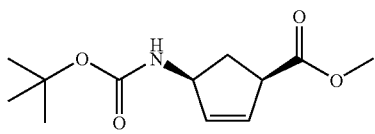

To a suspension of amine from Step A (6.3 1 g, 35.5 mmol) in acetone (40 mL) and water (20 mL) was added solid NaHCO$_3$ (6.6 g, 78 mmol) in portions. After 5 min, a solution of di-tert-butyl dicarbonate (8.5 g, 39 mmol) in acetone (60 mL) was added and the reaction mixture was stirred at rt. After 3 h, acetone was removed in vacuo and the residue was partitioned between ether (500 mL) and saturated aqueous NaHCO$_3$ solution (120 mL). The ether layer was further washed with aqueous NaHCO$_3$ solution (1×100 mL), brine (1×100 mL), dried over anhydrous Na$_2$SO$_4$, concentrated and purified by flash chromatography (15% ethyl acetate/hexanes) to afford the product.

Step C:

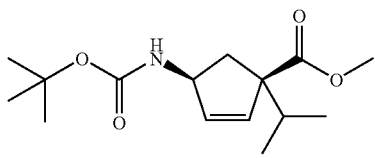

To a solution of lithium bis(trimethylsilyl)amide (10.4 g, 62.1 mmol) in tetrahydrofuran (100 mL) was added a solution of the intermediate from Step B (6.71 g, 27.8 mmol) in tetrahydrofuran (10 mL) over 10 min at −78° C. The resulted solution was stirred at −78° C. for 30 min before isopropyl iodide (3.3 mL, 33 mmol) was added in one portion. The reaction was allowed to warm up to −25° C. and this temperature was maintained overnight. The reaction was then quenched with an aqueous saturated NH$_4$Cl solution (250 mL). The organic layer was separated and the aqueous layer was further extracted with diethyl ether (3×100 mL).

The combined organic layers were then washed with brine (1×100 mL), dried over anhydrous Na$_2$SO$_4$, filtered, concentrated and purified by flash chromatography (5-10% ethyl acetate/hexanes) to give the product as a clear oil (cis/trans=4.3/1). $^1$H NMR (500 MHz, CDCl$_3$) cis-isomer: δ 5.79 (s, 2H), 4.75 (m, 1H), 3.72 (s, 3H), 2.28-2.20 (m, 2H), 2.0 (dd, J=15, 4 Hz, 1H), 1.45 (s, 9H), 0.85 (d, J=6.6 Hz, 3H), 0.81 (d, J=7 Hz, 3H).

Step D:

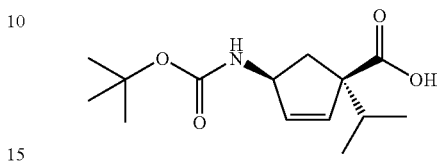

To a solution of the product from Step C (1.6 g, 5.7 mmol) in tetrahydrofuran (50 mL), methanol (50 mL) and water (10 mL) was added LiOH monohydrate (400 mg) and the reaction was heated to reflux overnight until the TLC indicated that the reaction was complete. The organic solvents were removed in vacuo and the aqueous layer was washed with ether (1×) and then acidified slowly with concentrated HCl until the pH reached 4. The resulting suspension was extracted with CH$_2$Cl$_2$ (3×). The combined organic layers were dried over anhydrous MgSO$_4$, filtered and concentrated to give the product as a mixture of two cis/trans isomers (1.5 g) as a foaming yellow solid. This solid was dissolved in ethyl acetate (2 mL) with heating and diluted with hexanes (50 mL) to give a clear solution. This solution was allowed to cool to rt slowly over 1 h and then maintained at −25° C. in a freezer overnight. The trans-isomer was crystalized out along with some of the desired cis-isomer. The mother solution was collected and concentrated to give the title compound (cis-isomer only). $^1$H NMR (500 MHz, CDCl$_3$) cis-isomer: δ 5.80 (m, 2H), 4.80 (m, 1H), 2.40-2.20 (m, 2H), 2.15-2.0 (m, 1H), 1.5 (m, 9H), 1.0-0.8 (m, 3H).

Step E:

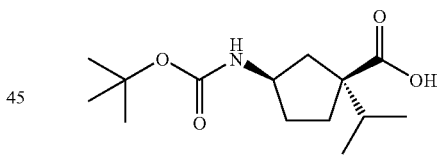

To a solution of the product from Step D (1 g) in ethanol (30 mL) was added 10% Pd/C (100 mg) and the resulting mixture was agitated on a Parr apparatus at 50 lb pressure of H$_2$ overnight. The mixture was filtered through celite and concentrated in vacuo to afford the title compound, (1S,3R)-3-[(tert-butoxycarbonyl)amino]-1-isopropylcyclopentanecarboxylic acid. 1H NMR (500 MHz, CDCl$_3$): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

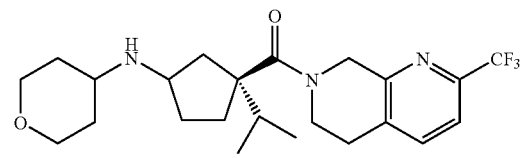

EXAMPLE 21

Step A:

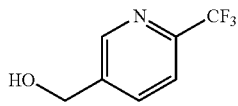

To a suspension of 6-(trifluoromethyl)nicotinic acid (7 g, 37 mmol) in THF (90 mL), cooled to 0-5° C. at $N_2$, was slowly added 2.0M $BH_3$-$Me_2S$ in THF (36.63 mL, 73.26 mmol). The reaction was stirred at room temperature over the weekend. MeOH was added to destroy the extra $BH_3$ and then the mixture was stirred for 30 min. The solvent was evaporated and the residue was dissolved in 1% HCl/MeOH, heated at 50° C. overnight and concentrated under vacuum. The residue was treated and heated with 2N HCl and MeOH seven times and concentrated under vacuum. Crude product was treated with triethylamine (10 mL) and run through a silica gel column (50% EA/HX) to yield the desired alcohol (5.36 g, 82.6%). $^1$H-NMR (400 MHz, $CDCl_3$) δ 8.69 (s, 1H), 7.92 (d, J=8.0 Hz, 1H), 7.69 (d, J=8.0 Hz, 1H), 4.84 (s, 2H), 2.70 (bs, 1H, OH).

Step B:

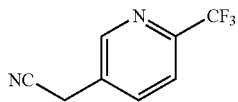

To a solution of the alcohol from Step A (5.36 g, 30.26 mmol) in DCM (60 mL) was added triethylamine (5.06 mL, 36.31 mmol) and DMAP (12 mg). After the reaction mixture was cooled to 0° C., the methanesulfonyl chloride was slowly dropped in to the mixture. The reaction mixture was stirred at room temperature overnight. The mixture was concentrated under vacuum and the residue was purified on a flash column (silica gel, 50% EtOAc/hexane to 70% EtOAc/hexane) to give two intermediates: the expected mesylate (0.72 g), and 5-chloromethyl-2-trifluoromethylpyridine (4.75 g). $^1$H-NMR (400 MHz, $CDCl_3$) δ 8.75 (s, 1H), 7.95 (d, J=8.0 Hz, 1H), 7.72 (d, J=8.0 Hz, 1H), 4.67 (s, 2H). ESI-MS calc. For C7H5C1F3N: 195; Found (M+H).

To a mixture of 0.72 g of the mesylate and 4.75 g of the chloride dissolved in DMSO (15 mL), was added NaCN (1.33 g, 27 mmol). The reaction mixture was stirred at room temperature overnight and then diluted with DCM (10 mL). The resulting mixture was purified by column chromatography (silica gel, 50% EA/HX) to give the desired nitrile (3.71 g, 73.5%). $^1$H-NMR (400 MHz, $CDCl_3$) δ 8.71 (s, 1H), 7.95 (d, J=8.0 Hz, 1H), 7.77 (d, J=8.0 Hz, 1H), 3.80 (s, 2H).

Step C:

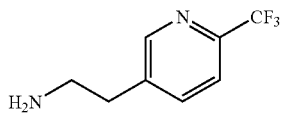

To a solution of the nitrile from Step B (3.67 g, 19.72 mmol) in EtOH (100 mL), was added $NH_4OH$ (25 mL) and Raney Ni (~500 mg). The reaction mixture was agitated on a Parr apparatus under 50 lb pressure of $H_2$ for 6 hr. The solution was filtered through celite and the filtrate was concentrated under vacuum to yield the target amine (3.85 g, 100%). ESI-MS calc. For C8H9F3N2: 190.07; Found: 191 (M+H).

Step D:

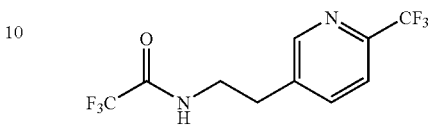

To a cooled (0-5° C.) mixture of the amine from Step C (3.85 g, 20.25 mmol) and pyridine (93.28 mL, 40.5 mmol) in DCM (40 mL), was slowly added trifluoroacetic anhydride (4.29 mL, 30.4 mmol). The reaction mixture was then stirred at room temperature for 3 hr. The mixture was concentrated under vacuum and residue was purified by column chromatography (silica gel, 50% EA/HX) to give the expected trifluoroacetamide (3.626 g, 62.6%). $^1$H-NMR (400 MHz, $CDCl_3$) δ 8.57 (s, 1H), 7.75 (d, J=8.0 Hz, 1H), 7.67 (d, J=8.0 Hz, 1H), 6.70 (br s, 1H, NH), 3.68 (q, J=6.8 Hz, 2H), 3.03 (t, J=6.8 Hz, 2H).

Step E

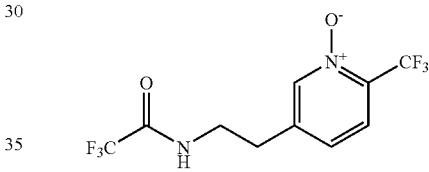

To a cooled (0-5° C.) solution of the trifluoroacetamide from Step D (3.61 g, 12.61 mmol) in HOAc (30 mL), was slowly added $H_2O_2$ (30%, 12.9 mL). The reaction mixture was stirred at 60° C. for 2 days. Extra $H_2O_2$ was added to complete the reaction. HOAc was evaporated under vacuum and residue was stored under high vacuum overnight. The residue was then purified by flash column (silica gel, 8% MeOH/DCM+0.6% $NH_4OH$) to yield the pyridine N-oxide (2.78 g, 73%). $^1$H-NMR (400 MHz, $CDCl_3$) δ 8.22 (s, 1H), 7.67 (d, J=8.2 Hz, 1H), 7.24 (d, J=8.2 Hz, 1H), 7.02 (br s, 1H, NH), 3.68 (q, J=6.8 Hz, 2H), 2.97 (t, J=6.8 Hz, 2H). ESI-MS calc. For C10H8F6N2O2: 302.05; Found: 303 (M+H).

Step F:

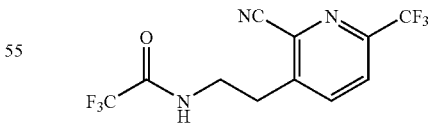

To a solution of the pyridine N-oxide from Step E (2.46 g, 8.14 mmol) in $CHCl_3$ (40 mL), was added a solution of KCN (1.325 g) in water (15 mL). After the reaction mixture was stirred for 15 min, benzoyl chloride (1.11 mL, 9.52 mmol) in $CHCl_3$ (40 mL) was slowly added at 0-5° C. Then the reaction mixture was stirred at room temperature overnight. Organic phase was separated and DCM was used to extracted the aqueous layer three times. The combined organic layers were dried over Na$_2$SO$_4$, filtered, and concentrated under vacuum. The residue was purified by column chromatography (silica gel, 35%-45% EA/HX) to yield the target nitrile (2.18 g, 86%).
$^1$H-NMR (400 MHz, CDCl$_3$) δ 7.98 (d, J=8.2 Hz, 1H), 7.89 (d, J=8.2 Hz, 1H), 6.66 (br s, 1H, NH), 3.77 (q, J=6.8 Hz, 2H), 3.58 (t, J=6.8 Hz, 2H). ESI-MS calc. For C11H7F6N3O: 311.05; Found: 312 (M+H)

Step G:

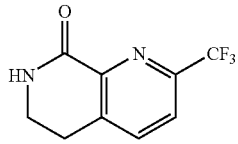

A suspension of the nitrile from Step F (2.18 g, 7.01 mmol) in concentrated HCl (100 mL) was stirred and heated at 115° C. for 3 days. The solvent was evaporated under vacuum and the residue was stored under high vacuum overnight to give 1.88 g of amino acid HCl salt which go to next step without further purification.

To a suspension of the above amino acid HCl salt (1.88 g, 6.99 mmol) in DCM (40 mL), was added EDC (4.00 g, 21.0 mmol). The reaction mixture was stirred at room temperature overnight. Solvent was evaporated under vacuum and residue was purified by column chromatography (silica gel, 15% MeOH/DCM) to yield the desired lactam (1.31 g, 86.6%). $^1$H-NMR (400 MHz, CDCl$_3$) δ 7.83 (d, J=8.0 Hz, 1H), 7.78 (d, J=8.0 Hz, 1H), 7.34 (br s, 1H, NH), 3.68 (td, J1=6.6 Hz, J2=3.0 Hz, 2H), 3.58 (t, J=6.8 Hz, 2H).

Step H:

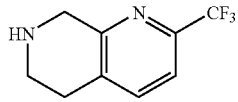

To a cooled (0-5° C.) solution of the lactam from Step G (1.31 g, 6.06 mmol) in THF (40 mL), was slowly added BH$_3$-Me$_2$S in THF (2.0 M, 15.2 mL, 30.3 mmol). The reaction mixture was then stirred at reflux for 2 hr. The resulting mixture was cooled to 0° C., quenched with MeOH, and concentrated under vacuum. The residue was treated with 4N HCl in dioxane and heated at 65° C. for 4 hr and then concentrated under vacuum. The procedure was repeated four times to yield the azatetrahydroisoquinoline as its HCl salt (1.22 g, 100%) as white powder. ESI-MS calc. For C9H9F3N2: 202.07; Found: 203 (M+H)

Purification: To a suspension of crude product (1.22 g, 6.03 mmol) and Et$_3$N (3.45 mL, 24.73 mmol) in DCM (50 mL), was added Boc$_2$O (3.95 g, 18.10 mmol). The reaction mixture was stirred at room temperature for 2.5 hr. The solvent was evaporated and the residue was purified by flash column chromatography (silica gel, 20% EA/HX to 40% EA/HX) to yield Boc-protected azatetrahydroisoquinoline (1.04 g). $^1$H-NMR (400 MHz, CDCl$_3$) δ 7.64 (d, J=8.0 Hz, 1H), 7.51 (d, J=8.0 Hz, 1H), 4.76 (s, 2H), 3.74 (t, J=5.5 Hz, 2H), 2.95 (t, J=5.5 Hz, 2H), 1.51 (s, 9H). The Boc group was cleaved in 15 mL of 4N HCl/dioxane at room temperature for 1 hr. Solvent was evaporated under vacuum to give pure azatetrahydroisoquinoline (750 mg, 62%).

Step I:

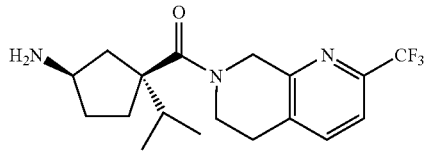

To a flask was added Boc-amino acid (Intermediate 13, 1.10 g, 4 mmol), the azatetrahydroisoquinoline from Step H (1.15 g, 4 mmol), PyBrOP (1.85 g, 4 mmol), DMAP (0.29 g, 2.4 mmol), DIEA (2.77 mL, 16 mmol) and DCM (20 mL). The resulting mixture was stirred for 36 h under nitrogen. The entire mixture was applied onto a silica gel column and eluted with 20% EtOAc/Hexane to yield the target amide (1.5 g, 75%). ESI-MS calc. For C23H32F3N3O3: 455.24; Found: 356 (M+H−100). The Boc protected intermediate was treated with 4N HCl/Dioxane to yield the corresponding amine.

Step J:

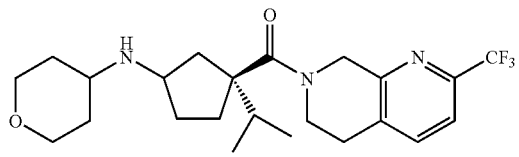

A mixture of the amine from Step I (65 mg, 0.166 mmol), tetrahydro-4H-pyran-4-one (46 mL, 0.497 mmol), powdered molecular sieves (4 Å, 200 mg), and DIEA (52 mg, 0.4 mmol) in DCM (10 mL) was stirred for 30 min. Then sodium triacetoxy boride (105 mg, 0.497 mmol) was added. The resulting mixture was stirred for 4 hr, diluted with DCM, filtered, and the filtrate was washed with sat. aq. Na$_2$CO$_3$. The aqueous layer was extracted again with DCM. The combined DCM layers were dried over Na$_2$SO$_4$ and evaporated. The residue was purified on preparative TLC (1000 micron) (developed by 10% [aq. NH4OH/MeOH 1/9]/DCM) to yield the title compound as a free base. Its HCl salt (22.4 mg) was formed by treatment with 4N HCl/dioxane. $^1$H NMR (CDCl$_3$, 400 MHz): δ 7.65 (d, J=7.9 Hz, 1H), 7.54 (s, J=7.9 Hz, 1H), 4.87 (m, 2H), 3.97 (m, 2H), 3.90 (m, 2H), 3.40 (m, 2H), 3.18 (m, 4H), 2.95 (s, 2H), 2.71 (m, 1H), 2.18 (m, 1H), 2.05 (m, 1H), 1.70-1.90 (m, 6H), 0.86 (m, 6H). ESI-MS calc. for C23H32F3N3O2: 439.24; Found: 440 (M+H).

EXAMPLE 22

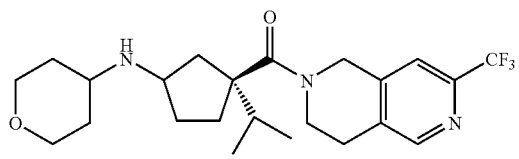

Step A:

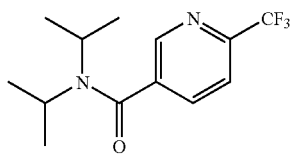

To a suspension of nicotinic acid (20.0 g, 104 mmol) in benzene (120 mL), cooled to 0° C., was added thionyl chloride (38.19 mL, 523.3 mmol). The reaction mixture was refluxed for 5 hr. Then $SO_2$, HCl, solvent and extra thionyl chloride were evaporated under vacuum. The residue as acid chloride was dissolved in DCM (150 mL) and cooled to 0° C. in an ice-water bath. To the acid chloride solution was slowly added diisopropylamine (58.67 mL, 418.6 mmol). The reaction mixture was then stirred at room temperature overnight. The solvent was evaporated and residue was purified by flash column chromatography (25% EtOAc/hexane) to yield the desired diisopropylamide (19.97 g, 69.6%). $^1$H-NMR (400 MHz, $CDCl_3$) δ 8.69 (s, 1H), 7.85 (d, J=8.0 Hz, 1H), 7.74 (d, J=8.0 Hz, 1H), 3.66 (br d, 2H), 1.38 (br d, 12H). ESI-MS calc. For C13H17F3N2O: 274.13; Found: 275 (M+H).

Step B:

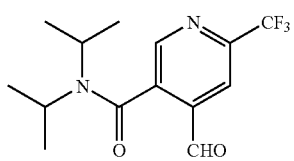

To a flame-dried 1000 mL round-bottomed flask, was added dry ethyl ether (150 mL). The solution was cooled to −78° C. then diisopropylamine (24.46 mL, 174.5 mmol), 2.5 M n-butyllithium in hexane (69.8 mL, 175 mmol), and a solution of the amide from Step A (31.8 g, 116 mmol) in dry ethyl ether (150 mL) were added sequentially. The reaction mixture was stirred at −78° C. for 2.5 hr before DMF (27.03 mL, 290.75 mmol) was slowly added. After the reaction was stirred for another 2 hr, the mixture was warmed and stirred for 1 hr at room temperature. Then the mixture was quenched with 10% citric acid, extracted with ether (three times). The combined ethereal layers were washed with brine, dried over $MgSO_4$, and concentrated. The crude product was purified by flash column chromatography (30/70 EtOAc/hexanes) to yield the expected aldehyde (34.69 g, 98.7%). $^1$H-NMR (400 MHz, $CDCl_3$) δ 10.17 (s, 1H), 8.75 (s, 1H) 8.12 (s, 1H), 3.6 (m, 2H), 1.62 (d, J=7.8 Hz, 2H), 1.19 (d, J=7.8 Hz, 2H).

Step C:

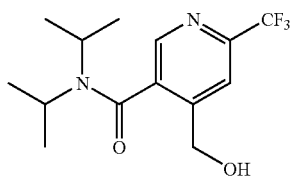

To a solution of the aldehyde from Step B (34.69 g, 114.8 mmol) in ethanol (400 mL), was added sodium borohydride (4.34 g, 115 mmol) in portion. The reaction mixture was stirred at room temperature for 2 hr. Extra $NaBH_4$ was destroyed by adding 2N HCl at 0° C., and the ethanol solvent was evaporated to yield the target alcohol which was used in the next step without further purification. ESI-MS calc. For C14H19F3N2O2: 304.14; Found: 305 (M+H).

Step D:

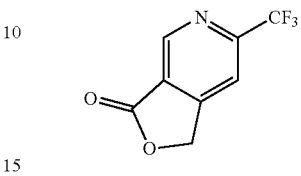

A suspension of the alcohol from Step C (34.94 g, 114.8 mmol) in 6N HCl (500 mL) was refluxed at 110° C. for 2 hr. The reaction mixture was concentrated under vacuum and the residue was partitioned in water/DCM. The pH value was adjusted by triethylamine from 2-3 to 7. The aqueous portion was extracted by DCM (twice) and the combined organic portion was washed by brine, dried over $Na_2SO_4$, filtered and concentrated. The residue was purified by flash column chromatography (silica gel, 30% EA/HX) to yield the expected lactone (15.97 g, 68.5%). $^1$H-NMR (400 MHz, $CDCl_3$) δ 9.29 (s, 1H), 7.92 (s, 1H), 5.48 (s, 2H).

Step E:

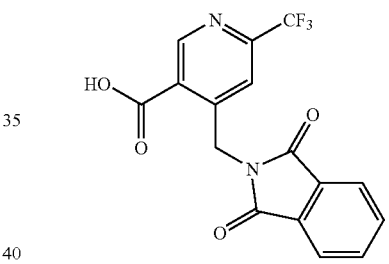

A mixture of the lactone from Step D (15.97 g, 78.62 mmol) and potassium phthalimide (15.72 g, 84.91 mmol) in DMF was heated and refluxed for 5 hr. The reaction was quenched with ice-water and 6N HCl was used to adjust pH from 10 to about 4. The formed white solid was separated by filtration to yield the target carboxylic acid (24.6 g, 83.7%). $^1$H-NMR (400 MHz, $CD_3OD$) δ 9.20 (s, 1H), 7.93 (m, 2H), 7.86 (m, 2H), 7.55 (s, 1H), 5.48 (s, 2H). ESI-MS calc. For C16H9F3N2O4: 350.05; Found: 351 (M+H).

Step F:

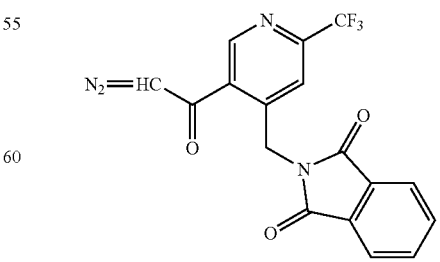

To a new 200 mL beaker, was added 40% (w/v) potassium hydroxide (211 mL), and ethyl ether (650 mL). After the mixture was cooled to 0° C., nitrosomethylurea (46.39 g, 450 mmol) was added to the two phase solution in portions with hand swirling until all the solids were dissolved. The formed solution was frozen at −78° C. and the aqueous layer was separated from the Et₂O portion as a solid. The formed CH₂N₂ in ether was put into a container with KOH pellets and stored in freezer for overnight.

To a suspension of the acid from step E (10.51 g, 30.0 mmol) in DCM, cooled to 0° C., was slowly added triethylamine (5.44 mL, 39.0 mmol) and isobutyl chloroformate (5.06 mL, 39.0 mmol), sequentially. The reaction mixture was stirred for 2 hr at 0° C., washed with saturated NaHCO₃ solution, ice water, and ice cold brine, dried over Na₂SO₄, filtrated, and concentrated to give the mixed anhydride. The formed anhydride was dissolved in ether and cooled to 0° C. To the solution of the mixed anhydride cooled to 0° C., was added the CH₂N₂ prepared above. The reaction mixture was stirred at 0° C. overnight and was slowly raised to room temperature to let CH₂N₂ evaporated. Solvent was then evaporated and residue was tritiated with EtOAc/hexane to yield the diazoketone (8.12 g, 72.4%) as a white solid. 1H-NMR (400 MHz, CDCl₃) δ 8.80 (s, 1H), 7.92 (m, 2H), 7.81 (m, 2H), 7.52 (s, 1H), 5.94 (s, 1H). 5.23 (s, 2H), ESI-MS calc. For C17H9F3N4O3: 374.06; Found: 375 (M+H).

Step G:

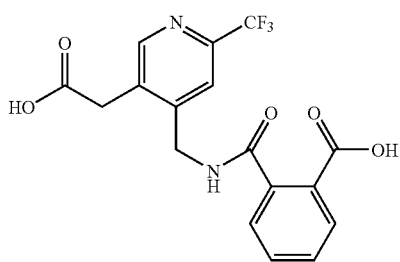

To a solution of 10% AgNO₃ (6.0 g, 35.3 mmol) in water (60 mL), was slowly added 10% NaOH. The formed Ag₂O was filtered, washed by water (three times) and dried under vacuum. The formed Ag₂O was suspended in water (500 mL) and mixed with Na₂CO₃ (4.00 g, 37.7 mmol) and Na₂S₂O₃ (10.42 g, 65.90 mmol). A suspension of Intermediate the diazoketone from Step F (8.00 g, 21.37 mmol) in dioxane (200 mL) was added in portions to the above mixture at 55° C. and the reaction was stirred at 55° C. for 2 hrs. After the solids were filtered out and the pH was adjusted to 4 with 6N HCl, EtOAc was used to extract the solution to yield the target compound (6.33 g, 80%). ESI-MS calc. For C17H13F3N2O5: 382.08; Found: 383 (M+H).

Step H:

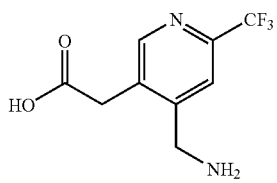

A mixture of the Intermediate from Step G (3.31 g, 8.66 mmol) and 12N HCl (50 mL) was heated at reflux for 3 days. The solvent was evaporated to yield the desired aminoacid which was used in next step without further purification.

Step I:

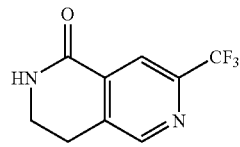

A mixture of the aminoacid from Step H and EDC (9.50 g, 49.8 mmol) in DCM (200 mL) was stirred at room temperature overnight. The solvent was evaporated and the residue was purified by column chromatography (silica gel, 10% MeOH/DCM) to give the expected lactam (985 mg, 27.4%). 1H-NMR (400 MHz, CDCl₃) δ 8.60 (s, 1H), 7.55 (s, 1H), 6.67 (br s, 1H), 4.65 (s, 2H), 3.72 (s, 2H). ESI-MS calc. For C9H7F3N2O: 216.05; Found: 217 (M+H).

Step J:

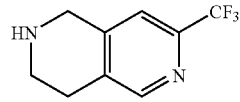

To a cooled (0-5° C.) solution of the lactam from Step I (980 mg, 4.53 mmol) in THF (40 mL), was slowly added BH₃-Me₂S in THF (2.0 M, 11.34 mL, 22.67 mmol). The reaction mixture was then stirred at reflux for 3 hr. The resulting mixture was cooled to 0° C., quenched with methanol, and concentrated under vacuum. The residue was treated with 4N HCl in dioxane, heated at 65° C. for 4 hr, and then concentrated under vacuum. This procedure was repeated three times to yield the desired azatetrahydroisoquinoline as its HCl salt (1.33 g, ~100%) as white powder. ESI-MS calc. For C9H9F3N2: 202.07; Found: 203 (M+H).

Purification: To a suspension of crude azatetrahydroisoquinoline described above (1.33 g) and triethylamine (3.90 mL, 27.86 mmol) in DCM, was added Boc₂O (3.65 g, 16.7 mmol). The reaction mixture was stirred at room temperature for 3 hrs. The solvent was evaporated and the residue was purified by flash column chromatography (silica gel, 20% EA/HX to 40% EA/HX) to yield Boc-protected azatetrahydroisoquinoline (696 mg). ¹H-NMR (400 MHz, CDCl₃) δ 8.51 (s, 1H), 7.44 (s, 1H), 4.65 (s, 2H), 3.72 (t, J=5.4 Hz, 2H), 2.92 (t, J=5.4 Hz, 2H), 1.53 (s, 9H). The Boc group was cleaved in 25 mL of 4N HCl/dioxane at room temperature for 1.5 hr. Solvent was evaporated under vacuum to give pure azatetrahydroisoquinoline (434 mg, 32.6%). 1H-NMR (400 MHz, CD₃OD) δ 8.62 (s, 1H), 7.74 (s, 1H), 4.50 (s, 2H), 3.59 (t, J=6.2 Hz, 2H), 3.23 (t, J=6.2 Hz, 2H ). ESI-MS calc. For C9H9F3N2: 202.07; Found: 203 (M+H).

Step K:

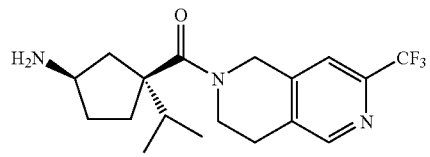

To a flask was added Boc-amino acid (Intermediate 13, 493 mg, 1.82 mmol), the azatetrahydroisoquinoline from Step J (434 mg, 1.82 mmol), PyBrOP (847.6 mg, 1.818 mmol), DMAP (133 mg, 1.09 mmol), DIEA (1.267 mL, 7.27 mmol) and DCM. The resulting mixture was stirred for 48 hr under nitrogen, diluted with DCM, washed with saturated NaHCO₃, dried over Na₂SO₄, filtrated, and concentrated. The residue was purified by preparative TLC (silica gel, 1000 micron, 38% EtOAc/hexane) to yield the Boc protected aminoamide (64.5 mg, 7.8%). ESI-MS calc. For C23H32F3N3O3: 455.24; Found: 356 (M+H−100) and 400 (M+H−56). The Boc protected intermediate was treated with 4N HCl/Dioxane (3 mL) at room temperature for 3 hr to yield the desired aminoamide (55.8 mg).

Step L:

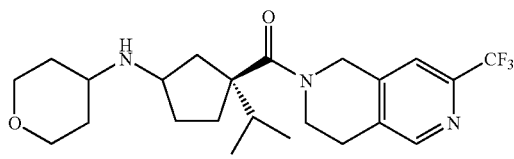

A mixture of the aminoamide from Step L (55.6 mg, 0.142 mmol), tetrahydro-4H-pyran-4-one (40 μL, 0.43 mmol), molecular sieves (4 Å, 150 mg), DIEA(49.5 μL, 0.4 mmol) in DCM (5 mL) was stirred for 30 min. Then sodium triacetoxy borohydride (90 mg, 0.43 mmol) was added. The resulting mixture was stirred over the weekend, diluted with DCM, filtered, and washed with sat. aq. Na₂CO₃. The layers were separated and the aq. layer was extracted with DCM. The combined DCM layers were dried over Na₂SO₄, and concentrated. The residue was purified on preparative TLC (1000 micron) (developed by 8% [aq. NH₄OH/MeOH 1/9]/DCM) to yield the title compound as a free base. Its HCl salt (43.5 mg) was formed by treatment with 4N HCl/dioxane. ESI-MS calc. for C23H32F3N3O2: 439.24; Found: 440 (M+H).

EXAMPLE 23

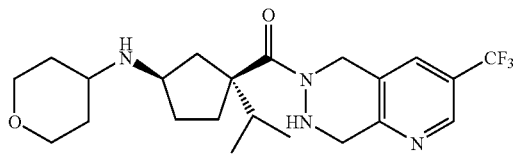

Step A:

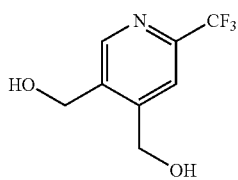

To a solution of the lactone prepared as described in Step D of the synthesis of Example 22 (5.80 g, 28.6 mmol) in ethanol (60 mL), was added sodium borohydride (2.38 g, 62.8 mmol). The reaction was stirred for 4 h. The reaction was quenched with methanol/water(1:1), the extra sodium borohydride was destroyed with 4N HCl in dioxane (twice), and the solvent was evaporated under vacuum. The residue was neutralized with triethylamine and purified by column chromatography (silica gel, 50% EtOAc/hexane to 60% EtOAC/hexane ) to give the desired diol (5.46 g, 92.3%).

¹H-NMR (400 MHz, CDCl₃) δ 8.66 (s, 1H), 7.80 (s, 1H), 4.90 (s, 2H), 4.85 (s, 2H). ESI-MS calc. For C8H8F3NO2: 207.05; Found: 208 (M+H)

Step B:

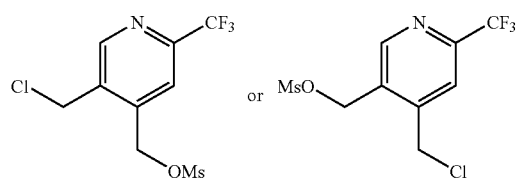

To a solution of the diol from Step A (5.46 g, 26.4 mmol) in DCM (150 mL), was added triethylamine (13.23 mL, 94.9 mmol) and DMAP (20 mg). After cooled to 0° C., the reaction mixture was slowly treated with methanesulfonyl chloride (6.73 mL, 87.0 mmol). The reaction mixture was then stirred for 1.5 hr at 0° C. The solvent was evaporated and the residue was purified by flash column (silica gel, 50% EtOAc/hexane to 60% EtOAC/hexane ) to yield the chloromesylate (5.34 mg, 82.7%). ¹H-NMR (400 MHz, CDCl₃) δ 8.72 (s, 1H), 7.81 (s, 1H), 5.45 (s, 2H), 4.70 (s, 2H), 3.15 (s, 3H). ESI-MS calc. For C9H9C1F3NO3S: 302.99; Found: 304 (M+H)

Step C:

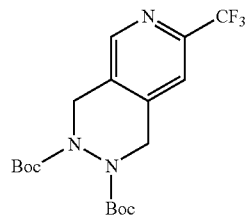

To a solution of Di-tert-butyl hydrazodiformate(4.07 g, 17.5 mmol) in THF (40 mL), was added potassium tert-butoxide (3.93 g, 35.0 mmol). After the reaction mixture was stirred for 1 hr, the chloromesylate from Step B (5.32 g, 17.5 mmol) in THF (40 mL) was slowly added. The reaction mixture was continuously stirred for 1 hr. the solvent was evaporated under vacuum and the residue was purified on column chromatography (silica gel, 25% EtOAc/hexane to 30% EtOAc/hexane) to yield di(tert-butyl) 7-(trifluoromethyl)-1,4-dihydropyrido[3,4-d]pyridazine-2,3-dicarboxylate (4.53 g, 83.9%). ¹H-NMR (400 MHz, CDCl₃) δ 8.55 (s, 1H), 7.50 (s, 1H), 5.17 (m, 2H), 4.20 (m, 2H), 1.50 (s, 18H). ESI-MS calc. For C18H24F3N3O4: 403.17; Found: 404 (M+H).

Step D:

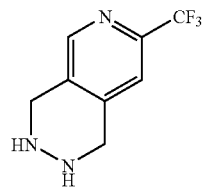

A solution of the product from Step C (4.53 g, 11.24 mmol) in 4N HCl/Dioxane (55 ML, 225 mmol) was stirred overnight. The solvent was evaporated to yield the 7-(trifluoromethyl)-1,2,3,4-tetrahydropyrido[3,4-d]pyridazine HCl salt (2.98 g, 100%). ¹H-NMR (400 MHz, CD₃OD) δ 8.63 (s, 1H), 7.78 (s, 1H), 4.80 (s, 2H), 4.48 (s, 2H). ESI-MS calc. For C8H8F3N3: 203.07; Found: 204 (M+H).

Step E:

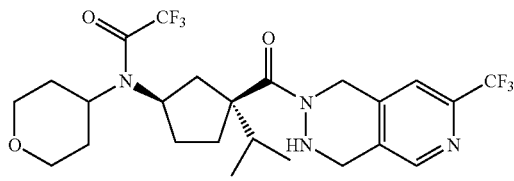

To a solution of Intermediate 2 (250 mg, 0.712 mmol) in DCM (100 mL), was added 2M oxalyl chloride in DCM (0.427 µL, 0.854 mmol) and DMF (~50 µL). The reaction mixture was stirred for 4 hr, and concentrated. The residue was put on high vacuum for 2 hr and dissolved in DCM (10 mL). The formed acid chloride was added into a solution of the product from Step D (267 mg, 0.854 mmol) and triethylamine (456 L, 3.28 mmol) in DCM (10 mL) at 0° C. The reaction mixture was stirred for 16 hr and concentrated. The residue was purified by flash column chromatography (silica gel, 8% [aq. NH4OH/MeOH 1/9]/DCM ) first and then by preparative TLC (100 micron) (developed by 5% MeOH/DCM) to yield the 7-(trifluoromethyl)-1,2,3,4-tetrahydropyrido[3,4-d]pyridazine amide (39.5 mg, 10.3%) and another structural isomer (42.3 mg, 11.1%). LC-MS calc. For C24H30F6N4O3: 536.22; Found: 537 (M+H).

Step F:

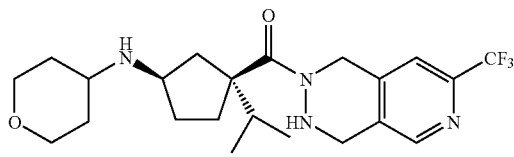

To a solution of the 7-(trifluoromethyl)-1,2,3,4-tetrahydropyrido[3,4-d]pyridazine amide (39.5 mg, 0.0736 mmol) in ethanol (5 mL), was added sodium borohydride (26 mg, 0.687 mmol). The reaction was stirred overnight. The reaction was quenched by methanol and the extra sodium borohydride was destroyed by 4N HCl in dioxane. The solvent was evaporated under vacuum and the residue was purified by preparative TLC (100 micron) (developed by 10% [aq. NH4OH/MeOH 1/9]/DCM) to yield the title compound as a free base. Its HCl salt (30.2 mg) was formed by treatment with 4N HCl/dioxane. LC-MS calc. For C22H31F3N4O2: 440.24; Found: 441 (M+H)

EXAMPLE 24

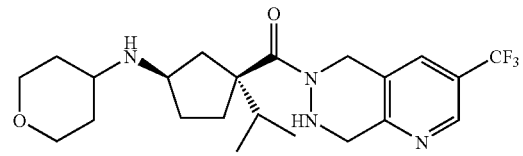

Step A:

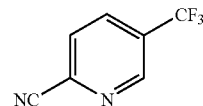

To a mixture of 2-chloro-5-trifluoromethlypyridine (100 g, 551 mmol) and zinc cyanide (97 g, 826 mmol) in DMF (200 mL), was added tetrakis(triphenylphosphine)-palladium(0) (10 g, 8.65 mmol) after nitrogen was bubbled into the reaction for 10 min. The reaction mixture was stirred at 80° C. overnight, diluted with EtOAc, filtered through celite, and partitioned between EtOAc and water. The aqueous layer was extracted by EtOAC (twice) and the combined organic layers were washed with brine, dried over Na₂SO₄, filtered, and concentrated. The residue was purified by flash column chromatography (silica gel, 5% EtOAc/hexane) to yield the target nitrile (22.7 g, 23.9%).

¹H-NMR (400 MHz, CDCl₃) δ 9.01 (s, 1H), 8.14 (d, J=8 Hz, 1H), 7.88 (d, J=8 Hz, 1H).

Step B:

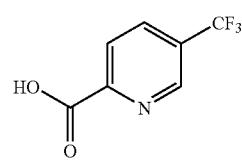

A suspension of the nitrile from Step A (20.5 g, 119.1) and concentrated HCl (190 mL) was refluxed at 110° C. overnight. The water and extra HCl were evaporated under vacuum. Residue was suspended in water (60 mL) and DCM was used to extracted the suspension for four times. The combined DCM extracts were dried over Na₂SO₄, filtered, and concentrated to yield the expected carboxylic acid (25.07 g, >100%). ¹H-NMR (400 MHz, CDCl₃) δ 9.97 (br s, 1H), 9.03 (s, 1H), 8.42 (d, J=8 Hz, 1H), 8.36 (d, J=8Hz, 1H). LC-MS calc. For C7H4F3NO2: 191.02; Found: 192 (M+H).

Step C:

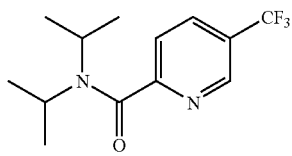

The title diisopropylamide was prepared starting from the acid from Step B in the same way as detailed in Example 22, Step A. ¹H-NMR (400 MHz, CDCl₃) δ 8.83 (s, 1H), 8.00 (d, J=8.2 Hz, 1H), 7.58 (d, J=8.2 Hz, 1H), 3.65 (m, 2H), 1.57 (s, 6H), 1.20 (s, 6H). LC-MS calc. For C13H17F3N2O: 274.13; Found: 275 (M+H).

Step D:

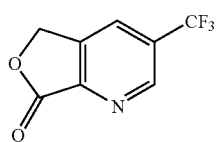

The title lactone was prepared starting from the diisopropylamide from Step C in the same way as detailed in Example 22 (Steps B, C, and D). ¹H-NMR (400 MHz, CDCl₃) δ 9.20 (s, 1H), 8.21 (s, 1H), 5.50 (s, 2H). LC-MS calc. For C8H4F3NO2: 203.02; Found: 204 (M+H).

Step E:

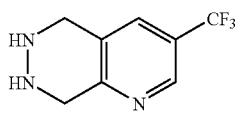

3-(Trifluoromethyl)-5,6,7,8-tetrahydropyrido[2,3-d]pyridazine was prepared starting from the lactone from Step D in the same way as detailed in Example 23 (Steps A, B, C, and D). ¹H-NMR (400 MHz, CD₃OD) δ 8.86 (s, 1H), 8.14 (s, 1H), 4.49 (s, 2H), 4.45 (s, 2H).

Step F:

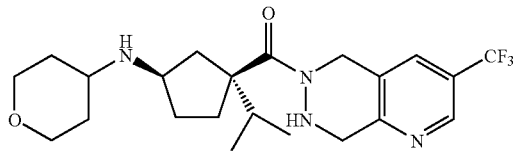

Example 24 was prepared starting from 3-(Trifluoromethyl)-5,6,7,8-tetrahydropyrido[2,3-d]pyridazine in the same way as detailed in Example 23 (Steps E, and F). ¹H-NMR (400 MHz, CDCl₃) δ 8.71 (s, 1H), 7.72 (s, 1H), 4.86 (m, 2H), 4.20 (m, 2H), 3.97 (m, 3H), 3.40 (m, 2H), 3.18 (m, 1H), 2.77 (m, 1H), 2.58 (br s, 1H), 2.46 (m, 1H), 2.25 (m, 1H), 1.92-1.78 (m, 5H), 1.61 )m, 1H), 1.41 (m, 2H), 1.27 (m, 1H), 0.92-0.82 (m, 6H). LC-MS calc. For C22H31F3N4O2: 440.24; Found: 441 (M+H).

EXAMPLE 25

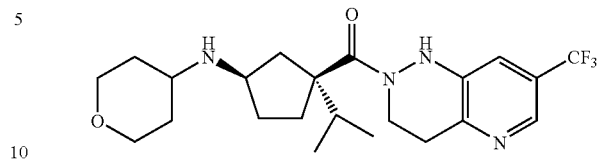

Step A:

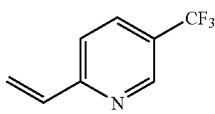

To a solution of 2-chloro-5-trifluoromethylpyridine (66 g, 360 mmol) in anhydrous DMF (100 mL) was added 2,6-di-tert-butyl 4-methyl phenol (0.44 g, 2 mmol), tributylvinyl tin (115 g, 0.36 mol) and bis-triphenylphosphine palladium dichloride (4.0 g). The reaction vessel was evacuated and purged with nitrogen three times, then the reaction mixture was heated at 85° C. overnight. LC-MS showed incomplete conversion. Additional bis-triphenylphosphine palladium dichloride (4.0 g) was added. The mixture was heated for another night, cooled to RT, poured into ice water, and extracted with ether (3×). The combined ethereal layers were washed with water and brine, dried over sodium sulfate, and evaporated. The residue was purified on FC (10% ethyl acetate/hexane) to yield the desired product as an oil (10.2 g, 16%). ¹H NMR (400 MHz, CDCl₃): 8.80 (s, 1H), 7.87 (d, J=5.9 Hz, 1H), 7.42 (d, J=8.2 Hz, 1H), 6.85 (dd, J=6.6 Hz, 1H), 6.32 (d, J=17.2 Hz, 1H), 5.60 (d, J=10.8 Hz, 1H).

Step B:

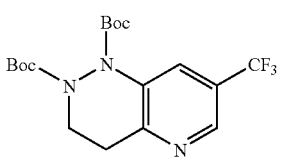

A mixture of 2-vinyl-5-trifluoromethylpyridine (Step A, Example 25) (10.2 g, 60 mmol) and di-tert-butyl hydrazodiformate (9.2 g, 40 mmol) in benzene (50 mL) was heated at 85° C. for 4 days. The benzene was removed and the residue was purified on FC (10% ethyl acetate/hexane) to yield a mixture of the corresponding mono adduct (LC-MS: 404) and bis adduct (LC-MS: 634). Further purification on MPLC (10% ethyl acetate/hexane) afforded the desired cycloaddition product (0.5 g, faster eluting). ¹H NMR (400 MHz, CDCl₃): 8.56 (s, 1H), 8.38 (br s, 1H), 4.58 (m, 1H), 3.30 (m, 2H), 3.00 (m, 1H), 1.56 (s, 9H), 1.47 (s, 9H).

Step C:

The bis-Boc cyclic hydrazine (Step B, Example 25) (480 mg, 1.2 mmol) was mixed with 5 mL of 4N HCl/dioxane for 12 h, evaporated and dried in vacuum to yield a yellow solid (280 mg). $^1$H NMR (400 MHz, CD$_3$OD): 8.65 (d, J=1.0 Hz, 1H), 7.82 (d, J=1.5 Hz, 1H), 3.82 (t, J=6.7 Hz, 2H), 3.41 (t, J=6.4 Hz, 2H). LC-MS calc. for C8H8F3N3: 203; Found: 204 (M+H).

Step D

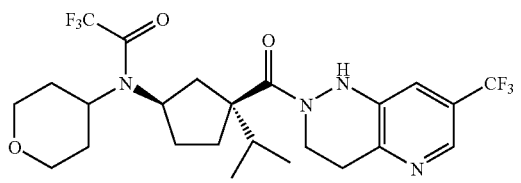

To a stirred solution of the starting Acid (Intermediate 2, 526 mg, 1.5 mmol) in dichloromethane (4 mL) was added a solution of oxalyl chloride (2N, 10 mL, 2.0 mmol) and DMF (100 µL). The mixture was stirred under nitrogen for one hour, the solvent and excess oxalyl chloride were removed under vacuum. The residue was dissolved in fresh dichloromethane (5 mL) and added into a mixture of the cyclic hydrazine (Step C, Example 25) (280 mg, 0.91 mmol) and DIEA (0.9 mL, 5 mmol) in dichloromethane (10 mL). The mixture was stirred for one hour, applied onto a silica gel column and eluted with 10% [aq. NH4OH/MeOH/1/9]/dichloromethane. The title compound was obtained as a brown solid (802 mg, >100%) which was contaminated with the starting acid (by LC-MS). This material was used in next step without further purification. LC-MS calc. for C24H30F6N4O3: 536; Found: 537 (M+H).

Step E:

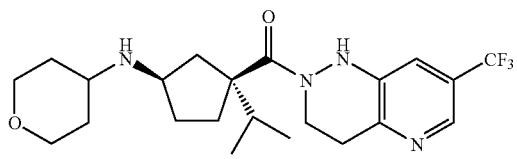

The crude coupling product (Step D, Example 25) (~800 mg) was dissolved in 40 mL of ethanol and treated with sodium borohydride (370 mg, 10 mmol). After bubble formation subsided, LC-MS showed ~50% conversion. Additional sodium borohydride (200 mg) was added. The mixture was stirred for 6 h, quenched with methanol and 4N HCl/dioxane. The solvents were removed and the residue was passed through a short silica gel column (eluted with 10% [aq. NH4OH/MeOH 1/9]/DCM). Further purification on preparative TLC gave two components. The faster isomer was found to be the starting TFA amide (Step D, Example 25, 110 mg). The slower isomer was the desired product (182 mg). LC-MS calc. for C22H31F3N4O2: 440; Found: 441 (M+H).

EXAMPLE 26

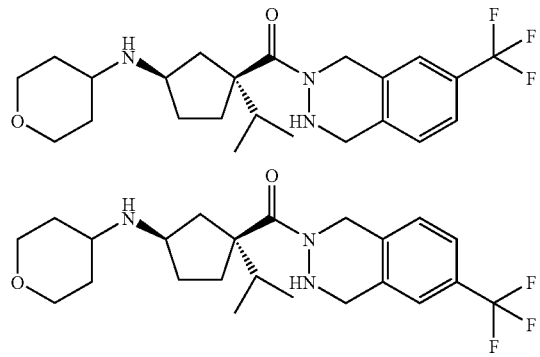

Step A:

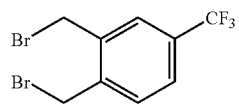

3,4-dimethylbenzotrifluoride (3.48 g, 20 mmol) was dissolved in carbontetrachloride and N-bromosuccinimide (7.7 g, 43 mmol, 2.2 eq) and AIBN (200 mg) were added. The solution was refluxed for 4 h, cooled to ice temperature. Hexane was added and the succinimide was filtered off. The filtrate was then concentrated to dryness and subjected to flash chromatography eluting with 5-10% ethyl acetate in hexane, yielding 2.2 g of product plus some mono brominated product.

NMR (500 MHz, CDCl$_3$) δ: 7.65 (broad s, 1H); 7.63 (d, J=8, 1H); 7.57 (d, J=8, 1H); 4.68 (s, 4H); MS (ES) m/z: 400.3 [MH$^+$].

Step B:

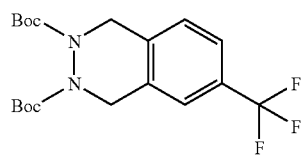

Di-tert-butylhydrazodiformate (1.53 g, 6.6 mmol) was dissolved in butanol (40 mL) and potassium tert-butoxide (1.48 g, 13.2 mmol) was added. The mixture was stirred for 1 h, 3,4-bis(bromomethyl)benzotrifluoride (2.2 g, 6.6 mmol) was added, then the reaction mixture was stirred overnight. The precipitate of KBr was filtered off and the filtrate concentrated to dryness. Crystals which formed were filtered off (600 mg) and were washed with hexane. The filtrate was concentrated and the residue was chromatographed (5-10% ethylacetate in hexane) yielding another 600 mg of product.

Step C:

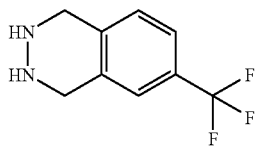

The diboc compound from Step B (500 mg, 1.24 mmol) was dissolved in THF (1 mL) and 4N HCl in dioxane (20 mL) was added and the reaction mixture was stirred overnight. Ether was added and the precipitate was filtered off yielding 300 mg of 6-(trifluoromethyl)-1,2,3,4-tetrahydrophthalazine.

NMR (500 MHz, CD$_3$OD) δ : 7.63, (d, J=8, 1H); 7.61 (s, 1H); 7.45 (d, J=8, 1H); 4.41 (s, 4H); 3.54 (m, 1H); 3.27 (m, 4H); 2.93 (m, 1H); 2.61 (m, 2H); 1.62 (m, 2H); 1.30 (m, 14H); 0.90 (t, J=6.7, 3H). MS (ES) m/z: 203.1 [MH$^+$].

Step D:

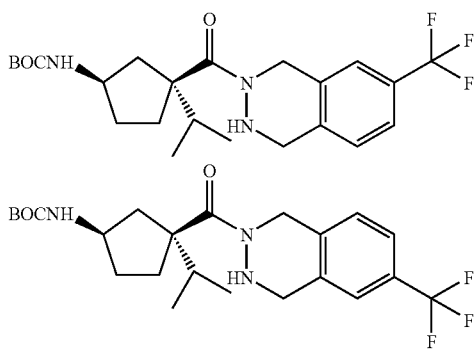

The boc aminocyclopentanecarboxylic acid, Intermediate13 (165 mg, 0.6 mmol) and 6-(trifluoromethyl)-1,2,3,4-tetrahydrophthalazine from Step C (121 mg, 6 mmole) were dissolved in dichloromethane (10 ml) and 2-chloro-1-methylpyridinium iodide (230 mg, 0.9 mmole) and triethylamine (250 ul, 185 mg, 1.5 mmole) were added. The mixture was stirred overnight and washed with brine. The dichloromethane layer was dried and evaporated. Chromatographic separation afforded the two desired isomeric amides.

Step E:

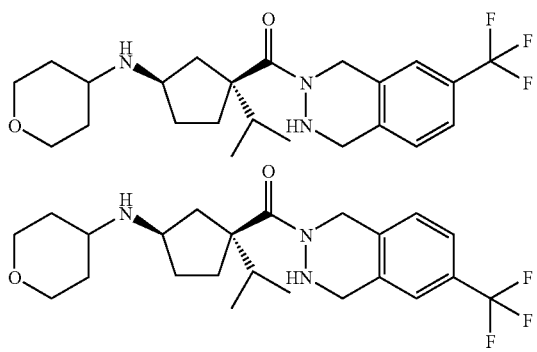

The final analogs were prepared in the same fashion as described previously in Example 22, Steps K-L.

EXAMPLE 27

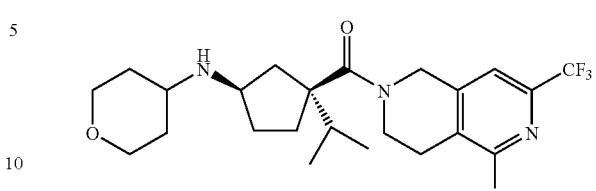

Step A:

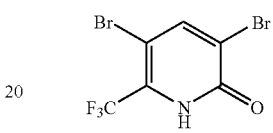

A mixture of 2-hydroxy-6-trifluoromethylpyridine (5.00 g, 30.66 mmol) and NBS (11.46 g, 64.38 mmol) in DMF (20 mL) was stirred at room temperature overnight. The reaction mixture was diluted by EtOAc, washed with water (twice) and brine, dried over Na$_2$SO$_4$, filtered, and concentrated. The residue was purified by flash column chromatography (silica gel, 30% EtOAc/hexane) to yield the title dibromopyridone (10.05 g, 100%). $^1$H-NMR (400 MHz, CDCl$_3$) δ 8.15 (s, 1H). ESI-MS calc. For C6H2Br2F3NO: 318.85; Found: 322 (M+H+2).

Step B:

To a suspension of the dibromopyridone from Step A (10 g, 31.16 mmol) and silver nitrite (5.73 g, 20.77 mmol) in benzene (40 mL), was added iodomethane (2.33 mL, 37.39 mL). The reaction mixture was stirred at 50° C. under nitrogen at dark for 24 hr. The reaction mixture was diluted by benzene, filtered. The filtrate was washed by 5% NaHCO3, water (twice), dried over Na$_2$SO$_4$, filtered, and concentrated. The residue was purified by flash column chromatography (silica gel, 30% EtOAc/hexane) to yield 3,5-dibromo-2-methoxy-6-(trifluoromethyl)pyridine (6.71 g, 64.3%). $^1$H-NMR (400 MHz, CDCl$_3$) δ 8.07 (s, 1H), 4.02 (s, 3H).

Step C:

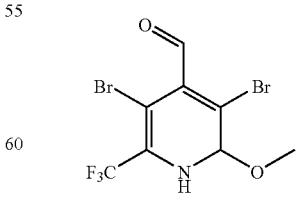

To a flame-dried 100 mL round-bottomed flask, was added dry THF (15 mL). The solution was cooled to −78° C. before diisopropylamine (460 μL, 3.28 mmol), 2.5 M n-butyllithium in hexane (1.31 mL, 3.28 mmol), and a solution of 3,5- dibromo-2-methoxy-6-(trifluoromethyl)pyridine (1.00 g, 2.99 mmol) in dry THF (10 mL), were added sequentially. The reaction mixture was stirred at −78° C. for 10 min before methyl formate (276 μL, 4.49 mmol) was slowly added. After the reaction was stirred for another 2 hr, the mixture was warmed and stirred for 30 min at room temperature. Then the mixture was quenched with saturated ammonium chloride solution, extracted with EtOAc, washed by water and brine, dried over Na$_2$SO$_4$, and concentrated. The residue was purified by flash column chromatography (silica gel, 15% EtOAc/hexanes) to yield 3,5-dibromo-2-methoxy-6-(trifluoromethyl)isonicotinaldehyde (985 mg, 90.5%). $^1$H-NMR (400 MHz, CDCl$_3$) δ 10.10 (s, 1H), 4.11 (s, 3H).

Step D:

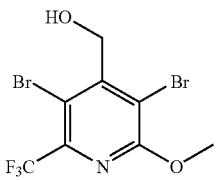

To a solution of 3,5-dibromo-2-methoxy-6-(trifluoromethyl)isonicotinaldehyde (980 mg, 2.7 mmol) in ethanol (10 mL), was added sodium borohydride (102 mg, 2.7 mmol). The reaction mixture was stirred for 20 min, concentrated, and the residue was purified by flash column (silica gel, 50% EtOAc/hexane) to yield [3,5-dibromo-2-methoxy-6-(trifluoromethyl)pyridin4-yl]methanol (717 mg, 72.8%). $^1$H-NMR (400 MHz, CDCl$_3$) δ 5.10 (s, 2H), 4.05 (s, 3H), 2.32 (br s, 1H).

Step E:

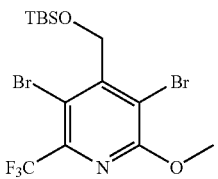

To a solution of [3,5-dibromo-2-methoxy-6-(trifluoromethyl)pyridin-4-yl]methanol (880 mg, 2.41 mmol) in THF (3 mL), was added 60% sodium hydride (107 mg, 2.65 mmol). The reaction was stirred for 30 min at room temperature after bubbles disappeared from the reaction. A solution of tert-butyl-dimethylsilyl chloride (434 mg, 2.89 mmol) was added and the reaction was then stirred for 1 hr. The solvent was evaporated and residue was purified by flash column (silica gel, 20% EtOAc/hexane) to yield the desired TBS ether (1.13 g, 97%). $^1$H-NMR (400 MHz, CDCl$_3$) δ 5.03 (s, 2H), 4.05 (s, 3H), 0.95 (s, 9H), 0.19 (s, 6H). LC-MS calc. For C14H20Br2F3NO2Si: 476.96; Found: 480 (M+H+2).

Step F:

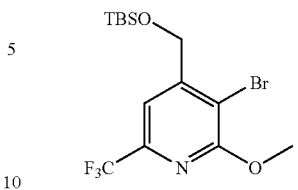

To a solution of the TBS ether from Step E (2.68 g, 3.41 mmol) in THF (50 mL), cooled at −78° C., was added 2.0 M phenyllithium in cyclohexane (1.705 mL, 3.41 mmol). After the reaction was stirred for 5 min, 10% citric acid in THF was added. The mixture was diluted by ethyl ether, washed by water and brine, dried over Na$_2$SO$_4$, filtered, and concentrated. The residue was purified by flash column chromatography (silica gel, 10% to 15% EtOAc/hexane) to yield 3-bromo-4-({[tert-butyl(dimethyl)silyl]oxy}methyl)-2-methoxy-6-(trifluoromethyl)pyridine (2.52 g, 100%). $^1$H-NMR (400 MHz, CDCl$_3$) δ 7.52 (s, 1H), 4.74 (s, 2H), 4.08 (s, 3H), 0.99 (s, 9H), 0.17 (s, 6H). LC-MS calc. For C14H21BrF3NO2Si: 399.05; Found: 400, and 402 (M+H and M+H+2).

Step G:

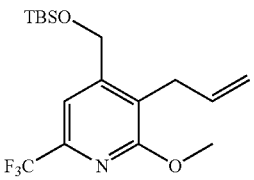

A mixture of 3-bromo-4-({[tert-butyl(dimethyl)silyl]oxy}methyl)-2-methoxy-6-(trifluoromethyl)pyridine (2.51 g, 6.27 mmol), allytributyltin (2.92 mL, 9.41 mmol), tetrakis(triphenylphosphine)palladium(0) (750 mg, 0.627 mmol) and toluene (15 mL) was flushed with nitrogen several times. The reaction mixture was stirred at reflux overnight. The reaction was filtered and concentrated under vacuum. The residue was purified by column chromatography (silica gel, 100% hexane to 5% EtOAc/hexane) to yield 3-allyl-4-({[tert-butyl(dimethyl)silyl]oxy}methyl)-2-methoxy-6-(trifluoromethyl)pyridine (2.62 g, 100%). $^1$H-NMR (400 MHz, CDCl$_3$) δ 7.55 (s, 1H), 5.85 (m, 1H), 4.93-5.11 (m, 2H), 4.74 (s, 2H), 4.04 (s, 3H), 3.37 (d, J=5Hz, 2H), 0.99 (s, 9H), 0.17 (s, 6H).

Step H:

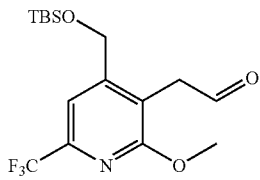

A mixture of 3-allyl-4-({[tert-butyl(dimethyl)silyl]oxy}methyl)-2-methoxy-6-(trifluoromethyl)pyridine (2.62 g, 7.25 mmol), N-methylmorphine N-oxide (849 mg, 7.25 mmol), osmium tetroxide (4 wt. % in water, 10 mL, 400 mg) in acetone/water (4:1) (100 mL) was stirred at room temperature overnight. The reaction was quenched by sodium bisulfite (3.50 g, 36 mmol). After acetone was evaporated, the mixture was diluted with water, and extracted with DCM. The organic layer was dried over Na$_2$SO$_4$, filtered, and concentrated. The residue was stirred with sodium periodate (1.86 g, 8.7 mmol) in MeOH/water (1:1) (60 mL) for 30 min. The reaction was filtered and concentrated. The residue was partitioned between ethyl acetate and water and the aqueous layer was extracted by ethyl acetate. The combined organic layers were dried over Na$_2$SO$_4$, filtered, and concentrated under vacuum. The residue was purified by column chromatography (silica gel, 30% EtOAc/hexane) to yield [4-({[tert-butyl(dimethyl)silyl]oxy}methyl)-2-methoxy-6-(trifluoromethyl)pyridin-3-yl]acetaldehyde (1.61 g, 61%). $^1$H-NMR (400 MHz, CDCl$_3$) δ 9.68 (t, J=1.5 Hz, 1H), 7.46 (s, 1H), 4.67 (s, 2H), 4.01 (s, 3H), 3.76 (d, J=5 Hz, 2H), 0.96 (s, 9H), 0.13 (s, 6H).

Step I:

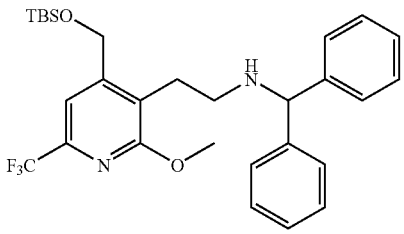

A mixture of [4-({[tert-butyl(dimethyl)silyl]oxy}methyl)-2-methoxy-6-(trifluoromethyl)pyridin-3-yl]acetaldehyde (1.55 g, 4.26 mmol), aminodiphenylmethane (1.11 mL, 6.40 mmol), and powdered molecular sieves (4 Å, 2.80 g) in DCM (20 mL) was stirred for 30 min. Then sodium triacetoxyborohydride (132 mg, 0.625 mmol) was added. The resulting mixture was stirred overnight, diluted with DCM, filtered, and washed with sat. aq. Na$_2$CO$_3$. The layers were separated, and the aq. solution was extracted with DCM. The combined DCM layers were dried over Na$_2$SO$_4$, and evaporated. The residue was purified by column chromatography (silica gel, 100% DCM) to yield N-benzhydryl-2-[4-({[tert-butyl(dimethyl)silyl]oxy}methyl)-2-methoxy-6-(trifluoromethyl)pyridin-3-yl]ethanamine (1.42 g, 62.8%). $^1$H NMR (CDCl$_3$, 400 MHz): δ 7.48 (s, 1H), 7.18-7.38 (m, 10H), 4.84 (s, 1H), 4.78 (s, 2H), 3.81 (s, 3H), 2.77 (m, 4H), 1.62 (br s, 1H), 0.97 (s, 9H), 0.12 (s, 6H). LC-MS calc. for C29H37F3N2O2Si: 530.26; Found: 531 (M+H).

Step J:

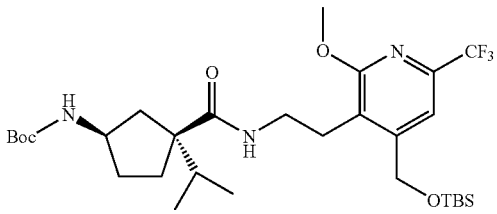

To a mixture of N-benzhydryl-2-[4-({[tert-butyl(dimethyl)silyl]oxy}methyl)-2-methoxy-6-(trifluoromethyl)pyridin-3-yl]ethanamine (1.39 g, 2.62 mmol), Intermediate 13 (712 mg, 2.62 mmol) in ethanol (100 mL), was added Pd/C. The reaction mixture was placed in a Parr apparatus and agitated under 40 lb pressure of H$_2$ overnight. The reaction was filtered through celite and concentrated under vacuum. The residue was mixed with EDC (1.51 g, 7.86 mmol), Intermediate 13 (100 mg, 0.37 mmol), DMAP (40 mg) and DIEA (913 µL, 5.24 mmol) in DCM (30 mL). The mixture was stirred overnight, diluted by DCM, washed with water and brine, dried over Na$_2$SO$_4$, filtered and concentrated under vacuum. The residue was purified by column chromatography (silica gel, 30% EtOAc/hexane) to yield the target amide (598 mg, 37%). $^1$H-NMR (400 MHz, CDCl$_3$) δ 7.50 (s, 1H), 5.98 (br s, 1H), 4.73 (s, 2H), 4.03 (m, 4H), 3.46 (q, 2H), 2.85 (t, J=7 Hz, 2H), 1.75-1.95 (m, 4H), 1.55 (m, 2H), 1.44 (m, 11H), 0.96 (s, 9H), 0.82 (m, 6H), 0.13 (s, 6H).

Step K:

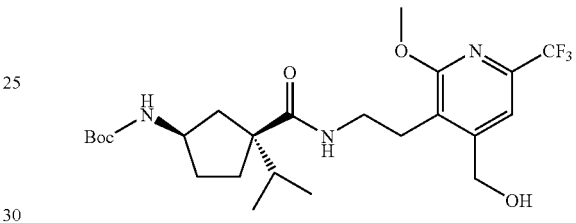

To a solution of the amide from Step J (595 mg, 0.963 mmol) in THF (10 mL), was added tetrabutylammonium fluoride (1.06 mL, 1.059 mmol). The reaction mixture was stirred for 15 min and concentrated under vacuum. The residue was purified by flash column chromatography (silica gel, 50% EtOAc/hexane) to yield the deprotected alcohol (427 mg, 88%).

Step L:

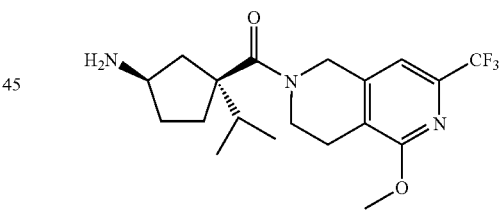

To a solution of the alcohol from Step K (100 mg, 0.199 mmol) and triethylamine (166 mL, 1.192 mmol) in DMSO (1 mL), was added a solution of sulfur trioxide pyridine complex (127 mg, 0.795 mmol) in DMSO (3 mL). The reaction mixture was stirred for 20 min, diluted by EtOAc, washed by water and brine, dried over Na$_2$SO$_4$, filtered, and concentrated. The residue was then mixed with triethylsilane (318 uL, 1.99 mmol) in DCM (5 mL), cooled to −78° C., and boron trifluoride-diethyl etherate (50 µL, 0.398 mmol) was added. The reaction mixture Was stirred at −78° C. for 1 hr and then stirred at room temperature for 20 min before it was quenched with Na$_2$CO$_3$, and concentrated. The residue was purified by preparative TLC (1000 micron) (developed by 30% EtOAc/hexane) to yield tert-butyl (1R,3S)-3-isopropyl-3-{[5-methoxy-7-(trifluoromethyl)-3,4-dihydro-2,6-naphthyridin-2(1H)-yl]carbonyl}cyclopentylcarbamate (51.5 mg, 53.4%).

¹H-NMR (400 MHz, CDCl₃) δ 7.05 (s, 1H), 4.66-4.90 (m, 3H), 4.02 (s, 3H), 3.80 (m, 2H), 3.77 (m, 1H), 2.75 (m, 2H), 2.04-2.30 (in, 4H), 1.80 (m, 2H), 1.60 (m, 1H), 1.43 (s, 9H), 0.88 (m, 6H). LC-MS calc. For C24H34F3N3O4: 485.25; Found: 386 (M+H–100). The Boc protected intermediate was treated with 4N HCl/Dioxane (0.5 mL) at room temperature overnight to yield (1R,3S)-3-isopropyl-3-{[5-methoxy-7-(trifluoromethyl)-3,4-dihydro-2,6-naphthyridin-2(1l)-yl]carbonyl}cyclopentylamine (41.5 mg).

Step M:

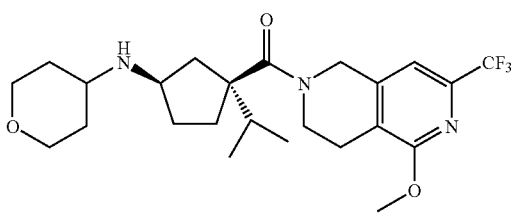

Example 27 was prepared starting from (1R,3S)-3-isopropyl-3-{[5-methoxy-7-(trifluoromethyl)-3,4-dihydro-2,6-naphthyridin-2(1H)-yl]carbonyl}cyclopentylamine as detailed in Example 22, Step L.

LC-MS calc. For C24H34F3N3O3: 469.26; Found: 470 (M+H).

EXAMPLE 28

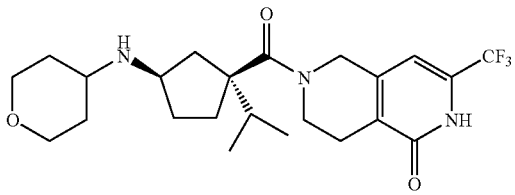

To a solution of Example 7 (25.4 mg, 0.0468 mmol), sodium iodide (7.0 mg, 0.047 mmol) in acetonitrile (2 mL), was slowly added trimethylsilyl chloride (5.1 mg, 0.047 mmol). The reaction mixture was stirred for 1 hr, concentrated, and the residue was purified by preparative TLC (1000 micron) (developed by 8% [aq. NH4OH/MeOH 1/9]/DCM) to yield the title compound as a free base. Its HCl salt (13.7 mg) was formed by treatment with 4N HCl/dioxane. LC-MS calc. for C23H32F3N3O3: 455.24; Found: 456 (M+H).

INTERMEDIATE 14

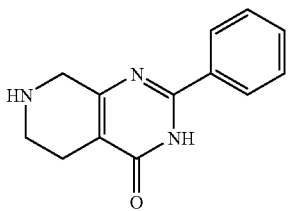

Step A:

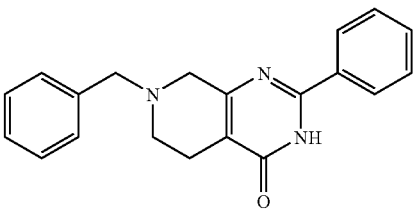

A solution of ethyl 1-benzyl-3-oxopiperidine-4-carboxylate (5.0 g, 16.79 mmol) and benzamidine (2.01 g, 16.79 mmol) in anhydrous ethanol (150 ml) at rt was treated with 2.32 g (101 mmol) sodium and the resulting mixture stirred at 100° C. for 3 h. The solvent was evaporated under reduce pressure and the resulting solid treated with MeOH (10 ml) and ether (200 ml). The product 2.56 g (42%) was filtered and washed with ether. No further purification was required. ¹H NMR (CDCl₃, 400 MHz): 7.92 (d,2H), 7.50-7.52 (m, 3H), 7.28-7.41 (m, 5H), 3.75 (s, 2H), 3.50 (s, 2H), 2.79 (t, 2H), 2.62 (t, 2H). LC-MS for C₂₀H₁₉N₃O [M+J]⁺ calculated 318.38, found 318.4.

Step B:

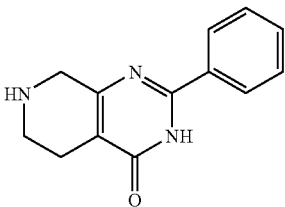

A suspension of the product from Step A (0.4 g, 1.26 mmol) in DCM (10 ml) at 0° C. was treated with 1-chloroethyl chloroformate (1.80 ml, 1.26 mmol) and the mixture stirred for 15 min. The mixture was them stirred at 90° C. for 2 h and an additional 0.5 eq of chloroformate reagent was added. After 30 min the solvent was evaporated. The resulting white solid was treated with MeOH (10 ml) and stirred at 65° C. for 1 h. The solvent was evaporated to afford the product as a white solid (HCl Salt). Further purification of the title compound can be accomplished in two step sequences involving N-Boc protection followed by chromatography. Removal of Boc group with HCl EtOAc gave 0.185 g of the title compound. ¹H NMR (CDCl₃, 400 MHz): 7.78 (d, 2H), 7.67 (d, 1H), 7.52 (t, 2H), 4.20 (s, 2H), 3.49 (t, 2H), 2.78 (t, 2H).

EXAMPLE 29

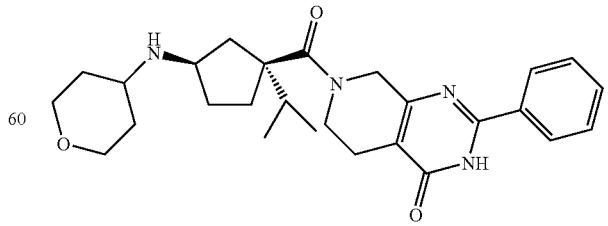

To a solution of the Intermediate 2 (0.1 g, 0.28 mmol) in anhydrous DCM (2.0 ml) under nitrogen was added oxalyl-chloride and the resultant mixture was stirred at rt for 2 h. The solvent was evaporated and the resulting oil dried under vacuo. The dried acid chloride was taken in DCM (2.0 ml) and treated with Intermediate 14 (0.168 g, 0.53 mmol) dissolved in 2 ml TEA. After 18 h the reaction was quenched with water and extracted with DCM. Flash Chromatography afforded 15.0 mg of the trifluoroacetyl protected amine that was deprotected with $NaBH_4$ as described previously. Reverse phase purification afforded 5.6 mg of the desired product, Example 29. LC-MS for $C_{27}H_{36}N_4O_3$ $[M+H]^+$ calculated 465.60, found 465.6.

What is claimed is:

1. A compound of formula I:

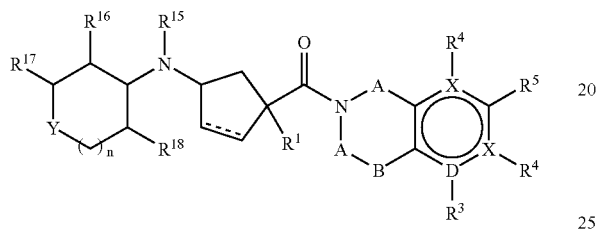

I wherein:

A, B, X, and D are defined as follows:

A is $-CR^8R^8-$,
- where $R^8$ is independently selected from hydrogen, $C_{1-6}$alkyl, $C_{0-4}$alkylCOR$^{11}$ and
- where $R^{11}$ is selected from the group consisting of hydroxy, hydrogen, $C_{1-6}$ alkyl, $-O-C_{1-6}$alkyl, benzyl, phenyl and $C_{3-6}$ cycloalkyl, where said alkyl, phenyl, benzyl, and cycloalkyl groups are unsubstituted or substituted with 1-3 substituents where said substituents are independently selected from the group consisting of halo, hydroxy, $C_{1-3}$alkyl, $C_{1-3}$alkoxy, $-CO_2H$, $-CO_2-C_{1-6}$ alkyl and trifluoromethyl;

B is $-O-$;

X is carbon;

D is carbon;

$R^{12}$ is selected from the group consisting of hydrogen, $C_{1-6}$ alkyl, benzyl and phenyl, and $C_{3-6}$ cycloalkyl where said alkyl, phenyl, benzyl, and cycloalkyl groups are unsubstituted or substituted with 1-3 substituents where said substituents are independently selected from the group consisting of halo, hydroxy, $C_{1-3}$alkyl, $C_{1-3}$alkoxy, $-CO_2H$, $-CO_2-C_{1-6}$ alkyl, and trifluoromethyl, $R^{13}$ is selected from the group consisting of hydrogen, $C_{1-6}$ alkyl, $-O-C_{1-6}$alkyl, benzyl, phenyl and $C_{3-6}$ cycloalkyl where said alkyl, phenyl, benzyl, and cycloalkyl groups are unsubstituted or substituted with 1-3 substituents where said substituents are independently selected from the group consisting of halo, hydroxy, $C_{1-3}$alkyl, $C_{1-3}$alkoxy, $-CO_2H$, $-CO_2-C_{1-6}$ alkyl and trifluoromethyl, $R^{14}$ is selected from the group consisting of hydroxy, $C_{1-6}$ alkyl, $-O-C_{1-6}$alkyl, benzyl, phenyl and $C_{3-6}$ cycloalkyl where said alkyl, phenyl, benzyl, and cycloalkyl groups are unsubstituted or substituted with 1-3 substituents where said substituents are independently selected from the group consisting of halo, hydroxy, $C_{1-3}$alkyl, $C_{1-3}$alkoxy, $-CO_2H$, $-CO_2-C_{1-6}$ alkyl and trifluoromethyl, Y is selected from the group consisting of $-O-$, $-NR^{12}-$, $-S-$, $-SO-$, $-SO_2-$, and $-CR^{11}R^{11}-$, $-NSO_2R^{14}-$, $-NCOR^{13}-$, $-NCONR^{12}R^{12}-$, $-CR^{11}COR^{11}-$, $-CR^{12}OCOR^{13}-$ and $-CO-$;

$R^1$ is selected from the group consisting of hydrogen, $-C_{1-6}$alkyl, $-C_{0-6}$alkyl-O-$C_{1-6}$alkyl, $-C_{0-6}$alkyl-S-$C_{1-6}$alkyl, $-(C_{0-6}$alkyl)-$(C_{3-7}$cycloalkyl)-$(C_{0-6}$ alkyl), hydroxy, heterocycle, $-CN$, $-NR^{12}R^{12}$, $-NR^{12}COR^{13}$, $-NR^{12}SO_2R^{14}$, $-COR^{11}$, $-CONR^{12}R^{12}$, and phenyl, where said alkyl and said cycloalkyl are unsubstituted or substituted with 1-7 substituents where said substituents are independently selected from the group consisting of:

(a) halo,
(b) hydroxy,
(c) $-O-C_{1-3}$alkyl,
(d) trifluoromethyl,
(f) $C_{1-3}$alkyl,
(g) $-O-C_{1-3}$alkyl,
(h) $-COR^{11}$,
(i) $-SO_2R^{14}$,
(j) $-NHCOCH_3$,
(k) $-NHSO_2CH_3$,
(l) -heterocycle,
(m) $=O$, and
(n) $-CN$, and where said phenyl and heterocycle are unsubstituted or substituted with 1-3 substituents where said substituents are independently selected from the group consisting of halo, hydroxy, $-COR^{11}$, $C_{1-3}$alkyl, $C_{1-3}$alkoxy and trifluoromethyl;

and where heteroclye is selected from the group consisting of benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, oxetanyl, pyranyl, pyrazinyl, pyrazolyl, pyridazinyl, pyridopyridinyl, pyridazinyl, pyridyl, pyrimidyl, pyrrolyl, quinazolinylyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methlenedioxybenzoyl, tetrahydrofuranyl, and tetrahydrothienyl, and N-oxides thereof;

$R^3$ is selected from the group consisting of:
(a) hydrogen,
(b) $C_{1-3}$alkyl, optionally substituted with 1-3 fluoro,
(c) $-O-C_{1-3}$alkyl, optionally substituted with 1-3 fluoro,
(d) hydroxy,
(e) chloro,
(f) fluoro, (g) bromo,
(h) phenyl, and
(i) heterocycle;

$R^4$ is selected from the group consisting of:
(a) hydrogen,
(b) $C_{1-3}$alkyl, optionally substituted with 1-3 fluoro,
(c) —O—$C_{1-3}$alkyl, optionally substituted with 1-3 fluoro,
(d) hydroxy,
(e) chloro,
(f) fluoro,
(g) bromo,
(h) phenyl, and
(i) heterocycle;

$R^5$ is selected from the group consisting of:
(a) $C_{1-6}$alkyl, where alkyl is unsubstituted or substituted with 1-6 fluoro and optionally substituted with hydroxyl,
(b) —O—$C_{1-6}$alkyl, where alkyl is unsubstituted or substituted with 1-6 fluoro,
(c) —CO—$C_{1-6}$alkyl, where alkyl is unsubstituted or substituted with 1-6 fluoro,
(d) —S—$C_{1-6}$alkyl, where alkyl is unsubstituted or substituted with 1-6 fluoro,
(e) -pyridyl, which is unsubstituted or substituted with one or more substituents selected from the group consisting of: halo, trifluoromethyl, $C_{1-4}$alkyl, and $COR^{11}$,
(f) fluoro,
(g) chloro,
(h) bromo,
(i) —$C_{4-6}$cycloalkyl,
(j) —O—$C_{4-6}$cycloalkyl,
(k) phenyl, which is unsubstituted or substituted with one or more substituents selected from the group consisting of: halo, trifluoromethyl, $C_{1-4}$alkyl, and $COR^{11}$,
(l) —O-phenyl, which is unsubstituted or substituted with one or more substituents selected from the group consisting of: halo, trifluoromethyl, $C_{1-4}$alkyl, and $COR^{11}$,
(m) —$C_{3-6}$cycloalkyl, where alkyl is unsubstituted or substituted with 1-6 fluoro,
(n) —O—$C_{3-6}$cycloalkyl, where alkyl is unsubstituted or substituted with 1-6 fluoro,
(o) -heterocycle,
(p) —CN and
(q) —$COR^{11}$;

$R^{15}$ is selected from the group consisting of:
(a) hydrogen and
(b) $C_{1-6}$alkyl, which is unsubstituted or substituted with 1-3 substituents where said substituents are independently selected from the group consisting of halo, hydroxy, —$CO_2H$, —$CO_2C_{1-6}$alkyl, and —O—$C_{1-3}$alkyl;

$R^{16}$ is selected from the group consisting of:
(a) hydrogen,
(b) $C_{1-6}$alkyl, where alkyl is unsubstituted or substituted with 1-6 substituents where the substituents are chosen from the group: fluoro, $C_{1-3}$alkoxy, hydroxy, and —$COR^{11}$,
(c) fluoro,
(d) —O—$C_{1-3}$alkyl, where alkyl is unsubstituted or substituted with 1-3 fluoro,
(e) $C_{3-6}$ cycloalkyl,
(f) —O—$C_{3-6}$cycloalkyl,
(g) hydroxy,
(h) —$COR^{11}$ and
(i) —$OCOR^{13}$,
or $R^{15}$ and $R^{16}$ may be joined together via a $C_{2-4}$alkyl or a $C_{0-2}$alkyl-O—$C_{1-3}$alkyl chain to form a 5-7 membered ring;

$R^{17}$ is selected from the group consisting of:
(a) hydrogen,
(b) $C_{1-6}$alkyl, where alkyl may be unsubstituted or substituted with 1-6 substituents where said substituents are chosen from the group: fluoro, $C_{1-3}$alkoxy, hydroxy, and —$COR^{11}$,
(c) $COR^{11}$,
(d) hydroxy, and
(e) —O—$C_{1-6}$alkyl, where alkyl may be unsubstituted or substituted with 1-6 substituents where said substituents are chosen from the group consisting of fluoro, $C_{1-3}$alkoxy, hydroxy, and —$COR^{11}$,
or $R^{16}$ and $R^{17}$ are joined together by a $C_{1-4}$alkyl chain or a $C_{0-3}$alkyl-O—$C_{0-3}$alkyl chain to form a 3-6 membered ring;

$R^{18}$ is selected from the group consisting of:
(a) hydrogen,
(b) $C_{1-6}$alkyl, where alkyl is unsubstituted or substituted with 1-6 fluoro,
(c) fluoro,
(d) —O—$C_{3-6}$cycloalkyl, and
(e) —O—$C_{1-3}$alkyl, where alkyl is unsubstituted or substituted with 1-6 fluoro,
or $R^{16}$ and $R^{18}$ are joined together by a $C_{2-3}$alkyl chain to form a 5-6 membered ring, where said alkyl are unsubstituted or substituted with 1-3 substituents where said substituents are independently selected from the group consisting of halo, hydroxy, —$COR^{11}$, $C_{1-3}$alkyl, and $C_{1-3}$alkoxy,
or $R^{16}$ and $R^{18}$ are joined together by a $C_{1-2}$alkyl-O—$C_{1-2}$alkyl chain to form a 6-8 membered ring, where said alkyl are unsubstituted or substituted with 1-3 substituents where said substituents are independently selected from the group consisting of halo, hydroxy, —$COR^{11}$, $C_{1-3}$alkyl, and $C_{1-3}$alkoxy,
or $R^{16}$ and $R^{18}$ are joined together by a —O—$C_{1-2}$alkyl-O-chain to form a 6-7 membered ring, where said alkyl are unsubstituted or substituted with 1-3 substituents where said substituents are independently selected from the group consisting of halo, hydroxy, —$COR^{11}$, $C_{1-3}$alkyl, and $C_{1-3}$alkoxy;

n is selected from 0, 1 and 2;
the dashed line represents a single or a double bond;
and pharmaceutically acceptable salts thereof and individual diastereomers thereof.

2. A compound of claim 1 of formula Ia:

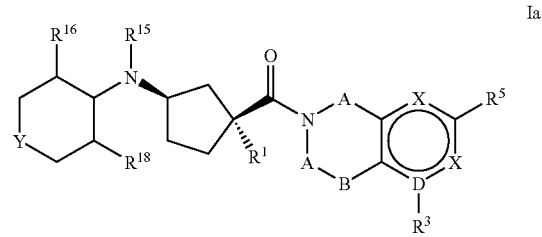

wherein $R^1$, $R^3$, $R^5$, $R^{15}$, $R^{16}$, $R^{18}$, A, B, D, X, and Y are defined in claim 1, and pharmaceutically acceptable salts and individual diastereomers thereof.

3. A compound of claim 1 of formula Ib:

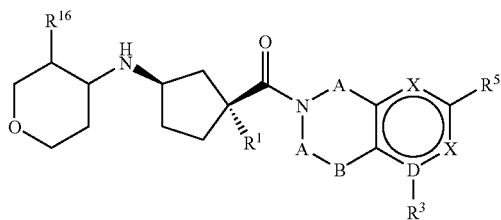

wherein $R^1$, $R^3$, $R^5$, $R^{16}$, A, B, D, and X are defined in claim 1, and pharmaceutically acceptable salts and individual diastereomers thereof.

4. A compound of claim 1 of formula Ic:

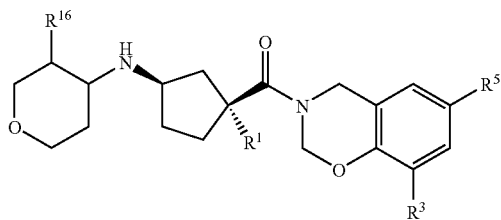

wherein $R^1$, $R^3$, $R^5$ and $R^{16}$ are defined in claim 1, and pharmaceutically acceptable salts and individual diastereomers thereof.

5. A compound of claim 1 wherein Y is selected from the group consisting of: —O—, —CH$_2$—, —S—, —SO—, and —SO$_2$—.

6. A compound of claim 1 wherein $R^1$ is selected from the group consisting of
  (1) —C$_{1-6}$alkyl, which is unsubstituted or substituted with 1-6 substituents where said substituents are independently selected from the group consisting of:
    (a) halo,
    (b) hydroxy,
    (c) —O—C$_{1-3}$alkyl,
    (d) trifluoromethyl and
    (e) —COR$^{11}$,
  (2) —C$_{0-6}$alkyl-O—C$_{1-6}$alkyl-, which is unsubstituted or substituted with 1-6 substituents where said substituents are independently selected from the group consisting of
    (a) halo,
    (b) trifluoromethyl and
    (c) —COR$^{11}$,
  (3) —(C$_{3-5}$cycloalkyl)-(C$_{0-6}$alkyl), which is unsubstituted or substituted with 1-7 substituents where said substituents are independently selected from the group consisting of
    (a) halo,
    (b) hydroxy,
    (c) —O—C$_{1-3}$alkyl,
    (d) trifluoromethyl and
    (e) —COR$^{11}$, and
  (4) phenyl or heterocycle which is unsubstituted or substituted with 1-3 substituents where said substituents are independently selected from the group consisting of
    (a) halo,
    (b) hydroxy,
    (c) —O—C$_{1-3}$ alkyl,
    (d) trifluoromethyl, and
    (e) —COR$^{11}$.

7. A compound of claim 6 wherein $R^1$ is C$_{1-6}$alkyl which is unsubstituted or substituted with 1-5 substituents where said substituents are independently selected from the group consisting of:
  (a) hydroxy, and
  (b) fluoro.

8. A compound of claim 7 wherein $R^1$ is selected from the group consisting of:
  (a) isopropyl,
  (b) —CH(OH)CH$_3$, and
  (c) —CH$_2$CF$_3$.

9. A compound of claim 1 wherein D is carbon and $R^3$ is selected from:
  (a) hydrogen
  (b) halo
  (c) hydroxy
  (d) C$_{1-3}$alkyl, where said alkyl is unsubstituted or substituted with 1-6 substituents independently selected from the group consisting of fluoro, and hydroxy,
  (e) —COR$^{11}$,
  (f) —CONR$^{12}$R$^{12}$,
  (g) -heterocycle,
  (h) —NR$^{12}$—SO$_2$—NR$^{12}$R$^{12}$,
  (i) —NR$^{12}$—SO$_2$—R$^{14}$,
  (j) —SO$_2$—NR$^{12}$R$^{12}$,
  (k) -nitro and
  (l) —NR12R12.

10. A compound of claim 9 wherein $R^3$ is selected from the group consisting of:
  (a) fluoro,
  (b) trifluoromethyl and
  (c) hydrogen.

11. A compound of claim 10 wherein D $R^3$ is
  (a) fluoro or
  (b) hydrogen.

12. A compound of claim 1 wherein X $R^4$ is selected from the group consisting of:
  (a) hydrogen,
  (b) trifluoromethyl and
  (c) halo.

13. A compound of claim 12 wherein X $R^4$ is hydrogen.

14. A compound of claim 1 wherein $R^5$ is selected from the group consisting of
  (a) C$_{1-3}$alkyl substituted with 1-6 fluoro,
  (b) chloro,
  (c) bromo,
  (d) —O-phenyl, which is unsubstituted or substituted with one or more substituents selected from the group consisting of: halo and trifluoromethyl,
  (e) phenyl, which is unsubstituted or substituted with one or more substituents selected from the group consisting of: halo and trifluoromethyl, and
  (f) —O—C$_{1-3}$alkyl substituted with 1-6 fluoro.

15. A compound of claim 14 wherein $R^5$ is selected from the group consisting of:
  (a) trifluoromethyl,
  (b) trifluoromethoxy,
  (c) bromo, and
  (d) chloro.

16. A compound of claim 15 wherein $R^5$ is selected from trifluoromethyl and trifluoromethoxy.

17. A compound of claim 1 wherein $R^{15}$ is hydrogen or methyl.

18. A compound of claim 1 wherein $R^{16}$ is selected from the group consisting of:
   (a) hydrogen,
   (b) $C_{1-3}$alkyl, which is unsubstituted or substituted with 1-6 fluoro,
   (c) —O—$C_{1-3}$alkyl,
   (d) fluoro, and
   (e) hydroxy.

19. A compound of claim 18 wherein $R^{16}$ is selected from the group consisting of:
   (a) hydrogen,
   (b) trifluoromethyl,
   (c) methyl,
   (d) methoxy,
   (e) ethoxy,
   (f) ethyl,
   (g) fluoro, and
   (h) hydroxy.

20. A compound of claim 19 wherein $R^{16}$ is selected from the group consisting of:
   (a) hydrogen,
   (b) methyl, and
   (c) methoxy.

21. A compound of claim 1 wherein $R^{18}$ is selected from the group consisting of:
   (a) hydrogen,
   (b) methyl, and
   (c) methoxy.

22. One or more compounds of claim 1 selected from the group consisting of:

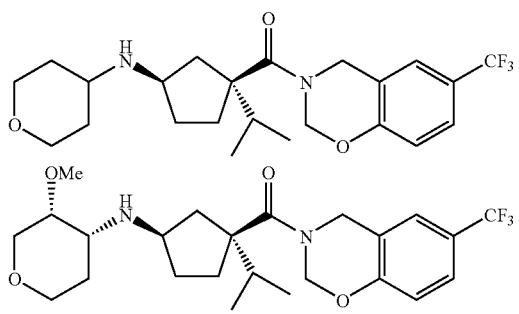

-continued

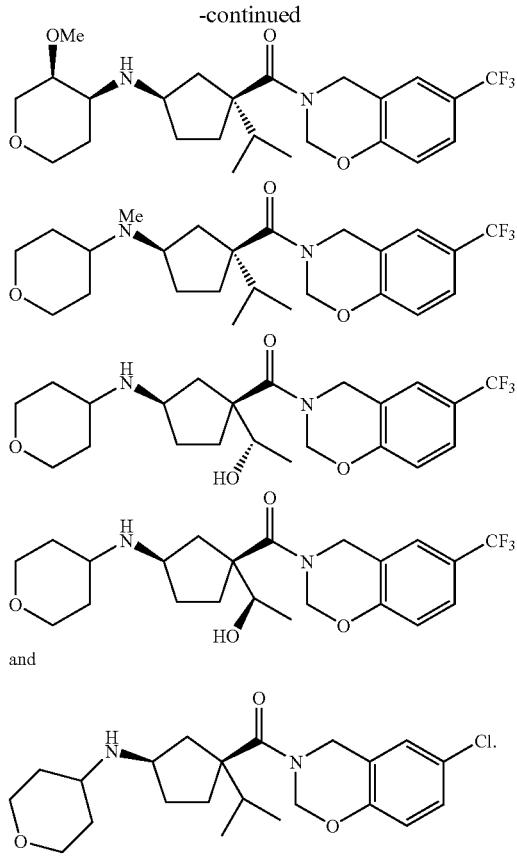

and

23. A compound of claim 1 wherein $R^{16}$ and $R^{18}$ are joined together by a —$CH_2CH_2$- chain or a —$CH_2CH_2CH_2$- chain to form a cyclopentyl ring or a cyclohexyl ring.

24. A pharmaceutical composition which comprises an inert carrier and a compound of claim 1.

25. A method for modulation of chemokine receptor CCR-2 activity in vitro which comprises the administration of an effective amount of the compound of claim 1.

26. A method for treating atherosclerosis which comprises the administration to a patient of an effective amount of the compound of claim 1.

27. A method for treating rheumatoid arthritis which comprises the administration to a patient of an effective amount of the compound of claim 1.

* * * * *